(12) United States Patent
Frydman et al.

(10) Patent No.: US 6,392,098 B1
(45) Date of Patent: May 21, 2002

(54) CONFORMATIONALLY RESTRICTED POLYAMINES

(75) Inventors: Benjamin J. Frydman, Madison; Laurence J. Marton, Fitchburg; Venodhar K. Reddy, Madison; Aldonia L. Valasinas, Madison; Donald T. Witiak, Madison, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/280,278

(22) Filed: Mar. 29, 1999

Related U.S. Application Data

(63) Continuation of application No. 08/951,015, filed on Oct. 15, 1997, now Pat. No. 5,889,061.

(51) Int. Cl.$^7$ .............................. A61K 31/13
(52) U.S. Cl. .................. 564/509; 564/510; 514/674
(58) Field of Search .................. 514/674; 564/509, 564/510

(56) References Cited

U.S. PATENT DOCUMENTS 5,889,061 A * 3/1999 Frydman et al.

FOREIGN PATENT DOCUMENTS

| EP | 0 270 349 A2 | 6/1988 |
|---|---|---|
| EP | 0 349 224 A2 | 6/1989 |
| WO | WO 95/18091 | 7/1995 |

OTHER PUBLICATIONS

Ashton, Wallace T.; Meurer, Laura Canning; Cantone, Christine L.; Field, A. Kirk; Hannah, John, Karkas, John D., Liou, Richard; Patel, Gool F.; Perry, Helen C.; Wagner, Arthur F.; Walton, Edward, and Tolman, Richard L., *J. Med. Chem* (1988) 31:2304.

Bergeron, R.J.; McManis, J.S.; Liu, C.Z.; Feng, Y.; Weinar, W.R.; Luchetta, G.R.; Wu, Q., Ortiz–Ocasio, J.; Vinson, J.R.T.; Kramer, D.; and Porter, C., *J. Med. Chem.* (1994), 37:3464–3476.

Buchman, E.R.; Reiner, A.O.; Thurston, S.; Sheatter, M.J., *J. Am. Chem. Soc.* (1942), 64:2696–2700.

Cerecedo, L.R., and Pickel, F.D., Studies on Pyrimidines: I. The Preparation of 2–Methyl–6–oxypyrimidine–5–acetic Acid and Some of its Derivatives, Contribution from the Chemistry Department, Fordham University (1937) 59:1714–1716.

Fabiano, E., Golding, B.T., and Sadeghi, M.M., *Synthesis* (1987), 190–192.

Insaf, S.S., Danks, M.K., and Witiak, D., A Structure–Function Analysis of DNA Topoisomerase II Inhibitors, *Current Medicinal Chemistry*, (1996) 3:437–466.

Israel et al., *J. Med. Chem.* (1964), 7:710.

Miller, A.E.G., Biss, J.N., and Schwartzman, L.H., *J. Org. Chem.* (1959), 24:627.

Nagarajan, S. and Ganem, B., Chemistry of Naturally Occurring Polyamines. II. Unsaturated Spermidine and Spermine Derivatives, *J. Org. Chem.* (1987), 52:5044–46.

Pegg, A.E., Nagarajan, S., Naficy, S., and Ganem, B., Role of unsaturated derivatives of spermidine as substrates for spermine synthase and in supporting growth of SV–3T3 cells, Biochem. J. (1991), 274:167–171 (Printed in Great Britain).

Pharmaceuticals, Chiral, Reprinted from *Kirk–Othmer Encyclopedia of Chemical Technology*, Fourth Edition, vol. 18, ISBN 0–471–52587–8 (1996) by John Wiley & Sons, Inc.

Smirnov, I., Tiffany, K., Jackson, V., and Basu, H., Effects of Spermine and Its Cytotoxic Analogs on Nucleosome Formation on Relaxed and Supercoiled DNA In Vitro, *Biochemistry*, (1995).

* cited by examiner

Primary Examiner—Samuel Barts
(74) Attorney, Agent, or Firm—Joseph T. Leone, Esq.; DeWitt Ross & Stevens S.C.

(57) ABSTRACT

Compounds of Formula I:

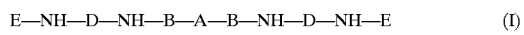

$$\text{E—NH—D—NH—B—A—B—NH—D—NH—E} \qquad (I)$$

wherein A is $C_2$–$C_6$ alkene, $C_3$–$C_6$ cycloalkyl, cycloalkenyl, or cycloaryl; B is independently a single bond, $C_1$–$C_6$ alkyl alkenyl; D is independently $C_1$–$C_6$ alkyl or alkenyl, or $C_3$–$C_6$ cycloalkyl, cycloalkenyl, or cycloaryl; and E is independently H, $C_3$–$C_6$ alkyl or alkenyl; and pharmaceutically-suitable salts thereof; a synthetic method therefor, pharmaceutical dosage forms containing one of more of these compounds, and use of these compounds in the treatment of neoplastic cell growth, are disclosed.

22 Claims, 20 Drawing Sheets

CONFORMATIONALLY RESTRICTED POLYAMINES

This is a continuation of application Ser. No. 08/951,015, filed on Oct. 15, 1997 now U.S. Pat. No. 5,889,061.

FIELD OF THE INVENTION

The present invention is directed to novel conformationally restricted polyamines and their use in the selective inhibition of neoplastic cell growth.

BIBLIOGRAPHY

Complete bibliographic citations to the references mentioned below are listed in the Bibliography, immediately preceding the claims. All of the references cited below are incorporated herein by reference in their entirety.

DESCRIPTION OF THE PRIOR ART

It has been known since the 1950's that conformation is a determinant in the spatial arrangement of functional groups, and that enzymes or drug receptors prefer specific ligand conformations or a specific distribution of conformations. This fruitful concept led to many decisive successes in drug design. A few examples will suffice to illuminate the subject.

The synthesis of conformationally constrained analogs of an inherently conformationally flexible substance such as acetyl choline helped to secure its "bioactive conformations," i.e., those conformers which are active at the muscarinic and nicotinic receptors. The trans-cyclopropyl analog of acetyl choline was shown to be preferred by the muscarinic receptor. Conformationally restricted analogs of dopamine, GABA, glutamic acid, histamine and serotonin have been obtained by introducing rigid rings into their structures. The constrained analogs have valuable chemotherapeutic effects.

The use of conformational restriction has also been very fruitful in the design of bioactive polypeptides. Polypeptides have so many flexible torsion angles that enormous numbers of conformations are possible in solution. The introduction of rings into the linear peptide chains reduces the number of conformations and has allowed the preparation of several biologically active substances. For instance, a cyclic hexapeptide possessing somatostatin activity is known.

Conformationally restricted enkephalin analogs are known, as are bicyclic lactam inhibitors (enalapril and enalaprilat) of the angiotensin converting enzyme.

Similar strategies have recently led to the development of a peptidomimetic benzodiazepine containing at least two conformational restrictions: a bicyclic heterocycle and an acetylene linker. The benzodiazepine is a non-peptide RGD (Arg-Gly-Asp) receptor antagonist.

The concept of conformational restriction led to the discovery that the bioactive conformation of the immunosuppressor cyclosporin A (CsA) only binds to cyclophylin A when the amide bond between the 9-position and 10-position residues in CsA is trans.

However, the prior art is silent regarding biologically active polyamines which are conformationally restricted by the introduction of one or more ring structures into the polyamine skeleton.

SUMMARY OF THE INVENTION

The present invention is directed to conformationally restricted polyamines of Formula I:

E—NH—D—NH—B—A—B—NH—D—NH—E       (I)

wherein A is selected from the group consisting of $C_2$–$C_6$ alkene and $C_3$–$C_6$ cycloalkyl, cycloalkenyl, and cycloaryl; B is independently selected from the group consisting of a single bond and $C_1$–$C_6$ alkyl and alkenyl; D is independently selected from the group consisting of $C_1$–$C_6$ alkyl and alkenyl, and $C_3$–$C_6$ cycloalkyl, cycloalkenyl, and cycloaryl; E is independently selected from the group consisting of H, $C_1$–$C_6$ alkyl and alkenyl; and pharmaceutically-suitable salts thereof.

The invention is also drawn to a method of synthesizing the Formula I compounds. Here, a compound of Formula II:

HO—B—A—B—OH       (II)

is reacted with with a protecting reagent, preferably mesitylenesulfonyl chloride, to yield a compound of Formula III:

PROT—O—B—A—B—O—PROT       (III)

wherein PROT is the protecting group.
Then, the Formula III compound is reacted with a compound of Formula IV:

E—N(PROT)—D—NH—PROT)       (IV)

to yield a compound of Formula V:

E—N(PROT)—D—N(PROT)—B—A—B—N(PROT)—D—
  N(PROT)—E       (V)

It is much preferred that the protecting group, PROT, in both the Formula III intermediate and the Formula IV intermediate be a mesitylenesulfonyl moiety.

The Formula V compound is then deprotected to yield a compound of Formula I.

The present invention is also drawn to pharmaceutical unit dosage forms containing one or more compounds of Formula I as described above in combination with a pharmaceutically-suitable carrier.

The present invention is also drawn to use of these novel conformationally restricted polyamines. These polyamines have utility as potent antineoplastic agents for use in mammals, including humans.

They also have utility as shape-restricted probes for the study of active-site geometry for enzyme and/or DNA interactions. Because the backbone of these molecules is conformationally restricted, they can only assume a very limited number of 3-dimensional shapes. By assessing the binding of these compounds to various enzyme active sites, or the their ability to interact with DNA, insight is gained into the particular spacial geometry required of enzyme agonists, antagonists and DNA binders. Both the compounds per se and their use is novel.

The present invention was inspired by a study of past failures in the use of polyamine compounds as chemotherapeutic agents in the treatment antiproliferative diseases. It is known that the polyamines spermidine and spermine are essential for normal cell growth. Potent antiproliferative agents have been developed which interfere with the biosynthesis of these compounds, thereby preventing cell proliferation. One of these agents, difluoromethylornithine (DFMO), is currently being studied in humans as a chemopreventive.

The therapeutic success of DFMO is, however, significantly marred by cellular uptake of exogenous polyamines via the polyamine transport system. Cellular uptake of polyamines from the extracellular milieu compensates for the endogenous depletion of the cellular polyamine pools due to the effects of DFMO. Since most food is rich in polyamines (e.g., 100 mL of orange juice contains approximately 400 ppm of putrescine, the spermine precursor), the antineoplastic effect of synthetic analogues which act by depleting the endogenous pool of polyamines is greatly diminished.

The present invention introduces a new approach for the use of polyamine analogs as agents for the treatment of cancer. Notably, both spermidine and spermine interact with DNA. These interactions induce structural changes in isolated DNA. Computer modeling and physico-chemical studies indicate that spermine induces conformational changes in defined DNA sequences. The presently described analogs of natural polyamines may interact with DNA differently than does spermine, resulting in the inhibition of tumor cell growth in culture.

In short, while not being bound to a particular mode of action, the present invention attacks the problem of unchecked cell proliferation by presumably changing DNA conformation via a polyamine analog/DNA interaction. The novel, conformationally restricted polyamines of the present invention display potent anti-proliferative activity.

Consequently, it is the principal aim of the present invention to provide novel, conformationally restricted compounds for use in the treatment of neoplastic cell growth.

These and other aims, objects, and advantages of the present invention will become clear upon a complete reading of the Detailed Description and claims, below.

DETAILED DESCRIPTION OF THE INVENTION

Figure 1:
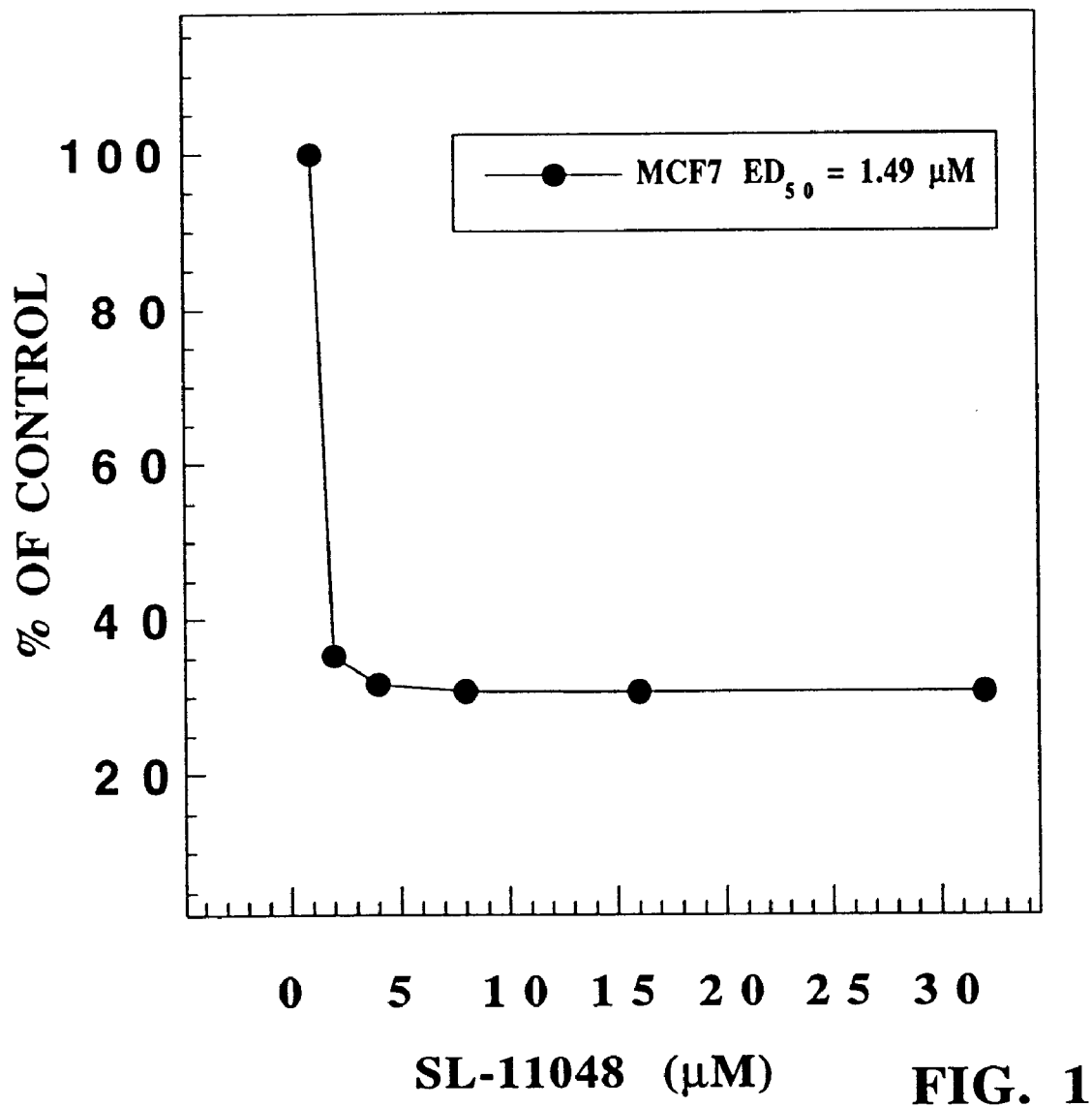
FIG. 1 is a graph depicting the in vitro effect of increasing concentrations of SL-11048 (Compound 57) on the survival of cultured breast cancer cells MCF7. $ED_{50}$=1.49 μM.

Reference is made throughout the Detailed Description to the various reaction Schemes and Tables included herein. For sake of clarity and brevity, reference numerals have been assigned to each unique chemical structure described. These reference numerals are used consistently throughout the disclosure to unambiguously designate the chemical entities discussed.

1. Conformationally Restricted Polyamines: Synthetic Approach

The manufacture of bioactive spermine ligands which may affect the structure of chromatin can be illustrated by the introduction of cyclopropyl and cyclobutyl constraints into the flexible spermine molecule. Spermine appears as follows:

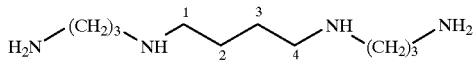

The first targeted location was the central 1,4-diaminobutane segment. In its staggered conformation, four semi-eclipsed conformational rotamers are possible around the diaminobutane segment. The four have enantiomeric relationships. Introduction of a bond between the C-1 and C-3 positions or the C-2 and C-4 positions of the central diaminobutane segment generates a cyclopropane ring. Introduction of an additional bond between the C-2 and C-3 positions generates a conformationally restricted alkene derivative. Cyclobutyl, cyclopentyl, and cyclohexyl moieties can be introduced into the structure following the same strategy.

Using this approach four conformationally semi-rigid structures were obtained which mimic the four semi-eclipsed conformational structures of spermine. Two of the semi-rigid structures are epimers of the other two.

For purposes of the present invention, it is important to note that the cis and trans isomers of the subject compounds assume very distinct three-dimensional conformations due to the restricted bond rotation afforded by the centrally-located ring structure or unsaturation. All geometric isomers (optically active or otherwise), including pure isolated cis forms and pure isolated trans forms of the subject compounds, and mixtures thereof, are explicitly within the scope of the present invention. Additionally, all positional isomers of the subject compounds are explicitly within the scope of the present invention. When A or D is a cyclical moiety, the two B substituents or the amino moieties, respectively, may be oriented in the 1,2 or 1,3 or 1,4 position with respect to each other.

(a) Spermine Analogs Containing a Cyclopropyl Ring

Cis and trans cyclopropyl analogs of spermine were prepared via the reactions illustrated in Schemes 1–5A.

With reference to Schemes 1 and 2, the cyclopropyl diesters 1 and 2 were first converted into their hydrazides 103 and 4, and the hydrazides converted into the diamines 5 and 6, respectively. The diamines 5 and 6 were then mesitylated to give the amides 7 and 8, and the amides were then alkylated with 9 to give 10 and 11, respectively. Hydrolysis of the protective groups yielded the trans analog 12 and the cis analog 13.

Referring now to Scheme 3, in a separate reaction, the trans cyclopropyl diester 1 was converted into the amide 14 by reaction with benzylamine (BnNH$_2$), the amide reduced to the amine 15, and the amine alkylated to 16. The phthalyl residues were then cleaved with hydrazine to give 17. Compound 17 was then either deprotected by hydrogenolysis to give 18; or fully alkylated to 19, and the benzyl residues cleaved by hydrogenolysis to give 20.

With reference to Scheme 4, the amine 15 was also alkylated with 21 to give 22. Compound 22 was then deprotected to yield the trans cyclopropyl analog 23.

An alternative (and preferred) route to 23 is given in Scheme 4A. Here, 3-ethylamino propionitrile 101 was converted into the corresponding amine 102, which was then mesitylated to yield 3. In a parallel synthesis, the cis diester 1 was reduced to the dialcohol 15', which was then mesitylated to yield the dimesityl derivative 16'. Reacting 3 and 16' in the presence of sodium hydride yields 22'. In the same fashion as Scheme 4, 22' was then deprotected to yield the trans cyclopropyl analog 23.

Referring now to Scheme 5, in a separate reaction, the cis cyclopropyl diester 2 was reduced to the dialcohol 24. The dialcohol was then converted into the amine 25, and the amine protected by mesitylation to 26. Compound 26 was then alkylated with 9 to yield 27, and then deprotected to yield the cis cyclopropyl tetramine 28.

An alternative (and preferred) route to 28 is given in Scheme 5A. Here, the cis cyclopropyl diester 2 is reduced to the dialcohol 24 in the same fashion as in Scheme 5. Compound 24 was then protected by mesitylation to yield 25'. Compound 25' was then reacted with 3 to yield 27. Deprotecting yields the tetramine 28.

SCHEME 1

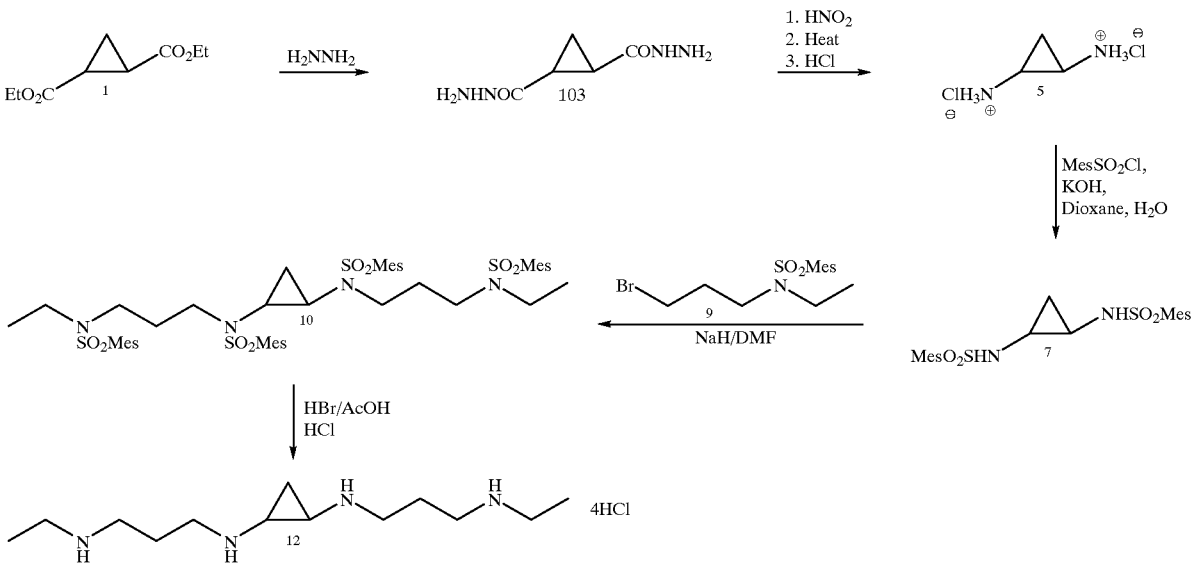

SCHEME 2
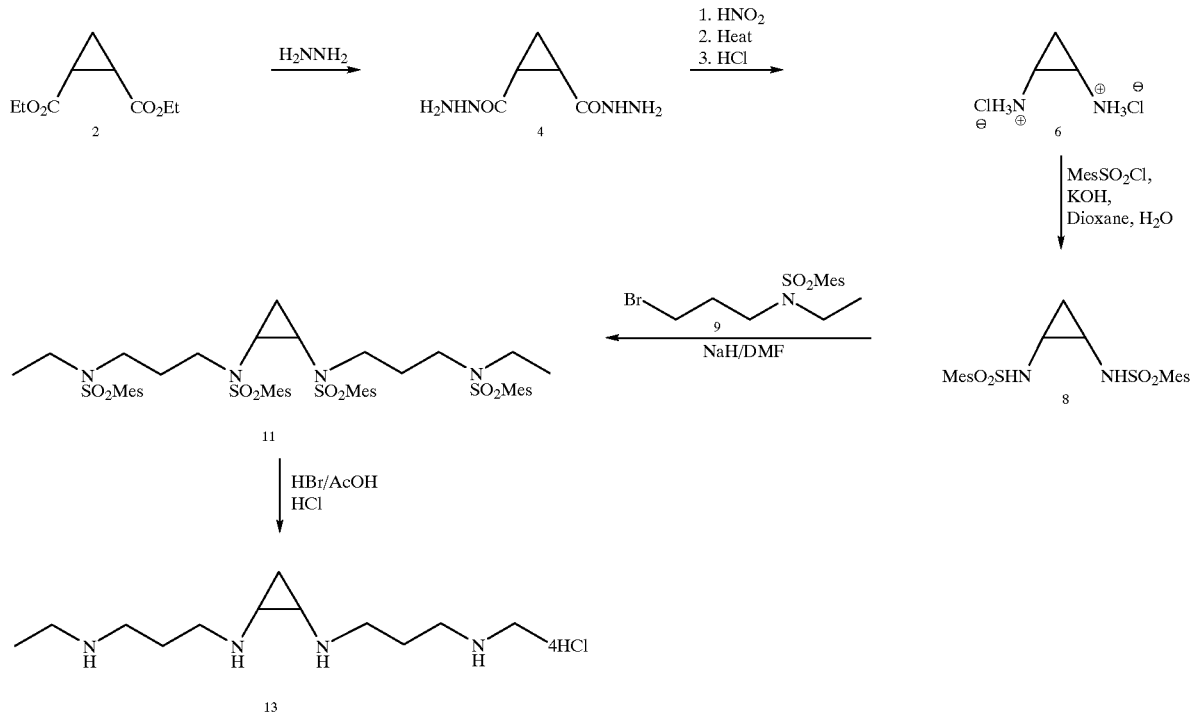
SCHEME 3
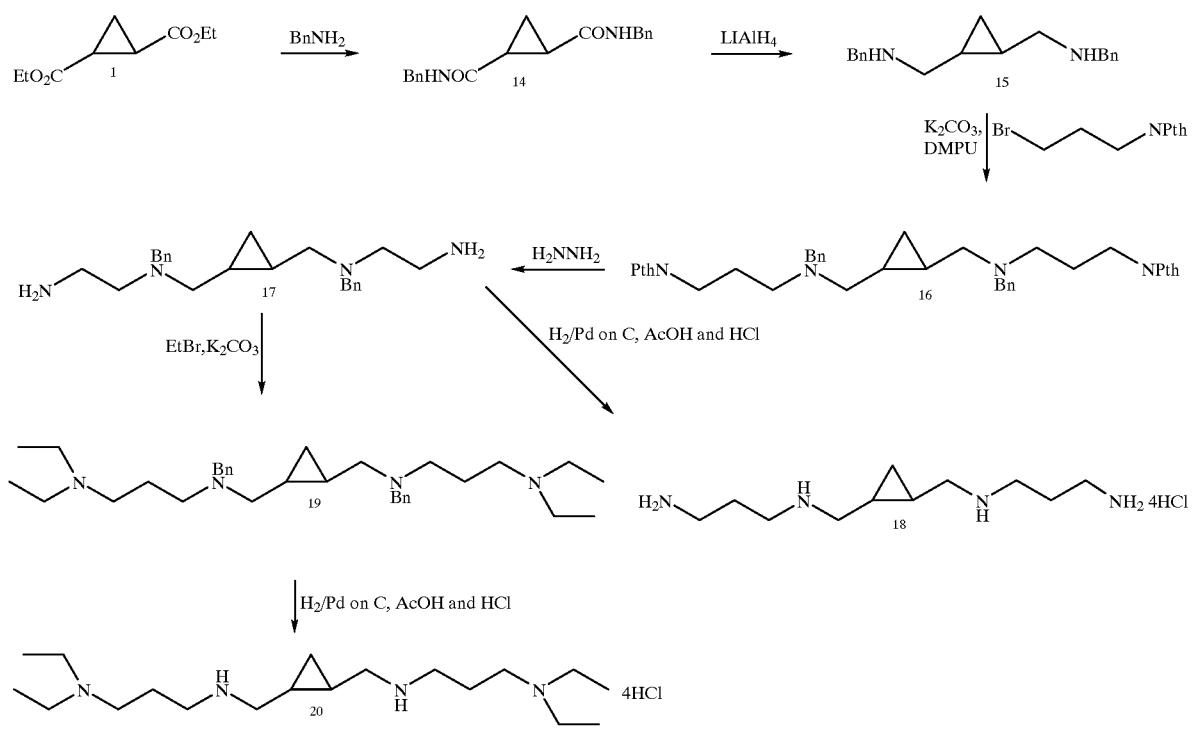

SCHEME 4
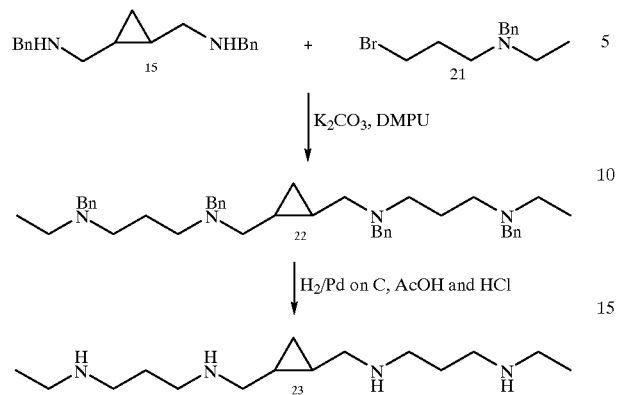

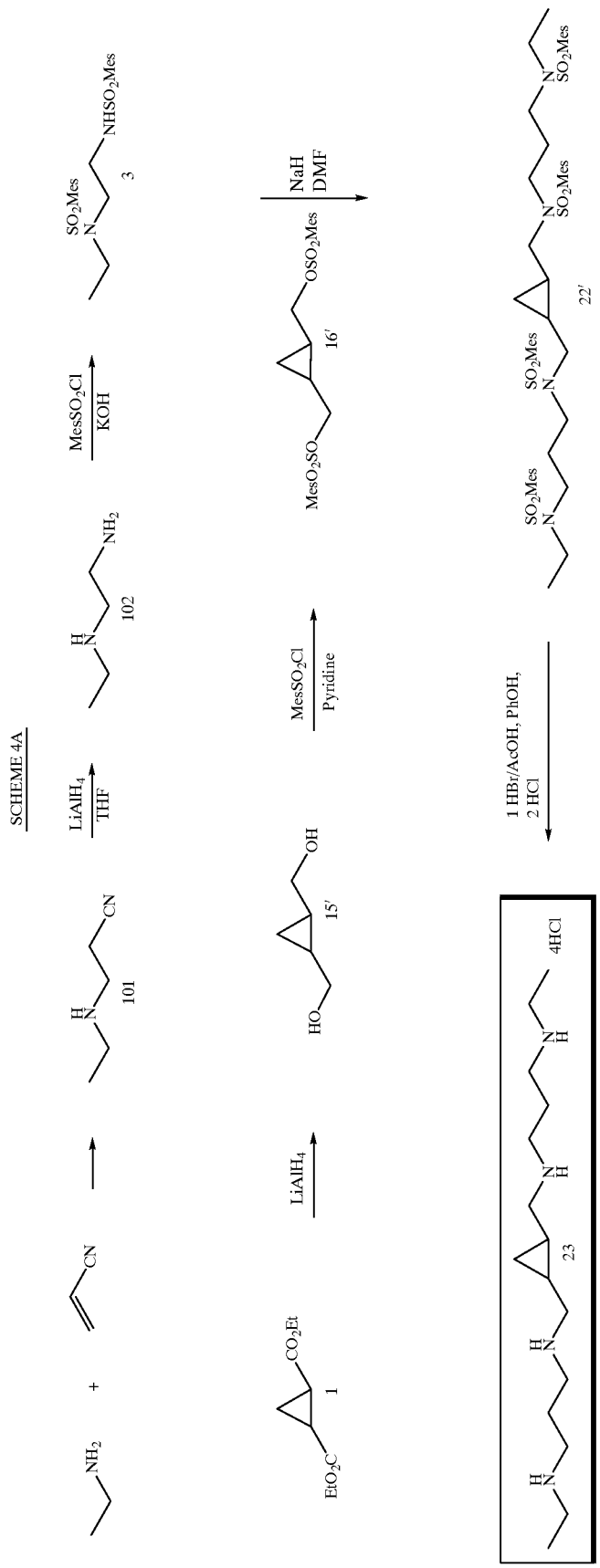

SCHEME 5

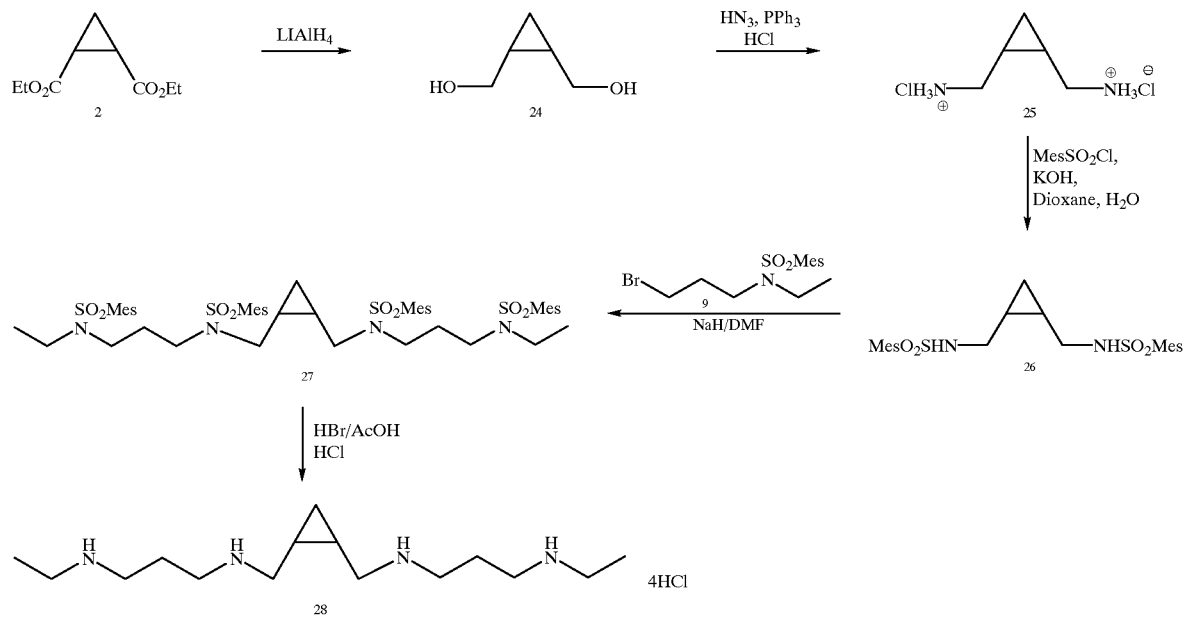

SCHEME 5A

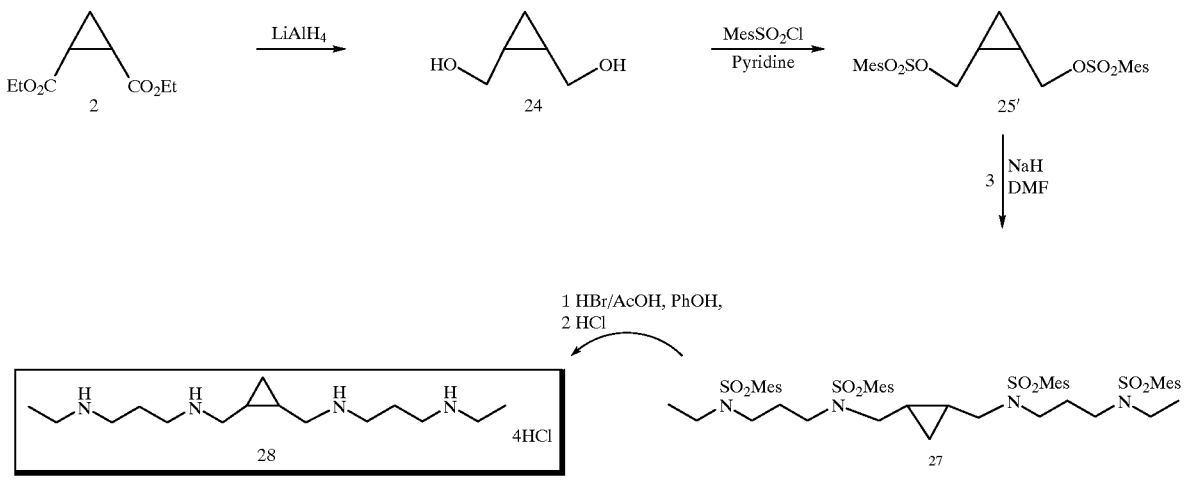

(b) Spermine Analogs Containing a Cyclobutyl Ring

Cis and trans cyclobutyl analogs of spermine were prepared via the reactions illustrated in Schemes 6–9A.

Referring now to Schemes 6 and 7, the synthesis of the cyclobutyl derivatives started with the trans and cis 1,2-diaminobutanes 29 and 30, respectively. These compounds were first converted to the amides 31 and 32, and then alkylated to 33 and 34, respectively. Compounds 33 and 34 were then deprotected to yield the trans tetramine 35 (Scheme 6) and the cis tetramine 36 (Scheme 7).

With reference to Schemes 8 and 9, in separate reactions, the trans cyclobutyl diester 37 and the cis cyclobutyl diester 38 were reduced to the respective dialcohols 39 and 40, the dialcohols converted into the diamines 41 and 42. The diamines 41 and 42 were then protected by mesitylation to yield 43 and 44, respectively. These compounds were then alkylated to give 45 and 46. The protecting groups were then removed to yield the trans cyclobutyl tetramine 47 (Scheme 8) and the cis tetramine 48 (Scheme 8).

Alternative (and preferred) routes to 47 and 48 are given in Schemes 8A and 9A, respectively. The cis and trans diesters 37 and 38 were reduced to the respective dialcohols 39 and 40 in the same fashion as in Schemes 8 and 9. Compounds 39 and 40 were then mesitylated to yield 41' and 42', respectively. Reaction of 41' and 42' with 3 yields 45 (Scheme 8A) and 46 (Scheme 9A). Deprotecting yields the desired products 47 and 48.
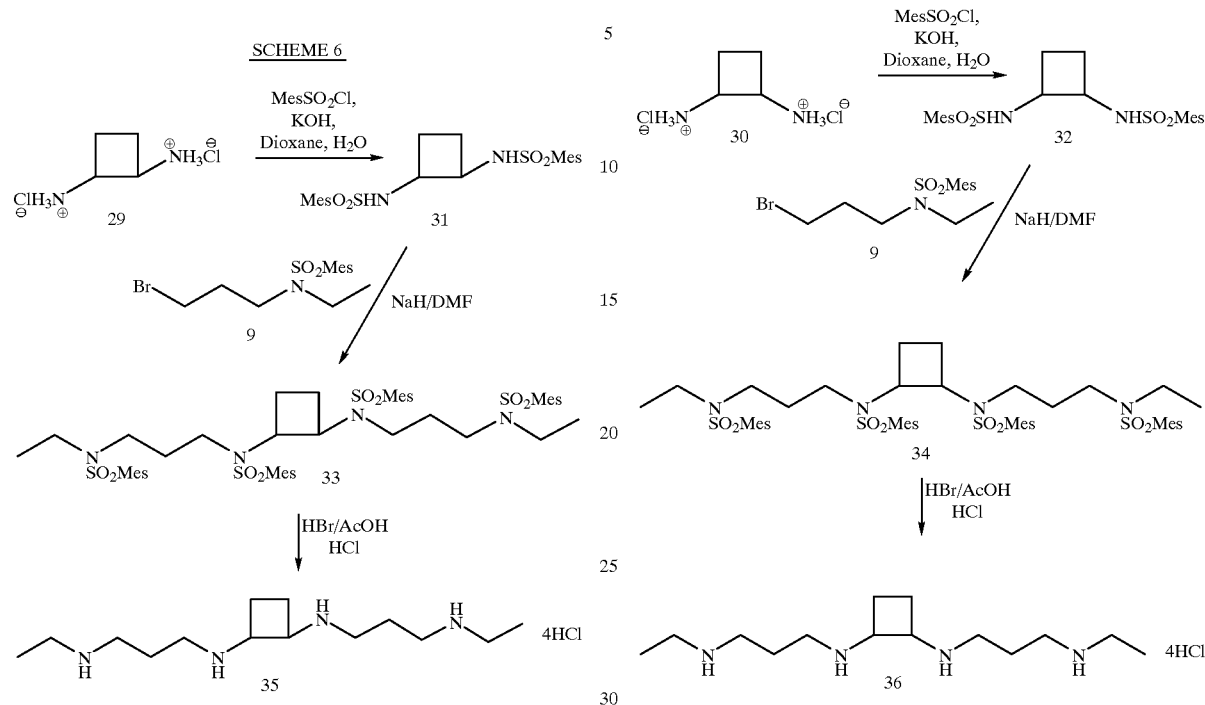
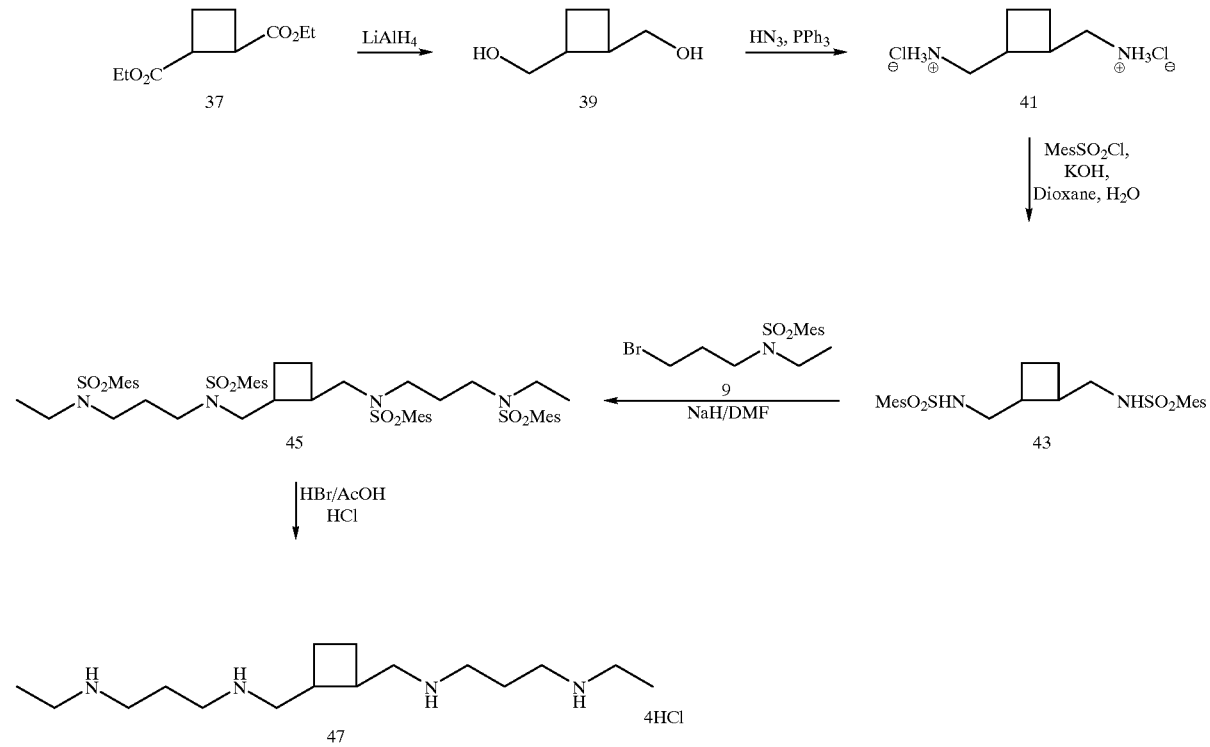

SCHEME 8A
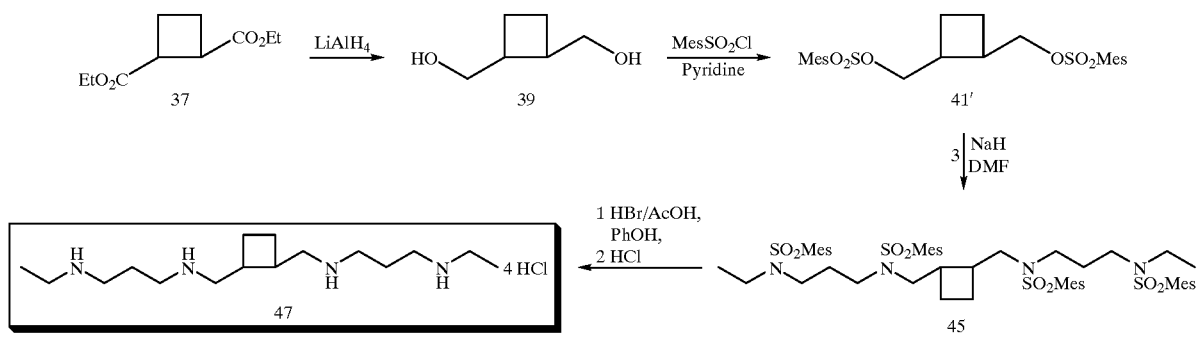
SCHEME 9
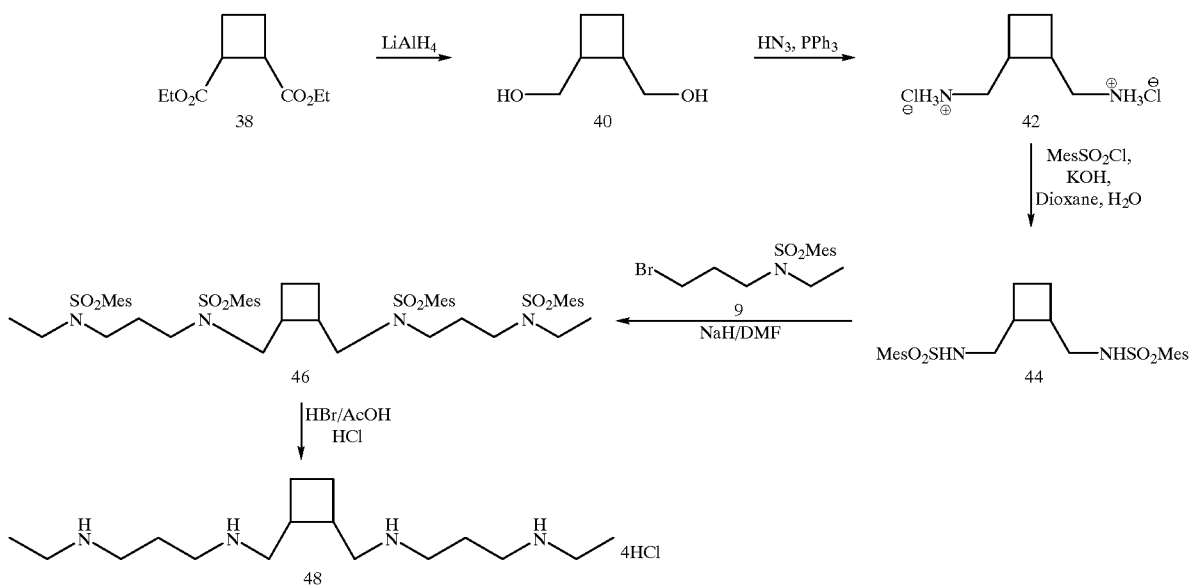
SCHEME 9A
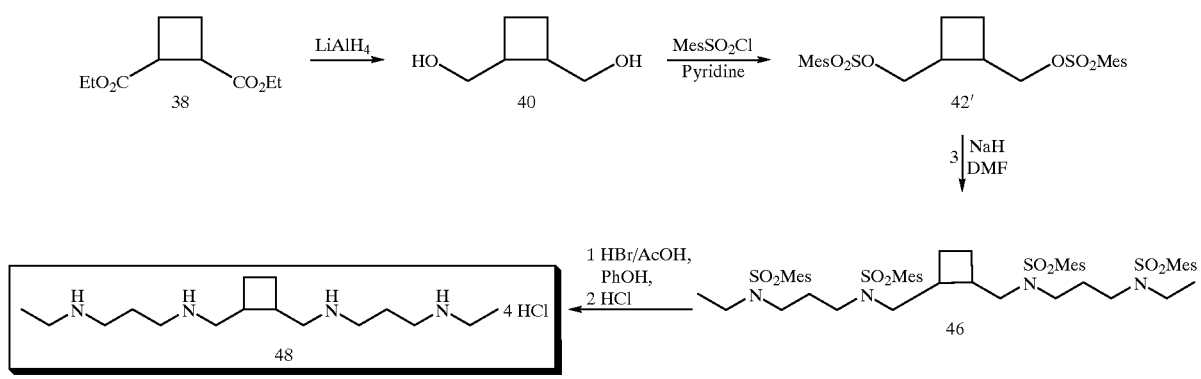

(c) Spermine Analogs Containing an Unsaturation

Cis and trans unsaturated analogs of spermine were prepared via the reactions illustrated in Schemes 10, 10A, 11, and 11A.

Referring to Scheme 10, the trans diester 49 was reduced to the dialcohol 50, which was then converted into the trans diamine 51. Referring to Scheme 11, the cis diamine 52 was obtained from the commercially available cis dialcohol 43'. With reference to both Scheme 10 and Scheme 11, compounds 51 and 52 were protected by mesitylation to give 53 and 54, respectively. Compounds 53 and 54 were alkylated to 55 and 56, and lastly deprotected to yield the trans tetramine 57 (Scheme 10) and the cis tetramine 58 (Scheme 11).

Alternative (and preferred) routes to 57 and 58 are given in Schemes 10A and 11A, respectively. The cis and trans dialcohols 50' and 50 were obtained in the same fashion as in Schemes 10 and 11. Compounds 50' and 50 were then mesitylated to yield 51' and 52', respectively. Reaction of 51' and 52' with 3 yields 55 (Scheme 10A) and 56 (Scheme 11A). Deprotecting yields the desired products 57 and 58.

Following the above general protocols, and using suitable and well known starting reagents, all of the compounds of Formula I, including those where A and D are independently $C_5$ or $C_6$ cycloalkyl, cycloalkenyl, or cycloaryl, can be readily obtained. An illustrative listing of compounds of Formula I are presented in Table 1.

See the Examples, below, for illustrative syntheses of the compounds shown in Table 1.

The pure compounds, as well as pharmaceutically-suitable salts thereof, are explicitly within the scope of the present invention. By the term "pharmaceutically-suitable salts" is meant any salt form of the subject compounds which renders them more amenable to administration by a chosen route. A wide range of such salts are well known to those of skill in the pharmaceutical art. The preferred pharmaceutically-suitable salts are acid addition salts such as chlorides, bromides, iodides and the like.

SCHEME 10

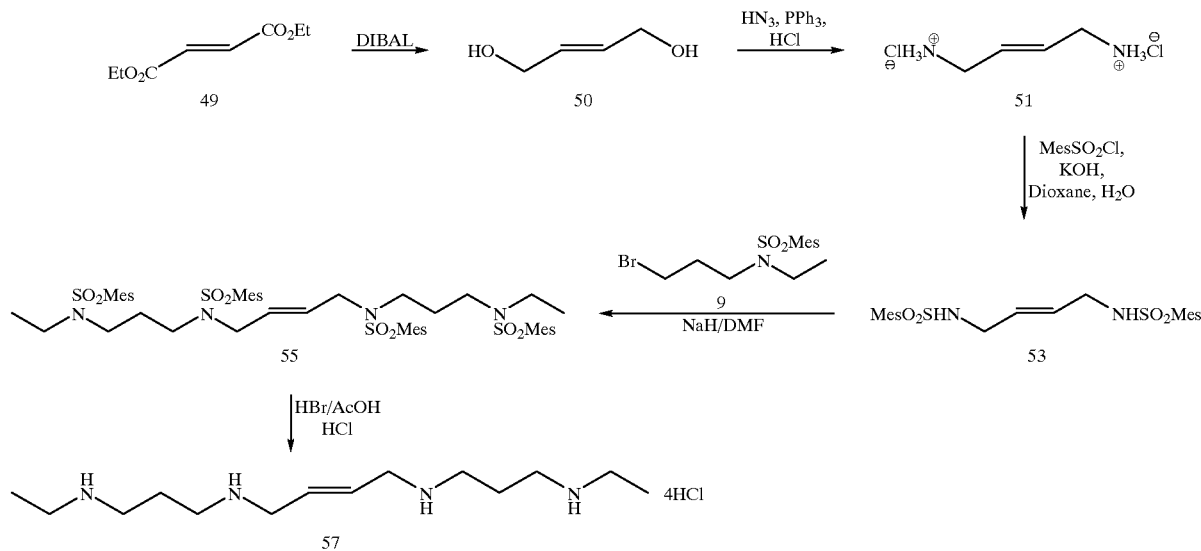

SCHEME 10A

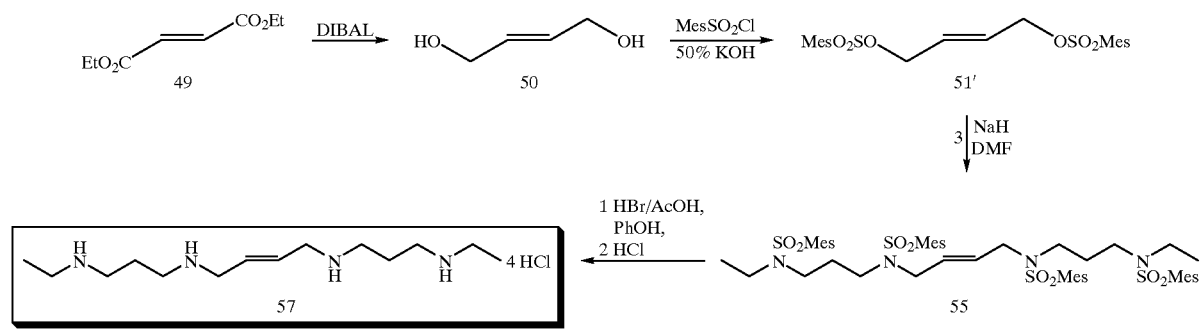

SCHEME 11
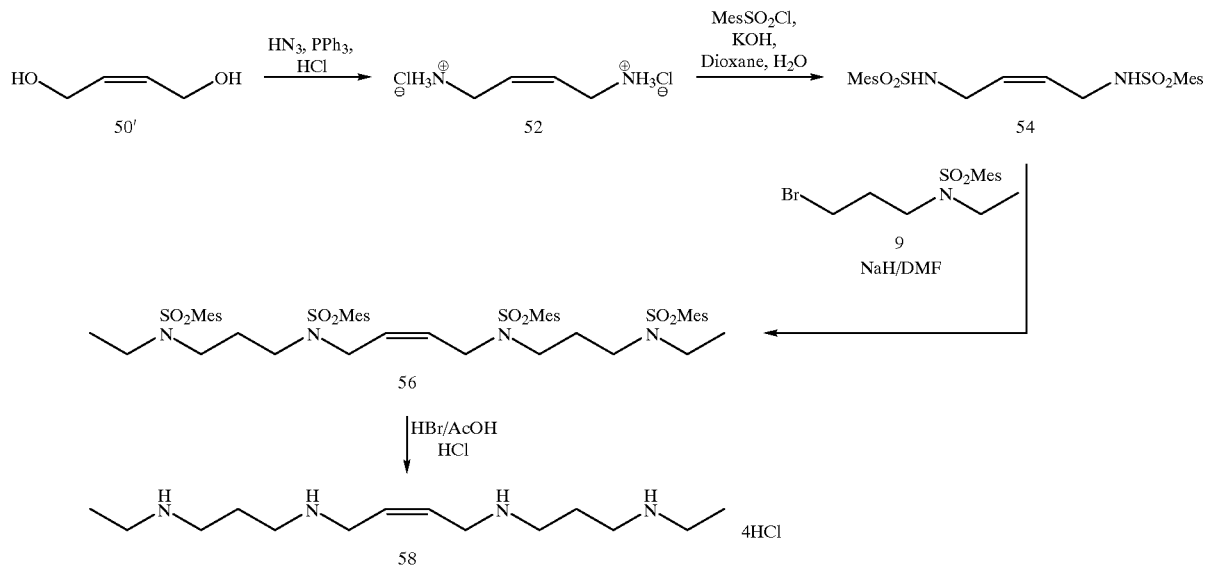
SCHEME 11A
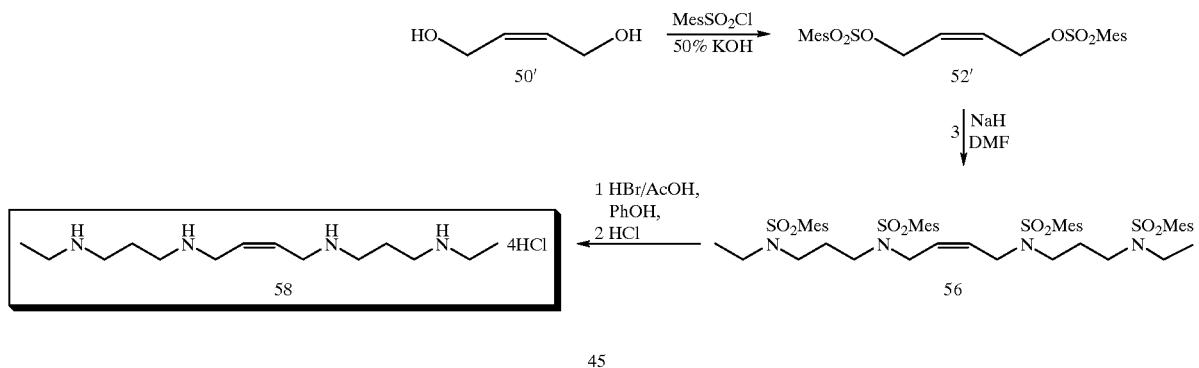
TABLE 1
| Compound No. | | |
|---|---|---|
| 12 | ![structure] | SL-11027 |
| 13 | ![structure] | SL-11033 |
| 23 | ![structure] | SL-11038 |

TABLE 1-continued

| Compound No. | | |
|---|---|---|
| 28 |  | SL-11037 |
| 35 |  | SL-11028 |
| 36 | 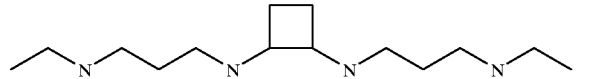 | SL-11034 |
| 47 | 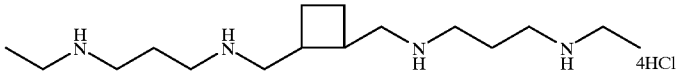 | LS-11044 |
| 48 | 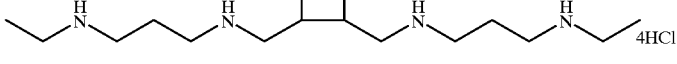 | SL-11043 |
| 57 | 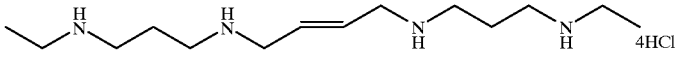 | SL-11048 |
| 58 | 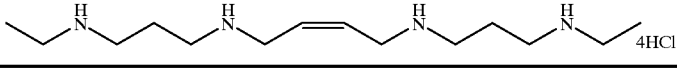 | SL-11047 |

2. Utility of the Conformationally Restricted Polyamines as Anti-Neoplastic Agents To assess the utility of the subject compounds in the treatment of neoplastic cell growth, the ability of the compounds to inhibit the in vitro growth of several commonly used cancer models was studied. The subject polyamines induce cell death in several neoplastic cell lines at drug concentrations smaller than 10 μM. In serial dilution, the restricted conformation polyamines of the present invention have been shown to inhibit cell growth and/or cause cell death in accepted in vitro test cultures for human breast cancer (MCF7), brain cancer (U251MG NCI), lung cancer (A549), colon cancer (HT29), and prostate cancer (PC3) at minute concentrations heretofore undescribed in the scientific literature.

The drawing figures are graphse depicting the results of a series of experiments which illustrate the ability of the subject polyamines to induce cell death in different neoplastic cell lines. These figures are described in detail in the Examples Section, below.

Referring to FIGS. 1–6, each of these graphs has as its X-axis the concentration of the particular compound being tested. The Y-axis of the graphs depicted in FIGS. 1–6 is a linear scale representing the fraction of cell survival in each of the cultures tested. Here, the neoplastic cell line MCF7 was used. This cell line is a human breast cancer cell line. These figures clearly illustrate the utility of the subject polyamines to inhibit the growth of human breast cancer. The 6 compounds whose in vitro activity is depicted in FIGS. 1–6 display $ED_{50}$ values ranging from 1.34 to 1.79 μM.

Figure 7:
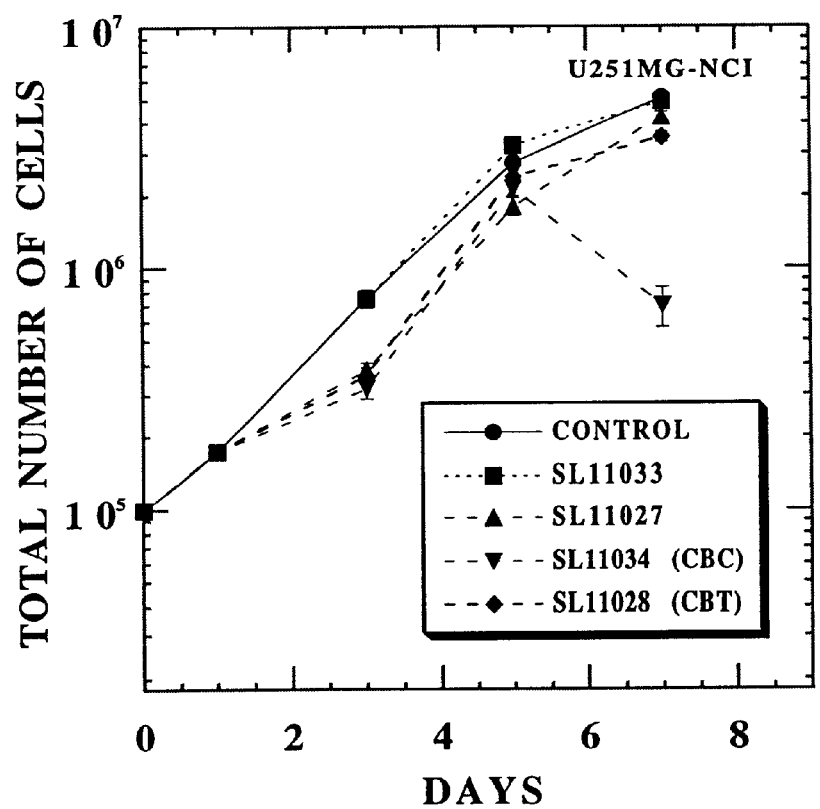
FIG. 7 is a graph depicting the in vitro effect of a 10 μM concentration of SL-11033 (13, ■), SL-11027 (12, ▲), SL-11034 (36, ▼), and SL-11028 (35, ♦) on the growth of brain cancer cells U251MG-NCI cells. Control=●.
Figure 8:
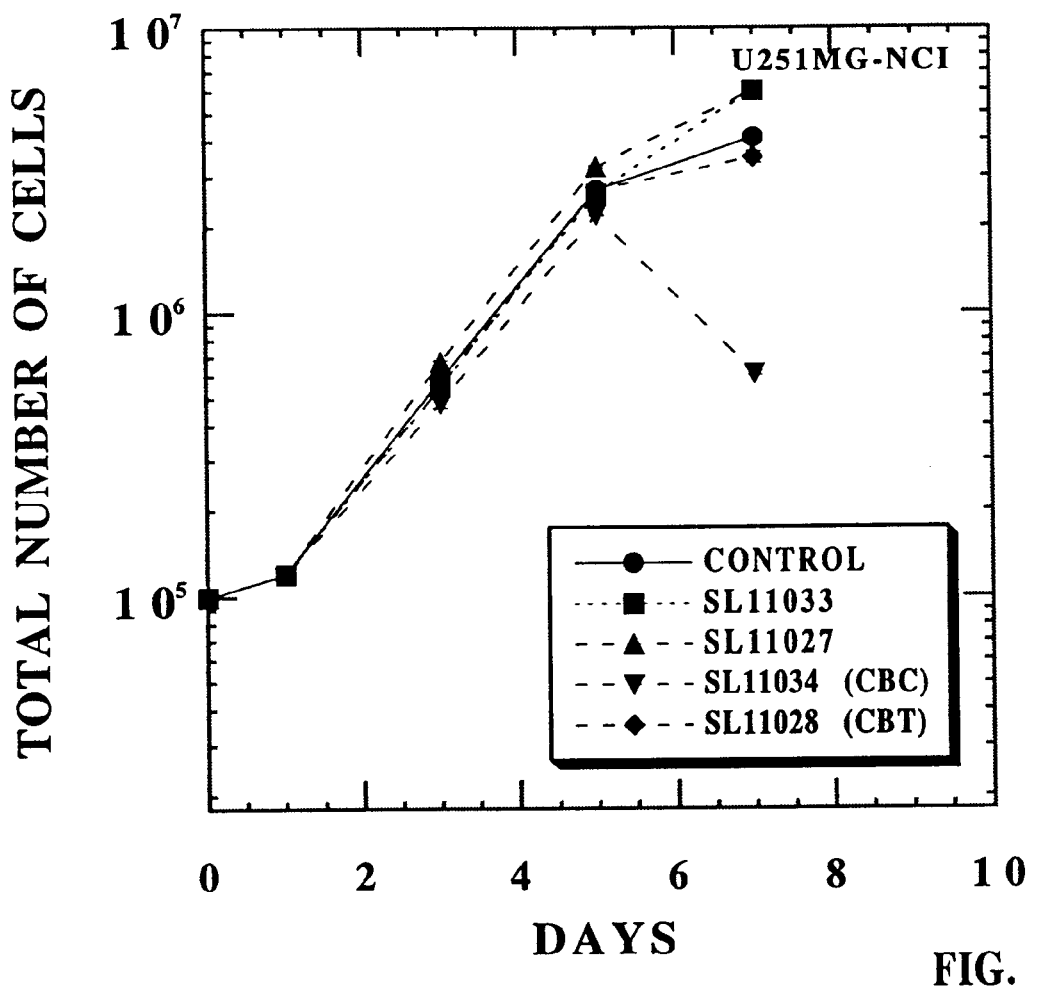
FIG. 8 is a graph depicting the in vitro effect of a 40 μM concentration of SL-11033 (13, ■), SL-11027 (12, ▲), SL-11034 (36, 569 ), and SL-11028 (35, ♦) on the growth of brain cancer cells U251MG-NCI cells. Control=●.

FIGS. 7 and 8 depict the effect of fixed doses of 10 μM and 40 μM of the subject compounds, respectively, on the growth of the human brain cancer cell line U251MG-NCI. Here, the X-axis represents time in days, and the Y-axis represents the total number of viable cells. FIGS. 7 and 8 further demonstrate the utility of subject compounds to inhibit neoplastic cell growth.

FIGS. 9A, 9B, 10A, 10B, 11A, and 11B show the in vitro effect of several of the subject compounds on HT29 cells. FIGS. 12A, 12B, 13A, 13B, 14A, and 14B show the in vitro effect of several of the subject compounds on U251 MG cells. FIGS. 15A, 15B, 16A, 16B, 17A, and 17B show the in vitro effect of several of the subject compounds on A 549 cells. Lastly, FIGS. 18A, 18B, 19A, 19B, 20A, and 21B show the in vitro effect of several of the subject compounds on PC 3 cells.

3. Administration and Pharmaceutical Unit Dosage Forms

The above-described compounds being effective to inhibit the growth of cancer cells, the compounds are suitable for the therapeutic treatment of neoplastic conditions in mammals, including humans. Cancer cell growth inhibition at pharmacologically-acceptable concentrations has been shown in human breast cancer, brain cancer, lung cancer, colon cancer, and prostate cancer cell lines.

Administration of the subject conformationally restricted polyaimes to a human or non-human patient can be accomplished by any means known. The preferred administration route is parenteral, including intravenous administration, intraarterial administration, intratumor administration, intramuscular administration, intraperitoneal administration, and subcutaneous administration in combination with a pharmaceutical carrier suitable for the chosen administration route. The treatment method is also amenable to oral administration.

It must be noted, as with all pharmaceuticals, the concentration or amount of the polyamine administered will vary depending upon the severity of the ailment being treated, the mode of administration, the condition and age of the subject being treated, and the particular polyamine or combination of polyamines being used.

The compounds described herein are administratable in the form of tablets, pills, powder mixtures, capsules, injectables, solutions, suppositories, emulsions, dispersions, food premixes, and in other suitable forms. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form may also contain non-toxic auxiliary substances such as emulsifying, preserving, or wetting agents, and the like.

Solid forms, such as tablets, capsules and powders, can be fabricated using conventional tabletting and capsule-filling machinery, which is well known in the art. Solid dosage forms may contain any number of additional non-active ingredients known to the art, including excipients, lubricants, dessicants, binders, colorants, disintegrating agents, dry flow modifiers, preservatives, and the like.

Liquid forms for ingestion can be formulated using known liquid carriers, including aqueous and non-aqueous carriers, suspensions, oil-in-water and/or water-in-oil emulsions, and the like. Liquid formulation may also contain any number of additional non-active ingredients, including colorants, fragrance, flavorings, viscosity modifiers, preservatives, stabilizers, and the like.

For parenteral administration, the subject compounds may be administered as injectable dosages of a solution or suspension of the compound in a physiologically-acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers.

The pharmaceutical unit dosage chosen is preferably fabricated and administered to provide a concentration of drug at the point of contact with the cancer cell of from 1 $\mu$M to 10 mM. More preferred is a concentration of from 1 to 100 $\mu$M. This concentration will, of course, depend on the chosen route of administration and the mass of the subject being treated.

EXAMPLES

Chemical Synthesis Examples

The following Examples are an illustrative, not exclusive, listing of the manufacture of several compounds according to the present invention. The Examples are included herein solely to aid in a more complete understanding of the present invention. The Examples do not limit the invention disclosed and claimed herein in any fashion. Reference numerals are to the Reaction Schemes described above.

All melting points are uncorrected. NMR spectra were recorded on 300 MHz spectrometer with TMS as internal standard. Purification of the products was carried out using silica gel 60 (230–400 mesh) and the appropriate solvent system. HPLCs were run on a Waters 8×10 "NOVAPAK" cartridge (Millipore Corporation, Marlboro, Mass.) using reverse phase and a gradient of acetonitrile and sodium acetate buffer, pH 4.5.

Compounds 1 and 2 were prepared according to the method of Ashton et al. (1988).

Compound 1: $^1$HNMR (CDCl$_3$): δ1.26 (t, J=7 Hz, 6H, CH$_2$CH$_3$), 1.43 (dd, J=7.0, 8.0 Hz, 2H, CyPrCH$_2$), 2.16 (dd, J=7.0, 8.0 Hz, 2H, CyPrCH), 4.16 (q, J=7 Hz, 4 H, CH$_2$CH$_3$). $^{13}$C-NMR (CDCl$_3$): 14.12, 15.25, 22.31, 61.01, 171.75.

Compound 2: $^1$HNMR (CDCl$_3$): δ1.25 (m, 1H, CyPrCH$_2$), 1.26 (t, J=7 Hz, 6H, CH$_2$CH$_3$), 1.70 (ddd, J=5.0, 6.0, 5.5 Hz, 1H, CyPrCH$_2$), 2.06 (dd, J=6.0, 9.0 Hz, 2H, CyPrCH), 4.17 (q, J=7 Hz, 4H, CH$_2$CH$_3$).

Compound 103: To a solution of ethyl ester 1 (3.5 mL, 20 mmol) in ethanol (10 mL) was added hydrazine monohydrate (3.38 mL, 80 mmol). The mixture was heated to reflux overnight to afford 103 as a white solid. The reaction was cooled to room temperature (RT), diluted with 20 mL CHCl$_3$, and the solid was filtered. Yield=80%; m.p. 215–217° C.; $^1$HNMR (D$_2$O): δ1.35 (dd, J=7.0, 8.0 Hz, 2H, CyPrCH), 2.04 (dd, J=7.0, 8.0 Hz, 1H, CyPrCH); $^{13}$C-NMR (D$_2$O): 15.5, 24, 176.

Compound 4: This compound was synthesized via the route described above for compound 103. Yield was 87%; m.p. 196–198° C.; $^1$HNMR (D$_2$O): δ1.25 (m, 1H, CyPrCH$_2$), 1.45 (ddd, J=5.0, 6.0, 5.5 Hz, 1H, CyPrCH$_2$), 2.05 (dd, J=6.0, 9.6 Hz, 2H, CyPrCH); $^{13}$C-NMR (D$_2$O): 12.97, 23.88, 175.0.

Compound 5: Concentrated HCl was placed into a 125 mL conical flask and 9 g of crushed ice added thereto. Compound 103 (1.58 g, 10 mmol) was dissolved in this solution and then ethyl ether (10 mL) was added. While maintaining the temperature below 10° C., a NaNO$_2$ solution (1.73 g, 25 mmol in 4 mL H$_2$O) was added slowly. The organic layer was separated, the aqueous layer extracted with ether (3×20 mL), and the organic fractions combined and dried over CaCl$_2$. The ether solution was filtered into a 250 mL round bottom flask and diluted with anhydrous toluene (30 mL). Ether was distilled-off using a fractionating column condenser. The remaining toluene solution was heated to 85° C. until the evolution of nitrogen ceased. Stirring at 85° C. was continued for and additional 10 min. While still hot, this solution was poured into preheated (60° C.) concentrated HCl (8 mL). Toluene was distilled off under vaccuum and anydrous ethanol (15 mL) was added to the flask and then distilled-off. This process was repeated twice to afford a cream-colored solid, which was digested with ethanol and suction-filtered to afford 0.645 g (45%) of pure 5; m.p. 220° C. (dec); $^1$HNMR (D$_2$O) δ1.53 (t, J=6.0 Hz, 2H), 3.2 (t, J=6.0 Hz, 2H).

Compound 6: This compound was synthesized in the same manner as 5. Yield was 58%; m.p. 220° C.; $^1$HNMR (D$_2$O) δ1.25 (m, 2H, CyPrCH$_2$), 2.9 (dd, 2H, J =6.0, 8.0 Hz, CyPrCH).

Compound 7: Compound 5 (145 mg, 1 mmol) was dissolved in 4 mL of dioxane/water (1:1), while maintaining a pH ca. 11 by the addition of 5% KOH. Mesitylenesulfonyl chloride (875 mg, 4 mmol) in 5 mL dioxane was then added slowly. The upper layer of the mixture was carefully decanted and the gummy residue was triturated with hexanes to afford 330 mg (76%) of 7 as a white solid, which was recrystalized from CHCl$_3$/hexanes. m.p. 189–191° C.; $^1$HNMR (CDCl$_3$): δ0.9 (t, J=8.0 Hz, 2H CyPrCH$_2$), 2.24 (t, J=8 Hz, 2H, CyPrCH), 2.30 (s, 6H, 2 CH$_3$), 2.55 (s, 12H, 4 CH$_3$), 5.00 (s, 2H, NH), 6.75 (s, 4H, aromatic); $^{13}$C-NMR (CDCl$_3$): 14.16, 20.98, 22.92, 30.92, 132.11, 132.89, 139.20, 142.79; MS (m/z): 436.53 (M$^+$), 421, 253, 183, 171, 119, 91; Anal: C$_{21}$H$_{28}$N$_2$S$_2$O$_4$.

Compound 8: This compound was synthesized in the same manner as 7. Yield was 95%; mp 175–177° C.; $^1$HNMR (CDCl$_3$): δ0.80 (m, 1H, CyPrCH$_2$), 0.95 (m, 1H, CyPrCH$_2$), 2.25 (m, 2H, CyPrCH), 2.34 (s, 6H, 2 CH$_3$), 2.65 (s, 12H, 4 CH$_3$), 5.25(br, 2H, NH), 7.00 (s, 4H, aromatic); $^{13}$C-NMR (CDCl$_3$): 13.5, 20.96, 22.96, 28.00, 132.08, 133.00, 139.45, 142.09.

Compound 10: This compound was synthesized by the procedure of Bergeron et al. (1994). NaH (95%, 0.111 g, 4.4 mmol) was added to 7 (0.872 g, 2 mmol) in anhydrous dimethylformamide (40 mL) at 0° C. The mixture was stirred for 30 min at 0° C. Compound 9 (1.531 g, 4.4 mmol) in anydrous DMF (50 mL) was added slowly, stirred for another 15 min. at 0° C. and then stirred overnight at room temperature. The reaction was quenched with water (8 mL), followed by extraction with ether (3×25 mL). The combined organic layers were washed with water (4×30 mL) and brine (2×25 mL). The solvents were removed under vacuum to afford a gum, which was filtered on a silica gel column using 8:1 hexanes:ethylacetate as an eluant. Obtained was 1.7 g (77%) of 10 as a white solid. m.p. 60–6° C.; $^1$HNMR (CDCl$_3$) δ0.57 (dd, J=6 and 8 Hz, 2H, CyPrCH$_2$), 0.99 (t, J=8 Hz, 6 H, 2 CH$_3$), 1.7–1.9 (m, 4H, NCH$_2$CH$_2$), 2.25 (s, 6H, 2 CH$_3$), 2.29 (s, 6H, 2 CH$_3$), 2,50 (s, 12H, 4 CH$_3$), 2.55 (s, 12 H, 4 CH$_3$), 2.56–2.67 (m, 2H, CyPrCH), 2.87–3.19 (m, 12H, 6 NCH$_2$), 6.86 (s, 4H, aromatic), 6.90 (s, 4H, aromatic); MS (m/z) 971.4 (M$^+$), 787.3, 605.3, 295.1, 183, 119.1 (100%); Anal: (C$_{49}$H$_{70}$N$_4$S$_4$O$_8$).

Compound 11: This compound was obtained (29%) from 7 as described above for compound 10. mp=74–75° C.; $^1$HNMR (CDCl$_3$) δ0.25–0.36 (m, 1H, CyPrCH$_2$), 0.99 (t, J=8 Hz, 6H, 2CH$_3$, 1.00–1.11 (m, 1H, CyPrCH$_2$), 1.50–1.70 (m, 4H, NCH$_2$CH$_2$), 2.30 (s, 12H, 4CH$_3$), 2.55 (s, 12H, 4CH$_3$), 2.58 (s, 12H, 4CH$_3$), 2.56–2.70 (m, 2H, CyPrCH), 2.90–3.20 (m, 12H, 6NCH$_2$), 6.90 (s, 4H, aromatic), 6.93 (s, 4H, aromatic). MS (m/z) 971.4 (M$^+$), 787.3, 605.3, 154 (100%), 119. Anal (C$_{49}$H$_{70}$N$_4$S$_4$O$_8$).

Compound 12: This compound was synthesized by the procedure of Bergeron et al. (1994) in 77% yield. Recrystallized from EtOH, mp=240° C. (dec.); $^1$HNMR (D$_2$O Acetone-d$_6$) δ1.23 (t, J=6.8, 2H, CyPrCH$_2$), 1.31 (t, J=7.3 Hz, 6H, 3CH$_3$), 2.00–2.10 (m, 4H, NCCH$_2$), 2.81 (t, J=6.6 Hz, 2H, CyPrCH), 3.00–3.20 (m, 12H, 6 NCH$_2$), $^{13}$C-NMR (D$_2$O, Acetone-d$_6$) δ13.33, 13.73, 26.64, 37.63, 45.76, 47.27, 47.83; MS (m/z) 243.4 (M$^+$, 100%), 163.3, 141.3.

Compound 13: This compound was obtained from 11 in 28% yield, mp=240° C. (dec.) $^1$HNMR (D$_2$O/Acetone-d$_6$) δ0.72–0.81 (m, 1H, CyPrCH$_2$), 1.16 (ddd, J=7.2, 8.1, 7.2 Hz, 1H, CyPrCH$_2$), 1.29 (t, J=7.4 Hz, 6H, 2CH$_3$), 2.04 (Pent. J=7.5 Hz, 4H, NCCH$_2$), 2.69 (t, J=6.8, 7.4 Hz, 2H, CyPrCH), 2.98–3.24 (m, 12H, NCH$_2$); $^{13}$C-NMR (D$_2$O, Acetone-d$_6$) δ12.44, 13.43, 27.12, 35.86, 45.89, 47.48, 48.06; MS (m/z):243.3 (M$^+$, 100%). 163.2, 142.7.

Compound 14: Compound 1 (3.5 mL, 20 mmol) was dissolved in toluene (30 mL) and benzylamine (4.61 mL, 44 mmol) was added to the solution. The mixture was stirred overnight at 80° C. to afford 14 as white solid which was filtered and washed with EtOH, yield 85%; mp=237–238° C.

Compound 15: LiAlH$_4$ (200 mg, 5.26 mmol) was suspended in anhydrous THF (10 mL) and kept under argon. Compound 14 (500 mg, 1.62 mmol) was added to the suspension in portions. Though 14 was insoluble at RT, it was slowly dissolved while refluxing overnight. The reaction was quenched with MeOH and the solvents were evaporated under vacuum to dryness. The residue was then extracted with CHCl$_3$ (2×15 mL). The organic layer was cooled on an ice-salt mixture to precipitate by-products which were filtered off. CHCl$_3$ was then removed under vacuum to afford 15. It was purified by column chromatography using silica gel and 5:1 hexanes:ethylacetate as an eluant. This gave 45% of 15 as a thick gum. $^1$HNMR (CDCl$_3$) δ0.36 (dd, J=7.7, 7.2 Hz, 2H, CyPrCH$_2$). 0.84 (t, J=7.7 Hz, 2H, CyPrCH), 1.91 (br, 2H, NH), 2.44–2.60 (m, 4H, 2NCH$_2$), 3.81 (s, 4H, Benzyl), 7.30 (s, 10H, aromatic); $^{13}$C-NMR (CDCl$_3$) δ15.27, 39.12, 53.46, 126.93, 128.20, 128.41, 140.42.

Compound 16: Compound 15 (4.5 g, 16.1 mmol) was dissolved in dimethylpropyleneurea (DMPU) (35 mL), and K$_2$CO$_3$ (8.95 g, 64.8 mmol) was added, followed by 3-bromopropylphthalimide (8.67 g, 32.3 mmol) in DMPU (15 mL) and the solution was stirred at 110° C. overnight. The solution was then cooled to 0° C., and the precipitated solids were dissolved in H$_2$O (50 mL). The mixture was extracted with ether (3×50 mL), the organic layers were washed with water (3×25 mL), dried (MgSO$_4$), and evaporated in vacuo to afford a thick gum. This gum was subjected to column chromatography on silica gel column using hexanes:ethylacetate (7:3) as an eluant to give 6.1 g (58%) of 16. $^1$HNMR (CDCl$_3$) δ0.31 (dd, J=6.4, 6.8 Hz, 2H, CyPrCH$_2$), 0.66 (t, J=5.8 Hz, 2H, CyPrCH), 1.83 (Pent.), J=7.0 Hz, 4H, NCCH$_2$), 2.35 (dq$_{(AB)}$, J=6.3, 13.2 Hz, 4H, NCH$_2$), 2.56 (t, J=7.0 Hz, 4H, 2NCH$_2$), 3.60 (s, 4H, Benzyl), 3.69 (t, J=7.4 Hz, 4H, NCH$_2$), 7.1–7.4 (m, 10H, aromatic), 7.65–7.85 (m, 8H, aromatic); $^{13}$C-NMR (CDCl$_3$) δ11.10, 15.24, 26.01, 36.43, 50.82, 57.48, 58.37, 123.10, 126.67, 128.10, 128.77, 132.22, 133.78, 139.80, 168.36.

Compound 17: Compound 16 (5.86 g, 8.96 mmol) was dissolved in methanol (100 mL) and hydrazine monohydrate (3.6 mmol) was added and the mixture was heated to reflux overnight. The methanol was evaporated under vacuum, and NH$_4$OH (4M, 100 mL) added to the residue. This solution was extracted vigorously with CHCl$_3$ (4×50 mL), the combined organic layers dried (MgSO$_4$), and CHCl$_3$ evaporated to afford essentially pure 17 as a thick gum (3.3 g, 94% yield); $^1$HNMR (CDCl$_3$) δ0.34 (dd, J=6.4, 6.8 Hz, 2H, CyPrCH$_2$), 0.68 (t, J=5.8 Hz, 2H, CyPrCH), 1.62 (pent., J=6.8 Hz, 4H, NCCH$_2$), 1.70 (br, 4H, NH$_2$), 2.35 (dq$_{(AB)}$, J=6.1, 13.2 Hz, 4H, NCH$_2$), 2.51 (t, J=6.8 Hz, 4H, NCH$_2$), 2.69 (t, J=6.7 Hz, 4H, NCH$_2$), 3.60 (s, 4H, Benzylic), 7.2–7.39 (m, 10H, aromatic); $^{13}$C-NMR (CDCl$_3$) δ11.09, 15.54, 30.72, 40.49, 51.18, 57.77, 58,62, 126.75, 128.16, 128.76, 140.05.

Compound 18: Compound 17 (0.5 g, 1.27 mmol) was dissolved in acetic acid (10 mL), To this solution was added 10% Pd on activated carbon (200 mg) and the mixture was hydrogenated overnight at 60° C. The catalyst was filtered off and 1M HCl in ether (10 mL) was added to the solution to afford a white solid, which was filtered and recrystallized from MeOH/ether to give 0.210 g (46%) of 18. mp=270° C. (dec.); $^1$HNMR ((D$_2$O) δ0.84 (dd, J=6.7, 7.1 Hz, 2H, CyPrCH$_2$), 1.20 (t, J=6.5 Hz, 2H, CyPrCH), 2.00–2.20 (m, 4H, NCCH$_2$), 2.05–2.90 (m, 2H, NCHH), 3.00–3.25 (m, 10H, NCH$_2$); MS (m/z) 215.1 (M$^+$, 100%), 144.9, 132, 124, 98.

Compound 19: Compound 17 (1.5 g, 3.8 mmol) was dissolved in DMPU (10 mL) and K$_2$CO$_3$ (1.52 g, 10.98 mmol) added to the solution, followed by the addition of ethylbromide (0.56 mL, 7.6 mmol). The flask was fitted with a dry-ice reflux condensor, then stirred overnight at 45° C. The mixture was then cooled to 0° C., and the precipitated solids were dissolved in $H_2O$ (100 mL), extracted with ether (3×100 mL), the combined organic layers washed with $H_2O$ (3×50 mL), dried ($MgSO_4$), and the solvent evaporated to afford a thick gum. The gum was purified by column chromatography over silica gel using ethyl acetate as an eluant (95% yield). $^1$HNMR ($CDCl_3$) δ0.33 (dd, J=6.5, 7.0 Hz, 2H, $CyPrCH_2$), 0.65 (t, J=6.5 Hz, 2H, CyPrCH), 1.00 (t, J=7.2 Hz, 12H, $4CH_3$), 1.55–1.69 (m, 4H, $NCCH_2$), 2.25 (dd, J=6.3, 13.2 Hz, 2H, $NCH_2$), 2.30–2.55 (m, 18H, $NCH_2$), 3.62 (s, 4H, benzyl), 7.19–7.35 (m, 10H, aromatic).

Compound 20: This compound was obtained as described above for 18 starting from 19 (80% yield). mp=230° C. (dec); $^1$HNMR ($D_2O$) δ0.90 (t, J=6.8 Hz, 2H, $CyPrCH_2$), 1.22 (t, J=6.5 Hz, 2H, CyPrCH), 1.33 (t, J=7.3 Hz, 12H, $4CH_3$), 3.15–3.35 (m, 4H, $NCCH_2$), 2.95 (dd, J=8, 13 Hz, $NCH_2$), 3.15–3.35 (m, 18H, $NCH_2$); $^{13}$C-NMR ($D_2O$) δ11.83, 13.66, 17.30, 24.35, 47.77, 51.18, 52.05, 54.46; MS (m/z) 327 ($M^+$, 100%).

Compound 22: Compound 22 was prepared as described above for 16, using 15 as the reactant (51% yield). $^1$HNMR ($CDCl_3$) δ0.65 (t, J=6.8 Hz, 2H, $CyPrCH_2$), 0.90–1.1 (m, 8H, $2CH_3$, CyPrCH), 1.50–1.75 (m, 4H, $NCCH_2$), 2.25–2.55 (m, 16H, $NCH_2$), 3.49 (s, 8H, benzylic), 7.10–7.40 (m, 20H, aromatic).

Compound 23 (Scheme 4): Compound 23 was prepared (20%) following the procedure used for 18. The product was recrystallized from ethanol/ether; mp=270° C. (dec) $^1$HNMR ($D_2O$) δ0.88 (dd, J=6.8, 7.0 Hz, 2H, $CyPrCH_2$), 1.25 (t, J=6.1 Hz, 2H, CyPrCH), 1.30 (t, J=7.3 Hz, 6H, $2CH_3$), 2.12 (pent., J=7.9 Hz, 4H, $NCCH_2$), 2.89 (dd, J=8.5, 12.2 Hz, 2H, $NCH_2$), 3.08–3.30 (m, 14H, $NCH_2$); $^{13}$C-NMR ($D_2O$) δ13.62, 14.10, 17.25, 26.35, 46.70, 47.49, 47.81, 54.41; MS (m/z) 271.4 ($M^+H^+$), 307.3 ($M^+H^+$+2 HCl), 156.7, 136.3 (100%).

Compound 23 (via Scheme 4A): Referring specifically to Scheme 4A, 3-ethylamino propionitrile, 101, was prepared by the method of Israel et al. (1964). $^1$H-NMR ($CDCl_3$): δ1.13 (t, J=7.2 Hz, 3H, $CH_3$), 2.53 (t, J=6.8 Hz, 2H, $NCH_2$), 2.69 (q, J=7.2 Hz, 2H, $NCH_2$), 2.94 (t, J=6.8 Hz, 2H, $CNCH_2$); $^{13}$C NMR ($CDCl_3$): δ15.09, 18.62, 43.37, 44.82, 118.75.

N,1-Ethylpropane-1,3-diamine, 102: $LiAl H_4$ (2.54 g, 66.93 mmol) was taken into a flame dried,3-necked flask. THF (75 ml) was added slowly and stirred at room temperature for 20 min. under argon atmosphere. Compound 101 (4.322 g, 44.1 mmol) in 25 ml THF was added dropwise, stirred its contents over night at 80° C. The reaction mixture was cooled to room temperature and quenched with 150 ml 30% NaOH solution. The organic layer was separated, followed by extraction of aqueous layer with chloroform (100 ml). Combined organic layers were dried over $Na_2SO_4$. Solvents were evaporated under vacuum to afford 3.28 g (73%) of compound 102 as an oil which was relatively pure from NMR spectrum and used in the next step without further purification. $^1$H NMR ($CDCl_3$): δ1.11 (t, J=7.2 Hz, 3H, $CH_3$), 1.64 (Pent, J=7.0 Hz, 2H, $NCCH_2$), 2.55–2.71 (m, 4H, $NCH_2$), 2.77 (t, J=6.8 Hz, 2H, $NCH_2$); $^{13}$C NMR ($CDCl_3$): δ15.26, 25.55, 33.89, 40.33, 44.13, 47.60.

N-Ethyl-N-(3-Mesitylene Sulfonylamino Propyl)-Mesitylene Sulfonylamide, 3: Compound 102 (2.12 g, 20.78 mmol) was taken in 14 ml of dioxane/water (1:1) and a solution of mesitylenesulfonyl chloride (11.82 g, 54.05 mmol) in 7 ml dioxane was added dropwise (in about 0.5 h) while maintaining the pH at about 12 with 5% NaOH solution. A thick gum-like product separated out of solution. Supernatant liquid was decanted. Crude product was column purified with hexanes and ethyl acetate (4:1) to afford 3.37 g (35%) of product 3 as white solid, m.p. 101–102 ° C. $^1$H NMR ($CDCl_3$): δ0.95 (t, J=6:99 Hz, 3H, $CH_3$), 1.68 (Pent, J=6.25 Hz, 2H, $NCCH_2$), 2.29 (s, 6H, $2CH_3$), 2.56 (s, 6H, $2CH_3$), 2.62 (s, 6H, $2CH_3$), 2.91 (m, 2H, $NHCH_2$), 3.12 (q, J=7.0 Hz, 2H, $NCH_2$), 3.31 (t, J=6.44 Hz, 2H, $NCH_2$), 4.93 (br, NH), 6.93 (s, 2H aromatic), 6.95 (s, 2H, aromatic); $^{13}$C NMR ($CDCl_3$): δ12.57, 20.93, 22.81, 22.89, 27.84, 39.26, 39.99, 42.29, 131.95, 132.05, 133.32, 138.90, 140.00, 142.02, 142.57

Compound 15' was prepared according to the method of Ashton et al. (1988), *J. Med. Chem.* 31, 2304.

Mesitylene sulfonic acid 2-mesitylene sulfonyloxymethyl-trans-cyclopropyl methyl ester, 16': Compound 15' (1.65 g, 16.18 mmol) was dissolved in 10 ml of pyridine and cooled to 0° C. A solution of mesitylene-sulfonyl chloride (9.13 g, 41.75 mmol) in 23 ml of pyridine was added slowly over a span of about 15 minutes, stirred at room temperature for 3 hours, and then poured onto ice (75 g). White solid precipitated out which was filtered and recrystalized from EtOH; yield 2.8g (37%); m.p. 83–84° C. $^1$H NMR ($CDCl_3$): δ0.50–0.65 (m, 2H, $CyPrCH_2$), 1.00–1.20 (m, 2H, CyPrCH), 2.31 (s, 3H, $CH_3$), 2.34 (s, 3H, $CH_3$), 2.60 (s, 6H, $2CH_3$), 2.61 (s, 6H, $2CH_3$), 3.70–3.90 (m, 4H, $2CH_2$), 6.97 (s, 2H, aromatic), 6.99 (s, 2H, aromatic); $^{13}$C NMR ($CDCl_3$): δ9.47, 16.36, 21.04, 22.57, 72.13, 130.62, 131.76, 139.79, 143.37. MS: (m/z) 466 ($M^+$), 452, 386, 200, 171, 134, 118 (100%), 91, 77.

N-Ethyl-N-{3[(2-{[3-ethyl-mesitylenesulfonylamino) propyl]-mesitylenesulfonylaminomethyl}-(E)-cyclopropylmethyl)-mesitylenesulfonylamino]-propyl}mesitylenesulfonylamide, 22': Compound 3 (2.5 g, 5.37 mmol) was taken into a flame dried 3-necked flask, dissolved in 40 ml anhydrous DMF. NaH (95%, 300 mg) was added slowly under argon atmosphere at 32° C. Contents were stirred at room temperature for 0.5 hours, then a solution of 16' (1.16 g, 2.49 mmol) in 35 ml anhydrous DMF was added over a period of 10 minutes. The reaction mixture was heated to 70° C., stirred for 4 hrs, cooled to 0° C., followed by quenching with 10 ml $H_2O$. The quenched reaction was then extracted with ether (3×30 ml), the combined organic layers were washed with $H_2O$ (30 ml×4) and brine (2×25 ml). The solvents were then removed to afford crude oil, which was purified by column chromatography to yield 22', a low melting white semi-solid in 40% yield (1.0 g). $^1$H NMR ($CDCl_3$): δ0.34 (dd, J=6.6, 6.8 Hz, 1H, CyPrCH), 0.70–0.80 (m, 1H, CyPr), 0.95 (t, J=7.1 Hz, 6H, $2CH_3$), 1.60–1.75 (m, 4H, $2CH_2$) 2.30 (s, 12H, $4CH_3$), 2.54 (s, 24H, $8CH_3$), 2.60–2.89 (m, 2H, NCH), 2.93–3.25 (m, 14H, $NCH_2$), 6.92 (s, 4H, aromatic), 6.93 (s, 4H, aromatic); $^{13}$C NMR ($CDCl_3$): δ12.69, 15.69, 20.95, 22.75, 25.29, 40.17, 42.64, 43.40, 48.90, 131.92, 131.98, 132.99, 133.26, 140.08, 140.12, 142.34, 142.49.

N-Ethyl-N'-(2-(3'-ethylamino-propylaminomethyl)-trans-cyclopropylmethyl)-propane-1,3-diamine tetrahydrochloride, 23: Phenol (1.68 g, 17.8 mmol) and HBr (33%) in glacial acetic acid (8.9 mL) were added successively to a solution of 22' (447 mg, 0.45 mmol) in $CH_2Cl_2$ (5 mL) at room temperature. The solution was stirred for 48 hrs. $H_2O$ (6 mL) was added, followed by extraction with $CH_2Cl_2$ (3×8 mL). The aqueous layer was evaporated under reduced pressure and the residue was taken up in ION NaOH (3 mL), followed by extraction with $CHCl_3$ (12×6 mL). Chloroform was distilled off to afford a thick gum which was taken into anydrous ether. Anydrous HCl gas was passed through the solution to precipitate the tetrahydrochloride of 23 as white solid. (140 mg, 75% yield). The product was recrystallized from ethanol/ether; mp=270° C. (dec). $^1$H NMR (D$_2$O): δ0.88 (dd, J=6.8, 7.0 Hz, 2H, CyPrCH$_2$), 1.25 (t, J=6.1 Hz, 2H, CyPrCH), 1.30 (t, J=7.3 Hz, 6H, 2CH$_3$), 2.12 (pent., J=7.9 Hz, 4H, NCCH$_2$), 2.89 (dd, J=8.5, 12.1 Hz, 2H, NCH$_2$), 3.08–3.30 (m, 14H, NCH$_2$); $^3$C NMR (D$_2$O): δ13.62, 14.10, 17.25, 26.35, 46.70, 47.49, 47.81, 54.41; MS (m/z) 271.4 (M$^+$H$^+$), 307.3 (M$^+$H$^+$+2 Hcl), 156.7, 136.3 (100%).

Compound 24: Compound 24 was prepared by the method of Ashton et al. (1988) in 75% yield as a colorless oil. $^1$HNMR (CDCl$_3$) δ0.22 (dt, J=5, 5 Hz, 1H, CyPrCH$_2$), 0.70–0.85 (m, 1H, CyPrCH$_2$), 1.35 (m, 2H, CyPrCH), 3.27 (dd, J=11, 11 Hz, 2H, CH$_2$OH), 3.70–3.90 (br, 2H, OH), 4.14 (dd, J=6, 11 Hz, 2H, CH$\underline{H}$OH); $^{13}$C-NMR (CDCl$_3$) δ8.39, 17.43, 63.80.

Compound 25: Compound 25 was obtained using the method of Fabiano et al. (1987). To a solution of the diol 24 (1.7 g, 17.01 mmol) in anhydrous THF (10 mL) was added a 0.4 M solution of HN$_3$ in toluene (102 mL) followed by a solution of diisopropyl azidodicarboxylate (7.48 g, 36.99 mmol) in THF (15 mL). To the resulting mixture was added a solution of PPh$_3$ (21.6 g, 92.35 mmol) in THF (30 mL) with stirring. As the reaction is exothermic, the temperature was controlled by the rate of addition of the PPh$_3$ solution. Stirring was continued for 1 hour at RT and then overnight at 50° C. H$_2$O (3.5 mL) was added, stirred at 50° C. for another 6 hours. The solvents were removed under vacuum and the residue was partitioned between CH$_2$Cl$_2$ (100 mL) and 1N HCl (100 mL). The aqueous phase was extracted with CH$_2$Cl$_2$ (4×100 mL). Removal of H$_2$O under reduced pressure (40° C.) gave 25 as a white solid which was recrystallized from methanol/ether (0.650 g, 25%). mp=230° C. (dec);$^1$HNMR (D$_2$O) δ0.40–0.53 (m, 1H, CyPyCH), 1.00–1.15 (m, 1H, CyPrCHH), 1.30–1.48 (m, 2H, CyPrCH), 2.75–2.95 (m, 2H, NCH$_2$), 3.20–3.35 (m, 2H, NCH$_2$).

Compound 26: Compound 26 was obtained (93%) from 25 following the procedure 7. The product was purified by column chromatography using silica gel and hexanes:ethylacetate (3:2) as an eluant. mp=152–153° C.; $^1$HNMR (CDCl$_3$) δ0.06–0.1 (m, 1H, CyPrCH$_2$), 0.62–0.75 (m, 1H, CyPrCHH), 1.00–1.16 (m, 2H, CyPrCH), 2.29 (s, 6H, 2CH$_3$), 2.62 (s, 12H, 4CH$_3$), 2.69 (dd, J=5.0 and 8.6 Hz, 2H, NCHH), 3.04 (dd, J=5.0 and 13.2 Hz, NCHH), 3.70 (s, 2H, NH), 6.04 (s, 4H, aromatic).

Compound 27: Compound 27 was obtained from 26 in 64% yield; mp=56–58° C.; $^1$HNMR (CDCl$_3$) δ0.05–0.09 (m, 1H, CyPrCHH), 0.7–0.81 (m, 1H, CyPrCHH), 0.95 (t, J=7.1 Hz, 8H, 2CH$_3$ and 2H, CyPrCH), 1.65–1.79 (m, 4H, NCHH$_2$), 2.28 (s, 6H, 2CH$_3$), 2.29 (s, 6H, 2CH$_3$), 2.54 (s, 12H, 4CH$_3$), 2.55 (s, 12H, 4CH$_3$), 2.69–2.90 (m, 2H, NCHH), 3.00–3.20 (m, 12H, NCR), 3.29–3.40 (m, 2H, NCHH), 6.92 (s, 4H, aromatic), 6.93 (s, 4H, aromatic); $^{13}$C-NMR (CDCl$_3$) δ12.63, 13.92, 20.96, 22.73, 22.77, 25.50, 40.07, 42.65, 43.49, 45.17, 131.92, 133.00, 140.06, 142.35; MS (m/z) δ999.40 (M$^+$), 815.30, 533.20, 167.10, 119.00 (100%).

Compound 28 (Scheme 5): Compound 28 was prepared from 27 in 75% yield; mp=240° C. (dec); $^1$HNMR (D$_2$O) δ0.38–0.48 (m, 1H, CyPrCHH), 0.9–1.1 (m, 1H CyPrCHH), 1.29 (t, J=6.3 Hz, 8H, 2CH$_3$ and 2H, CyPrCH), 1.98–2.10 (m, 4H, NCCH$_2$), 2.88–3.05 (m, 8H, NCH$_2$), 3.05–3.18 (m, 8H, NCH$_2$); $^{13}$C-NMR (D$_2$O) δ12.63, 13.53, 15.74, 26.89, 45.82, 47.30, 47.39, 50.58; HPLC R$_T$=26.97.

Compound 28 (via Scheme 5A): Referring specifically to Scheme 5A, compound 24 was made as described above. Mesitylenesulfonic acid 2-mesitylenesulfonyloxymethyl-cis-cyclopropylmethyl ester, 25' was obtained from 24 as described above for compound 16'. m.p. 240° C. $^1$H NMR (CDCl$_3$): δ0.31–0.40 (m, 1H, CyPr), 0.86–0.99 (m, 1H, CyPr), 1.25–1.41 (m, 2H, CyPr), 2.32 (s, 6H, 2CH$_3$), 2.60 (s, 12H, 4CH$_3$), 3.85–4.10 (m, 4H, 2CH$_2$), 6.99 (s, 4H, aromatic); $^{13}$C NMR (CDCCl$_3$): δ9.71, 15.25, 21.08, 22.61, 69.61, 130.63, 131.79, 139.82, 143.39; MS 466 (M$^+$), 452, 266, 200, 185, 171, 119 (100%).

N-Ethyl-N-{3[(2-{[3-ethyl-mesitylenesulfonylamino) propyl]-mesitylenesulfonylaminomethyl}-(Z)-cyclopropylmethyl)-mesitylenesulfonylamino]-propyl}mesitylenesulfonylamide, 27, was obtained by reacting 25' with 3 in 64% yield; mp=56–58° C. $^1$H NMR (CDCl$_3$): δ0.05–0.09 (m, 1H, CyPrCHH), 0.7–0.81 (m, 1H, CyPrCHH), 0.95 (t, J=7.1 Hz, 8H, 2CH$_3$ and 2H, CyPrCH), 1.65–1.79 (m, 4H, NCHH$_2$), 2.28 (s, 6H, 2CH$_3$), 2.29 (s, 6H, 2CH$_3$), 2.54 (s, 12H, 4CH$_3$), 2.55 (s, 12H, 4CH$_3$), 2.69–2.90 (m, 2H, NCHH), 3.00–3.20 (m, 12H, NCH$_2$), 3.29–3.40 (m, 2H, NCHH), 6.92 (s, 4H, aromatic), 6.93 (s, 4H, aromatic); $^{13}$C NMR (CDCl$_3$): δ12.63, 13.92, 20.96, 22.73, 22.77, 25.50, 40.07, 42.65, 43.49, 45.17, 131.92 133.00, 1460.06, 142.35; MS (m/z) δ999.40 (M$^+$), 815.30, 533.20, 167.10, 119.00 (100%).

N-Ethyl-N'-(2-(3'-ethylamino-propylaminomethyl)-cis-cyclopropylmethyl)-propane 1,3-diamine tetrahydrochloride, 28: This compound was synthesized by following the procedure described above for compound 23 (Scheme 4A) in 75% yield. White solid, mp=240° C. (dec). $^1$H NMR (D$_2$O): δ0.38–0.48 (m, 1H, CyPrCHH), 0.9–1.1 (m, 1H, CyPrCHH), 1.29 (t, J=6.3 Hz, 8H, 2CH$_3$ and 2H, CyPrCH), 1.98–2.10 (m, 4H, NCCH$_2$), 2.88–3.05 (m, 8H, NCH$_2$), 3.05–3.18 (m, 8H, NCH$_2$); $^{13}$C NMR (D$_2$O): δ12.63, 13.53, 15.74, 26.89, 45.82, 47.30, 47.39, 50.58; HPLC R$_T$=26.97.

Compound 31: This compound was prepared by the method of Buchman et al. (1942). Mesitylenesulfonyl chloride (4.55 g, 21 mmol) in dioxane (15 mL) was added dropwise with magnetic stirring to 29 (1.1 g, 6.9 mmol) in 20 mL of a mixture of NaOH:dioxane (2:1). The mixture was maintained at pH 10–11 with occasional addition of a 5% solution of KOH. Once the addition was completed, the reaction mixture was left for an additional hour. The white solid was filtered off and dried to afford 31 (2 g, 65%). mp 201–202° C. (crystallized from methanol-water); $^1$HNMR (CDCl$_3$) δ1.35 (m, 2H), 1.95 (m, 2H), 2.30 (s, 6H), 2.60 (s, 6H), 2.60 (s, 12H), 3.32 (m, 2H), 5.18 (br, 2H), 6.95 (s, 4H); $^{13}$C-NMR (CDCl$_3$) δ20.96, 22.88, 23.80, 54.68, 132.09, 134.10, 139.16, 142.80. MS (m/z, relative intensity), 451 (MH$^+$, 2), 267 (73), 183 (48).

Compound 32: Compound 32 (70%) was obtained from 30 following the procedure described by Buchman et al. (1942). mp=192–193° C. (crystallized from methanol-water) $^1$HNMR (CDCl$_3$) δ1.90–2.18 (m, 4H), 2.35 (s, 6H), 2.60 (s, 12H), 3.63 (br, 2H), 5.41 (br, 2H), 6.96 (s, 4H); $^{13}$C-NMR (CDCl$_3$) δ: 20.95, 22.89, 25.32, 51.20, 132.04, 134.08, 139.30, 142.51 MS (m/z, relative intensity) 451 (MH$^+$, 2), 267(76), 183(65).

Compound 33: NaH (95%, 115 mg, 4.8 mmol) was added to a solution of 31 (900 mg, 2 mmol) in DMF (20 mL) at 0° C. The mixture was stirred at 0° C. for 30 minutes and a solution of the alkylating agent 9 (1.53 g, 4.4 mmol) in DMF (10 mL) was added dropwise. The reaction mixture was stirred at 0° C. for 30 minutes and then at 70–80° C.

overnight, cooled and quenched with water (5 mL). The solvent was distilled off with a vacuum pump and the residue was extracted into chloroform-water. The organic layer was dried and evaporated to leave a residue that was purified by flash chromatography on silica gel (elution with 20% ethyl acetate in hexanes) to yield 1.2 g (60%) of 33 as a colorless, glassy oil. $^1$HNMR (CDCl$_3$) δ: 0.98 (t, 6H), 1.40–1.70 (b, 6H), 1.82 (b, 2H), 2.28,230 (s, 12H), 2.56–2.58 (s, 24H), 2.80–3.20 (m, 12H), 4.20 (br, 2H), 6.93–6.96 (s, 8H); $^{12}$C-NMR (CDCl$_3$) δ: 12.70, 20.94, 21.70, 22.76, 22.90, 28.20, 40.20, 41.54, 43.16, 55.48, 131.91, 132.10, 133.02, 133.18, 140.23, 142.80, 143.17, FABMS (m/z, relative intensity) 985.4 (MH$^+$, 37), 801.4 (84), 619.3 (20), 619.3 (21).

Compound 34: Compound 34 (50%) was obtained from 32 following the procedure described above. $^1$HNMR (CDCl$_3$) δ: 0.98 (t, 6H), 1.50 (m, 4H), 1.80 (br, 2H), 2.12 (br, 2H), 2.30 (s, 6H), 2.52, 2.54 (s, 12H) 2.82 (m, 4H), 2.93–3.23 (m, 8H), 4.20 (br, 2H), 6.93 (s, 8H); $^{13}$C-NMR (CDCl$_3$) δ: 12.69, 20.94, 22.75, 22.82, 24.63, 25.94, 40.14, 42.16, 43.25, 55.43, 131.89, 132.23, 133.51, 135.08, 139.52, 140.16, 142.22, 142.88; FABMS (m/z, relative intensity) 985.4 (MH$^+$, 11%) 801.3 (59), 619.3 (26).

Compound 35: Phenol (800 mg, 8.5 mmol) and 30% HBr in glacial acetic acid (14 mL) were added successively to a solution of the tetramide 33 (300 mg, 0.30 mmol) in CH$_2$Cl$_2$ (14 mL) at room temperature. The solution was stirred at room temperature for 48 hrs. H$_2$O (20 mL) was added followed by extraction with CHCl$_3$ (3×20 mL). The aqueous portion was evaporated to dryness and the residue was taken up in 10N NaOH (5 mL) followed by extraction with CHCl$_3$ (10×5 mL). The combined organic phases were dried and evaporated. The resulting residue was dissolved in ethanol (3 mL) and acidified with three drops of concentrated HCl, cooled and filtered. White crystals of 35 were obtained (50 mg, 40%). $^1$HNMR (D$_2$O) δ: 1.20 (t, 6H), 1.80–2.21 (m, 6H), 2.35 (m, 2H), 3.08 (m, 12H), 4.00 (m, 2H); $^{13}$C-NMR (D$_2$O) δ: 14.20, 22.57, 26.34, 46.26, 46.76, 47.44, 57.57, MS (m/z, relative intensity) 257.2 (MH$^+$, 27), 293.3 (M+2H$^+$+2Cl$^-$, 4) 172.2 (100); HPLC: R$_T$=27.47 min.

Compound 36: Compound 36 (40 mg, 37%) was obtained following the procedure described above for 35 using 300 mg of 34 as a reactant. $^1$HNMR (D$_2$O) δ: 2.10–2.25 (m, 4H), 2.35–2.55 (m, 4H), 3.08–3.30 (m, 12H), 4.15 (m, 2H); $^{13}$C-NMR (D$_2$O) δ: 14.12, 25.04, 26.28, 46.72, 47.31, 47.46, 57.98; ESIMS (m/z, relative intensity): 257.3 (MH$^+$, 100), 293.3 (M$^+$ 2H$^+$+2Cl$^-$, 6), 172.3 (12); HPLC: R$_T$=25.91 min.

Compound 39: Compound 39 was obtained from 37 (see Buchman et al. (1942)) following the procedure described above. From 3.85 g (22 mmol) of 37 was obtained 1.68 g (65%) of 39 as a colorless oil. $^1$HNMR (CDCl$_3$) δ: 1.60 (m, 2H), 1.85 (m, 2H), 2.20 (br, 2H), 3.38 (m, 2H), 3.60 (m, 2H); $^{13}$C-NMR (CDCl$_3$) δ: 20.80, 43.46, 66.33.

Compound 40: A three-necked flask equipped with an addition funnel and a condenser containing LiAlH$_4$ (2.8 g, 73.6 mmol) was cooled in an ice bath as 80 mL of dry THF was added under a nitrogen atmosphere. The ice bath was removed and the mixture was stirred at room temperature while a solution of 38 (see Buchman et al. (1942)) (6.16 g 36 mmol) in 30 mL of THF was added dropwise. The mixture was stirred at reflux for 18 hrs., After cooling in an ice bath, the mixture was treated cautiously with a saturated solution of NH$_4$Cl (16 mL) and then with ethyl acetate (16 mL). The insoluble salts were removed by filtration and the filtrate was evaporated under reduced pressure. The residue was dissolved in ethyl acetate, dried (NaSO$_4$), filtered and evaporated to give 3.6 g (86%) of a colorless oil. $^1$HNMR (CDCl$_3$) δ: 1.58 (m, 2H), 2.05 (m, 2H), 2.70 (br, 2H), 3.60 (m, 2H), 3.82 (m,2H); $^{13}$C-NMR (CDCl$_3$) δ: 20.32, 20.82, 37.46, 62.72.

Compound 41: Compound 41 was obtained from 39 following the procedure described immediately above. From 1.97 g (17 mmol) of 39 was obtained 700 mg (21%) of crude 41 which was used in subsequent steps without further purification.

Compound 42: To a solution of the alcohol 40 (1.97 g, 17 mmol) in THF (10 mL) was added 42 mL of a 0.95 M solution of hydrazoic acid (HN$_3$, 39.8 mmol), followed by a solution of diisopropyl-azodicarboxylate (7.45 g, 69 mmol) in THF (20 mL). To the resulting mixture, a solution of triphenylphosphine (19.6 g, 75 mmol) in THF (85 mL) was added while stirring. After 1 hour at room temperature the reaction mixture was heated at 50° C. for 6 hours, the solvents were removed in vacuo and the residue was partitioned between CH$_2$Cl$_2$ (60 mL) and 1 N HCl (30 mL). The aqueous phase was extracted with additional CH$_2$Cl$_2$ (3×10 mL). Removal of the water under reduced pressure gave the diamino hydrochloride 42 (800 mg, 25%). This was used in subesquent steps without further purification.

Compound 44: Mesitylenesulfonylchloride (2.70 g, 126 mmol) in dioxane (10 mmol) was added dropwise with stirring to 42 (800 mg, 4.2 mmol) dissolved in a mixture of 1N NaOH and dioxane (1:1). The mixture was maintained at pH 10–11 with occasional addition of a 5% solution of iN NaOH. Once the addition was complete, the reaction mixture was stirred for an additional hour. The solvent was decanted and the oily residue was washed with hexane, filtered, and dried, which afforded 490 mg (25%) of 44. mp=138–139° C. (crystallized from methanol-water). $^1$HNMR (CDCl$_3$) δ: 1.50 (m, 2H), 1.88 (m, 2H), 2.30 (br, 8H), 2.62 (s, 12H), 2.92 (m, 4H), 5.05 (t, 2H), 6.90 (s, 4H); $^{13}$C-NMR(CDCl$_3$) δ: 20.92, 21.65, 22.95, 39.01, 46.82, 131.96, 134.20, 139.03, 142.12; MS (m/z; relative intensity): 478 (M$^+$, 12), 295 (90).

Compound 43: Compound 43 was obtained from 41 following the procedure described above. From 700 mg of 41 was obtained 400 mg (25%) of 43. mp=130–132° C. (crystallized from methanol-water) $^1$HNMR (CDCl$_3$) δ: 1.50 (m, 2H), 1.83 (m, 2H), 2.25 (m, 2H), 2.30 (s, 6H), 2.60 (s, 12H), 2.90 (m, 4H), 5.20 (t, 2H), 6.95 (s, 4H); $^{13}$C-NMR (CDCl$_3$) δ: 20.91, 21.66, 22.95, 38,97, 46.80, 131.95, 133.72, 139.03, 142.11; MS (m/z, relative intensity): 478 (M$^+$, 7) 295 (54)

Compound 46—NaH (95%, 52.3 mg, 2.18 mmol) was added to a solution of 44 (400 mg, 0.84 mmol), in DMF (20 mL) at 0° C. The mixture was stirred at 0° C. for 30 minutes, and a solution of N-ethyl-N-mesitylenesulfonamide-3-bromopropylamine 9 (758 mg, 218 mmol) in DMF (15 mmol) was added dropwise. The reaction mixture was then stirred at 0° C. for 15 minutes, and then at 70–80° C. overnight, and then cooled and cautiously quenched with water (25 mL). The mixture was extracted with ethyl ether (3×30 mL), and the pooled organic fractions were washed with H$_2$O (4×30 mL) and brine (2×20 mL), and dried (NaSO$_4$). The solvent was evaporated under reduced pressure, yielding an oil. The crude oil was purified by column chromatography using hexanes:ethyl acetate (8:2), followed by an 8:3 hexanes:ethyl acetate eluant. 800 mg (94%) of 46 were obtained as a glassy oil. $^1$HNMR (CDCl$_3$) δ: 0.95 (t, 6H), 1.30 (m, 3H), 1.61 (m, 5H), 2.10 (m, 2H), 2.32 (s, 12H), 2.52 (s, 24H), 2.80–3.35 (m, 14H), 3.30 (m, 2H), 6.95, 6.98 (s, s, 8H); $^{13}$C-NMR (CDCl$_3$) δ: 12.64, 20.93, 22.72, 22.82, 23.30, 24.87, 37.46, 39.97, 42.47, 43.60, 50.06, 131.91, 133.70, 139.99, 142.30; FABMS (m/z, relative intensity); 1013.4 (MH$^+$, 33), 829,5 (29).

Compound 45: Compound 45 was obtained from 43 following the procedure described immediately above. From 300 mg of 43 was obtained 500 mg (78%) of a glassy oil product. $^{13}$C-NMR (CDCl$_3$) δ: 12.63, 20.93, 22.72, 22.81, 23.28, 24.97, 37.45, 39,95, 42.29, 43.68, 50.01, 131.91, 133.70, 139.97, 140.03, 142.31; FABMS (m/z, relative intensity): 1013.5 (MH$^+$, 28) 829.5 (28).

Compound 48 (Scheme 9): Phenol (3.17 g, 33.7 mmol) and 30% HBr in glacial acetic acid (17 mL) were added successively to a solution of 46 (759 mg 0.74 mmol) in CH$_2$Cl$_2$ (10 mL) at room temperature. The solution was stirred for 48 hours, H$_2$O (10 mL) was added, followed by extraction with CH$_2$Cl$_2$ (3×10 mL). The aqueous layer was evaporated under reduced pressure and the residue was taken up in 10N NaOH (5 mL) followed by extraction with CHCl$_3$ (12×10 mL). After removal of CHCl$_3$, the residue was taken up in ethanol (10 mL) and acidified with concentrated HCl (0.5 mL). The precipitate was recrystallized from ethanol-ether to give 190 mg (60%) of 48 as white crystals. $^1$HNMR (D$_2$O), δ: 1.30 (t, 6H), 1.85 (m, 2H), 2.08–2.25 (m, 6H), 2.50 (br, 2H), 3.10–3.30 (m, 16H); $^{13}$C-NMR (D$_2$O) δ: 14.24, 26.44, 38.77, 46.80, 47.60, 48.41, 55.05; HPLC: R$_T$=28.06 min.

Compound 47 (Scheme 8): Following the procedure described for 48, 50 mg (23%) of 47 were obtained as white crystals. $^1$HNMR (D$_2$O) δ: 1.30 (t, 6H), 1.80 (m, 2H), 2.02–2.28 (m, 6H), 2.50 (br, 2H), 3.02–3.30 (m, 16H); $^{13}$C-NMR (D$_2$O) δ: 14.22, 26.43, 38.77, 46.80, 47.60, 48.40, 55.03; HPLC: R$_T$=28.047 min.

Compound 47 (via Scheme 8A): Referring specifically to Scheme 8A, mesitylenesulfonic acid 2-mesitylenesulfonyloxymethyl-trans-cyclobutyl methyl ester, 41' (83%) was obtained from 39 following the procedure described for 16' (Scheme 4A). m.p. 77–78° C. $^1$H NMR (CDCl$_3$): δ1.65 (m, 2H), 1.95 (m, 2H), 2.30 (s, 6H), 2.58, 2.60 (s, s 12H), 3.88 (d, 4H), 6.96 (s, 4H); $^{13}$C NMR (CDCl$_3$): δ20.67, 20.86, 22.39, 36.37, 71.28, 130.35, 131.59, 131.62 m 139.60, 143.17. EI-MS m/z (relative intensity) 48 (M$^+$, 8), 281 (5), 199 (22), 183 (36).

N-Ethyl-N-{3[(2-{[3-ethyl-mesitylenesulfonylamino)propyl]-mesitylenesulfonylaminomethyl}-trans-cyclobutylmethyl)-mesitylenesulfonylamino]-propyl}mesitylenesulfonylamide, 45, was obtained by reacting 41' with 3 following the procedure described for the synthesis of 22' in 78% yield as a glassy oil. $^1$H NMR (CDCl$_3$): δ; 13C NMR (CDCl$_3$): δ12.63, 20.93, 22.72, 22.81, 23.28, 24.97, 37.45, 39.95, 42.29,43.68, 50.01, 131.91, 133.70, 139.97, 140.03, 142.31; FABMS (m/z, relative intensity): 1013.5 (M$^+$, 28) 829.5 (28).

N-Ethyl-N'-(2-(3'-ethylamino-propylaminomethyl)-trans-cyclobutylmethyl)-propane1,3-diamine tetrahydrochloride, 47: Following the procedure described above for 23 (Scheme 4A), 50 mg (23%) of 47 were obtained as white solid. $^1$H NMR (D$_2$O): δ1.30 (t, 6H), 1.80 (m, 2H), 2.02–2.28 (m, 6H), 2.50 (br, 2H), 3.02–3.30 (m, 16H); $^{13}$C NMR (D$_2$O): δ14.22, 26.43, 38.77, 46.82, 47.60, 48.40, 55.03; HPLC: R$_T$=28.047 min.

Compound 48 (Scheme 9A): referring specifically to Scheme 9A, mesitylenesulfonic acid 2-mesitylenesulfonyloxymethyl-cis-cyclobutylmethyl ester, 42' (80%) was obtained from 40 following the procedure described for 16' m.p. 92–93° C. $^1$H NMR (CDCl$_3$) δ1.72 (m, 2H), 2.05 (b, 2H), 2.31 (s, 6H), 2.57, 2.59 (s, 12H), 2.78 (b, 2H), 3.85–4.10 (m, 4H), 6.96 (s, 4H). $^{13}$C NMR (CDCl$_3$) δ20.69, 20.89, 21.49, 22.41, 34.94, 69.14, 130.41, 131.66, 139.62, 139.65, 143.20, 143.25. EI-MS m/z (relative intensity) 480 (M$^+$, 0.7), 281 (7), 199 (22), 183 (47).

N-Ethyl-N'-(2-(3'-ethylamino-propylaminomethyl)-cis-cyclobutylmethyl)-propane1,3-diamine tetrahydrochloride, 48: This compound was synthesized according to the procedure described for 23 (Scheme 4A) in 60% yield as a white solid. The product was recrystallized from ethanol-ether to afford 190 mg (60%) of 48 as white crystals. $^1$H NMR (D$_2$O): δ1.30 (t, 6H), 1.85 (m, 2H), 2.08–2.25 (m, 6H), 2.50 (b, 2H), 3.10–3.30 (m, 16H); $^{13}$C NMR (D$_2$O): δ14.24, 26.44, 38.77, 46.80, 47.60, 48.41, 55.05; HPLC: R$_T$=28.06 min.

Compound 50: This compound was prepared according to the method of Miller et al. (1959). Using 49 as a reactant, 50 was prepared in 70% yield. $^1$HNMR (CDCl$_3$) δ4.10 (s, slightly broad, 4H, CH$_2$OH), 5.83 (s, again slightly broad, 2H, CH=CH); $^{13}$C-NMR (CDCl$_3$, MeOH) δ62.07, 130.08.

Compound 51: Compound 51 (86%) was prepared as described above for 25 as a white solid. $^1$HNMR (D$_2$O) δ3.69 (d, J=5 Hz, 4H, NCH$_2$), 6.00–6.10 (m, 2H, CH=CH); $^{13}$C-NMR (D$_2$O) δ43.10, 130.75

Compound 52: Compound 52 (45%) was prepared as described above for 25 from commercially available cis-butene-1,4-diol 50'. mp=205° C. (dec); $^1$HNMR (D$_2$O) δ3.77 (d, J=5.5 Hz, 4H, NCH$_2$), (t, J=4.6 Hz, 2H, CH=CH), $^{13}$C-NMR (D$_2$O) δ38.90, 129.74.

Compound 53: Compound 53 was prepared from 51 in 29% yield mp=171–172° C.; $^1$HNMR (CDCl$_3$) δ2.31 (s, 6H, 2CH$_3$), 2.60 (s, 12H, 4CH$_3$), 3.45–3.55 (m, 4H, NCH$_2$), 5.40–5.50 (m, 2H, CH=CH), 6.95 (s, 4H, aromatic)

Compound 54: Compound 54 was prepared from 52 in 74% yield. mp=109–110° C.; $^1$HNMR (CDCl$_3$) δ2.31 (s, 6H, 2CH$_3$), 2.60 (s, 12H, 4CH$_3$), 3.45–3.55 (m, 4H, NCH$_2$), 5.40–5.50 (m, 2H, CH=CH), 6.95 (s, 4H, aromatic); $^{13}$C-NMR (CDCl$_3$) δ20.95, 22.92, 39.05, 128.30, 132.03, 133.62, 139.11, 142.42; MS (m/z) 451 (M$^+$), 267, 251, 183, 119 (100%), 91; Anal: (C$_{22}$H$_{30}$N$_2$O$_4$S$_2$).

Compound 55: Compound 55 was prepared in 91% yield as described above for 10. mp=135–136° C.; $^1$HNMR (CDCl$_3$) δ0.95 (t, J=7.1 Hz, 6H, 2CH$_3$), 1.59–1.70 (m, 4H, NCCH$_2$), 2.29 (s, 12H, 4CH$_3$), 2.53 (s, 12H, 4CH$_3$), 2.55 (s, 12H, 4CH$_3$), 2.99 (t, J=7.3 Hz, 8H, NCH$_2$), 3.08 (q, J=7.1 Hz, 4H, NCH$_2$) 3.65 (d, J=5 Hz, 4H, C=C—CH$_2$), 5.40–5.50 (m, 2H, CH=CH), 6.92 (s, 4H, aromatic), 6.93 (s, 4H, aromatic); $^{13}$C-NMR (CDCl$_3$) δ12.62, 20.90, 22.68, 22.77, 25.56, 40.02, 42.53, 43.79, 43.83, 128.51, 131.88, 132.00, 132.71, 133.00, 140.02, 140.17, 142.30, 142.66.

Compound 56: Compound 56 was prepared as described above for 10 from 54 in 88% yield. mp=74–75° C.; $^1$HNMR (CDCl$_3$) δ0.93 (t, J=7.1 Hz, 6H, 2CH$_3$), 1.60–1.70 (m, 4H, NCCH$_2$), 2.29 (s, 6H, 2CH$_3$), 2.30 (s, 6H, 2CH$_3$), 2.52 (s, 12H, 4CH$_3$), 2.55 (s, 12H, 4CH$_3$), 2.95–3.02 (m, 8H, NCH$_2$), 3.07 (q, J=7.1 Hz, 4H, NCH$_2$), 3.74 (d, J=4.6 Hz, 4H, NCH$_2$), 6.90 (s, 4H, aromatic), 6.93 (s, 4H, aromatic); $^{13}$C-NMR (CDCl$_3$) δ12.69, 20.93, 22.71, 22.80, 25.20, 40.12, 42.56, 43.25, 47.06, 129.50, 131.93, 132.03, 132.86, 133.25, 140.07, 140.12, 142.36, 142.62; MS (m/z) 985.3 (M$^+$), 801.3, 718.2, 617.2, 519.2, 336.1, 240.1, 183.0, 119 (100%).

Compound 57 (Scheme 10): Compound 57 was prepared as described above for 12 starting from 35 in 86% yield. mp=250° C. (dec); $^1$HNMR (D$_2$O) δ1.30 (t, J=7.4 Hz, 6H, 2CH$_3$), 2.05–2.20 (m, 4H, NCCH$_2$), 3.05–3.20 (m, 12H, NCH$_2$), 3.75–3.80 (m, 4H, NCH), 6.04–6.10 (m, 2H, CH=CH); $^{13}$C-NMR (D$_2$O) δ13.34, 25.57, 45.90, 46.71, 46.80, 51.04, 131.25; HPLC: R$_T$=27.03 min.

Compound 58 (Scheme 11): Compound 58 was prepared from 56 in 86% yield. mp=240° C.; $^1$HNMR (D$_2$O) δ1.30 (t, J=7.3 Hz, 6H, CH$_3$), 2.10–2.5 (m, 4H, NCCH$_2$), 3.05–3.25 (m, 12H, NCH$_2$), 3.87 (d, J=4.8 Hz, 4H, NCH$_2$), 5.98 (t, J=4.8 Hz, 2A, CH=CH); $^{13}$C-NMR (D$_2$O) δ13.35, 25.69, 45.93, 46.70, 46.96, 47.02, 129.31; HPLC: R$_T$=26.89 min.

Compound 57 (via Scheme 10A): Referring specifically to Scheme 10A, mesitylenesulfonic acid-4-mesitylenesulfonyloxy-E-but-2-enyl ester, 51': Diol 50 (1.76 g, 20 mmol), and benzyltriethylammonium bromide (270 mg, 1 mmol) were taken in a mixture of 30 mL 50% KOH and 30 mL of dioxane. The reaction mixture was stirred in an ice water bath as mesitylene sulfonyl chloride (8.72 g, 40 mmol) in 30 mL of dioxane as added dropwise. When the addition was over, the stirring was continued for an additional hour. Excess water was added and after cooling a white precipitate was filtered. Crystillazation from chloroform-hexane yielded 7.0 g 51' (77%); m.p. 119–120° C. $^1$H NMR (CDCl$_3$): δ2.35 (s, 6H), 2.60 (s, 12H), 4.45 (d 4H), 5.75 (b, 2H), 6.95 (s, 4H); $^{13}$C NMR (CDCl$_3$): δ20.96, 22.52, 67.96, 127.67, 131.69, 131.74, 139.79, 143.45. EI-MS m/z (relative intensity) 452 (M$^+$, 1), 253 (17), 200 (81), 183 (39).

N-Ethyl-N-{3[(2-{[3-ethyl-mesitylenesulfonylamino) propyl]-mesitylenesulfonylaminomethyl}-but-(E)-2-enyl)-mesitylenesulfonylamino]-propyl}mesitylenesulfonylamide 55: This compound was prepared in 91% yield as described above for 22'. mp=135–136° C. $^1$H NMR (CDCl$_3$): δ0.95 (t, J=7.1 Hz, 6H, 2CH$_3$), 1.59–1.70 (m, 4H, NCCH$_2$), 2.29 (s, 12H, 4CH$_3$), 2.53 (s, 12H, 4CH$_3$), 2.55 (s, 12H, 4CH$_3$), 2.99 (t, J=7.3 Hz, 8H, NCH$_2$), 3.08 (q, J=7.1 Hz, 4H, NCH$_2$), 3.65 (d, J=5 Hz, 4H, C=C—CH$_2$), 5.40–5.50 (m, 2H, CH=CH), 6.92 (s, 4H, aromatic), 6.93 (s, 4H, aromatic); $^{13}$C NMR (CDCl$_3$): δ12.62, 20.90, 22.68, 22.77, 25.56, 40.02, 42.53, 43.79, 43.83, 128.51, 131.88, 132.00, 132.71, 133.00, 140.02, 140.17, 142.30, 142.66.

N,N$^1$-bis(3-ethylaminopropyl)-(E)-but-2-ene-1,4-diamine tetrahydrochloride, 57, was prepared as described above for 23 (Scheme 4A) in 86% yield. mp=250° C. (dec). $^1$H NMR (D$_2$O): δ1.30 (t, J=7.4 Hz, 6H, 2CH$_3$), 2.05–2.20 (m, 4H, NCCH$_2$), 3.05–3.20 (m, 12H, NCH$_2$), 3.75–3.80 (m, 4H, NCH$_2$), 6.04=6.10 (m, 2H, CH=CH). $^{13}$C NMR (D$_2$O): δ13.34, 25.57, 45.90, 46.71, 46.80, 51.04, 131.25; HPLC: R$_T$=27.03 min.

Compound 58 (via Scheme 11A): Referring specifically to Scheme 11A, mesitylenesulfonic acid-4-mesitylenesulfonyloxy-E-but-2-enyl ester, 52' was obtained from 50' in 75% yield by following the procedure described above; m.p. 71–72° C. $^1$H NMR (CDCl$_3$): δ2.25 (s, 6H), 2.50 (s, 19H), 4.40 (d, 4H), 5.62 (b, 2H), 6.90 (s, 4H); $^{13}$C NMR (CDCl$_3$): δ20.90, 22.40, 63.66, 127.54, 131.71, 139.69, 143.46. EI-MS m/z (relative intensity) 452 (M$^+$, 3), 253 (47), 199 (35), 183 (76).

N-Ethyl-N-{3[(2-{[3-ethyl-mesitylenesulfonylamino) propyl]-mesitylenesulfonylaminomethyl}-but-(Z)-2-enyl)-mesitylenesulfonylamino]-propyl}mesitylenesulfonylamide, 56, prepared as described above for 22 (Scheme 4A) in 88% yield. mp=74–75° C. $^1$H NMR (CDCl$_3$): δ0.93 (t, J=7.1 Hz, 6H, 2CH$_3$), 1.60–1.70 (m, 4H, NCCH$_2$), 2.29 (s, 6H, 2CH$_3$), 2.30 (s, 6H, 2CH$_3$), 2.52 (s, 12H, 4CH$_3$), 2.55 (s, 12H, 4CH$_3$), 2.95–3.02 (m, 8H, NCH$_2$), 3.07 (q, J=7.1 Hz, 4H, NCH$_2$), 3.74 (d, J=4.6 Hz, 4H, NCH$_2$), 6.90 (s, 4H, aromatic), 6.93 (s, 4H, aromatic); $^{13}$C NMR (CDCl$_3$): δ12.69, 20.93, 22.71, 22.80, 25.20, 40.12, 42.56, 43.25, 47.06, 129.50, 131.93, 132.03, 132.86, 133.25, 140.07, 140.12, 142.36, 142.62; MS (m/z) 985.3 (M$^+$).

N,N$^1$-bis(3-ethylaminopropyl)-(Z)-but-2-ene-1,4-diamine tetrahydrochloride, 58, was prepared from 56 in the same fashion as 23 (Scheme 4A) in 86.5% yield. mp=240° C. $^1$H NMR (D$_2$O): δ1.30 (t, J=7.3 Hz, 6H, CH$_3$), 2.10–2.59 (m, 4H, NCCH$_2$), 3.05–3.25 (m, 12H, NCH$_2$), 3.87 (d, J=4.8 Hz, 4H, NCH$_2$), 5.98 (t, J=4.8 Hz, 2H, CH=CH); $^{13}$C NMR (D$_2$O): δ13.35, 25.69, 45.93, 46.70, 46.96, 47.02, 129.31; HPLC: R$_T$=26.89 min.

Biological Activity Examples

These Examples are provided to illustrate the utility of the present compounds to inhibit neoplastic cell growth. As note above, the Examples do not limit the scope of the invention described and claimed herein in any fashion.

Cell Lines and Media

Human breast cancer cell line MCF7 was grown in Richter's Improved Modified Eagle's Medium supplemented with 10% fetal bovine serum (FBS) and 2.2 g/L sodium bicarbonate. Human brain cancer cell line U251MG-NCI was grown in Dulbecco's Modified Eagle's Medium supplemented with 10% FBS. Human lung cancer cell line A549 was grown in Ham's F-12K medium (Fisher Scientific, Itasca, Ill.), supplemented with 10% FBS and 2 mM L-glutamine. Human colon cancer cell line HT29 was cultured in McCoy's 5A medium (Gibco, BRL, Gaithersburg, Md.), supplemented with 10% FBS. Human prostate cancer cell line PC3 was grown in Dulbecco's Modified Eagles Medium supplemented with 5% FBS. The A549 and MCF7 cell lines were cultured in 100 units/mL penicillin and 100 µg/mL streptomycin. HT29 and U251MG cell lines were grown in 50 µg/mL gentamycin. PC3 cell lines were maintained in 1% antibiotic-antimycotic solution (Sigma, St. Louis, Mo.). The cell cultures were maintained at 37° C. in 5% CO$_2$/95% humidified air. All cell cultures are available from the American Type Culture Collection, Rockville, Md.

Examples 1–8

A standardized protocol was used to evaluate these test cultures and to generate the data shown in FIGS. 1–8:

Day 1:

Ten standard culture flasks for each drug to be tested were plated with 5×10$^5$ cells of a given type in 5 mL of media and allowed to incubate for 16–24 hours at 37° C.

Day 2:

Fresh stocks of the compounds to be evaluated are prepared. For each drug, two of the ten culture flasks prepared on Day 1 are used as controls. The control flasks are treated with solvent only. Four flasks for each compound are then treated with serially-diluted concentrations of the compound. The remaining flasks are left untouched. The cells are incubated for 4 hours at 37° C.

After 4' hours the control flasks are counted (2 counts for each flask) and the cells per mL calculated based on the average of the control counts. The cells are then re-plated into six 60 mm dishes for each flask from dilutions based on the cells/mL of the control. (In the various test runs, cell concentrations ranged from approximately 50 to approximately 800 cells per mL.)

Day 15–20:

The cells are monitored for colony formation. When visible, the cells are stained with 0.5% crystal violet (in 95% EtOH) and counted. The plating efficiency for each dish is then calculated. The plating efficiencies of the six dishes for each flask are averaged and the standard deviation is calculated. The fraction of cell survival at each concentration is determined based on the controls.

Example 1
In vitro effect of SL-11048 (Compound 57) on MCF7

Following the standard protocol described above, the effect of SL-11048 (Compound 57) on MCF7 cell lines was evaluated. The results are depicted in FIG. 1. As shown in FIG. 1, $ED_{50}=1.49$ μM.

Example 2
In vitro effect of SL-11038 (Compound 23) on MCF7

Figure 2:
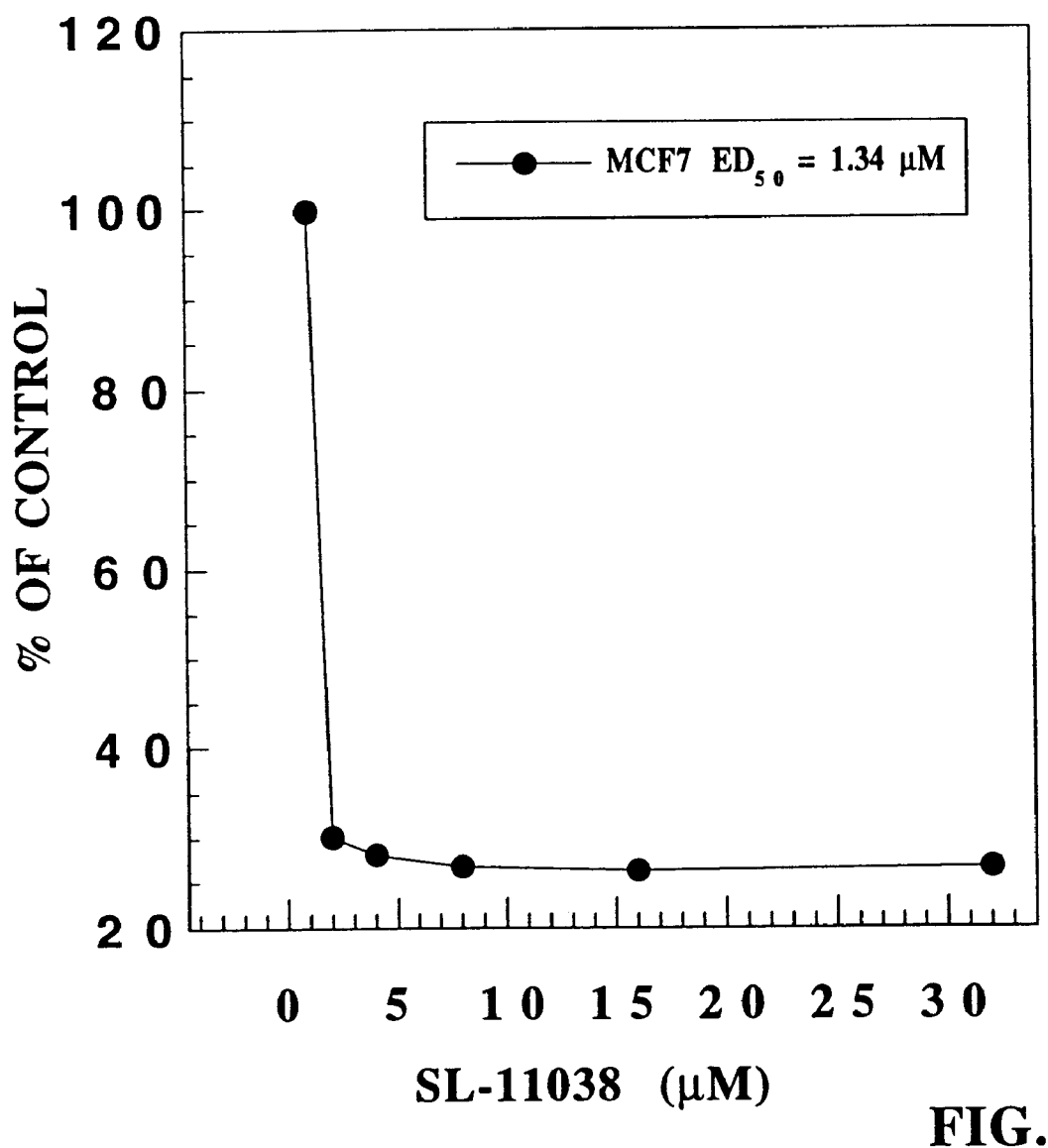
FIG. 2 is a graph depicting the in vitro effect of increasing concentrations of SL-11038 (Compound 23) on the survival of cultured breast cancer cells MCF7. $ED_{50}$=1.34 μM.

Following the standard protocol described above, the effect of SL-11038 (Compound 23) on MCF7 cell lines was evaluated. The results are depicted in FIG. 2. As shown in FIG. 2, $ED_{50}=1.34$ μM.

Example 3
In vitro effect of SL-11037 (Compound 28) on MCF7

Figure 3:
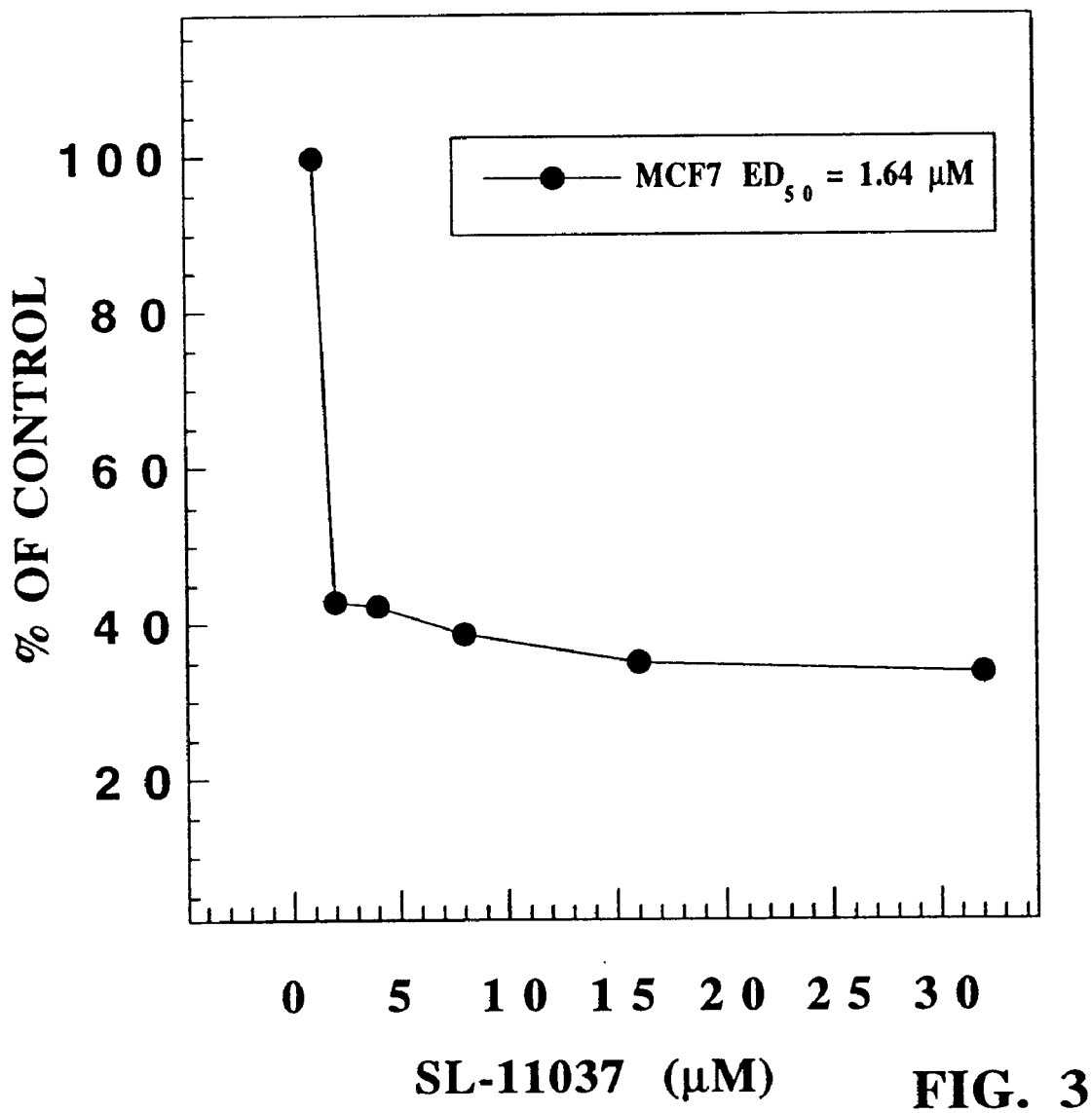
FIG. 3 is a graph depicting the in vitro effect of increasing concentrations of SL-11037 (Compound 28) on the survival of cultured breast cancer cells MCF7. $ED_{50}$=1.64 μM.

Following the standard protocol described above, the effect of SL-11037 (Compound 28) on MCF7 cell lines was evaluated. The results are depicted in FIG. 3. As shown in FIG. 3, $ED_{50}$ 1.64 μM.

Example 4
In vitro effect of SL-11043 (Compound 48) on MCF7

Figure 4:
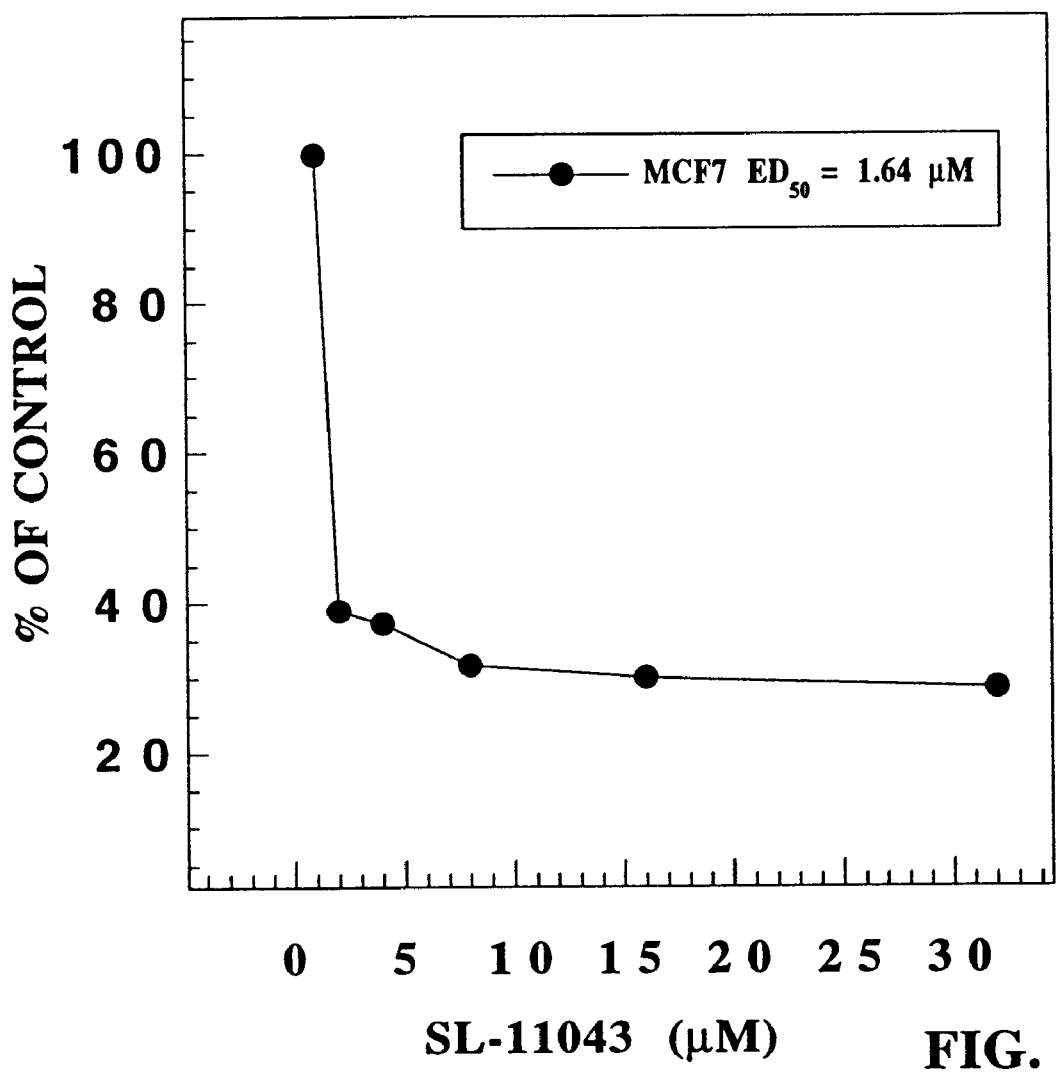
FIG. 4 is a graph depicting the in vitro effect of increasing concentrations of SL-11043 (Compound 48) on the survival of cultured breast cancer cells MCF7. $ED_{50}$=1.64 μM.

Following the standard protocol described above, the effect of SL-11043 (Compound 48) on MCF7 cell lines was evaluated. The results are depicted in FIG. 4. As shown in FIG. 4, $ED_{50}=1.64$ μM.

Example 5
In vitro effect of SL-11047 (Compound 58) on MCF7

Figure 5:
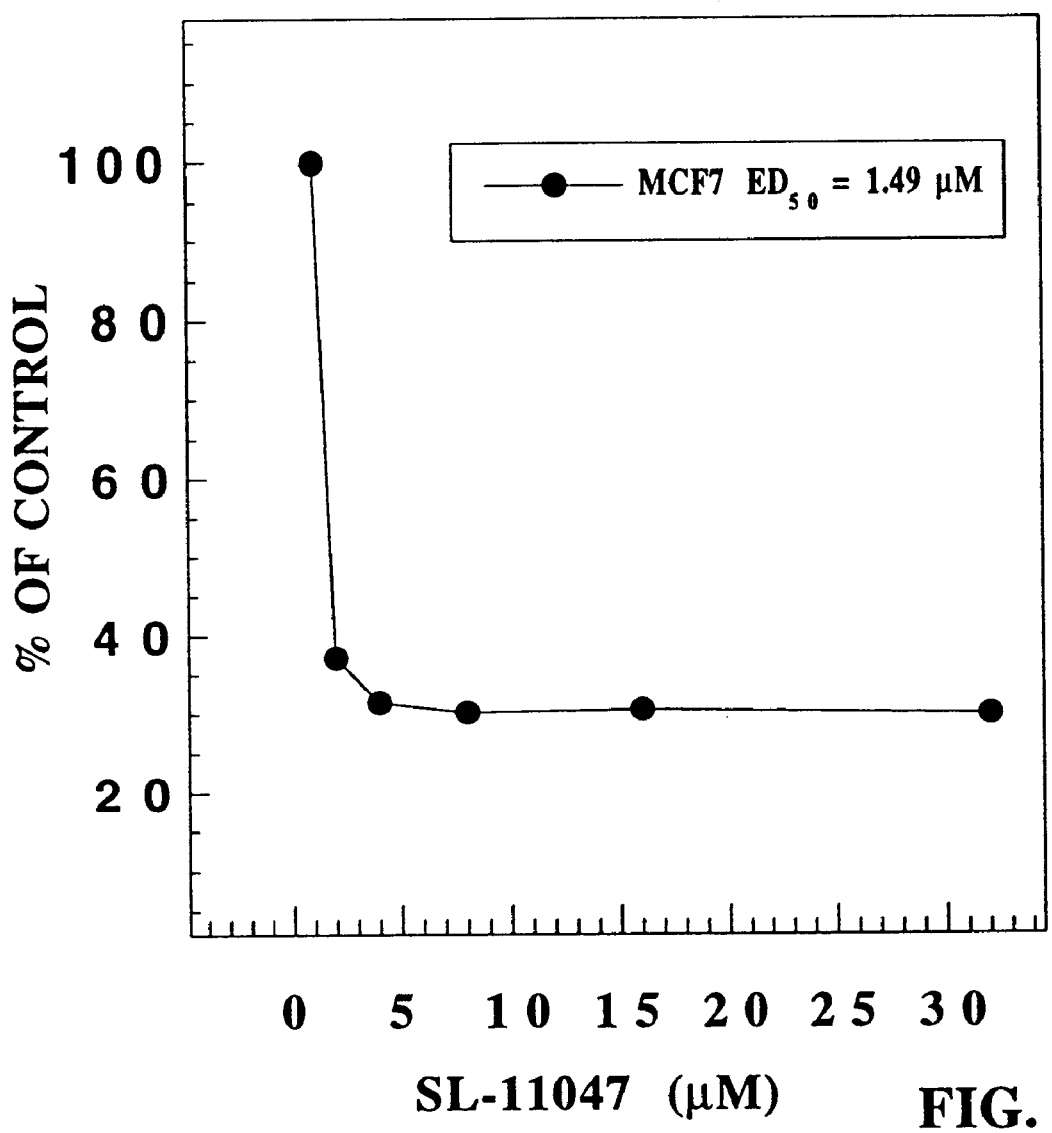
FIG. 5 is a graph depicting the in vitro effect of increasing concentrations of SL-11047 (Compound 58) on the survival of cultured breast cancer cells MCP7. $ED_{50}$=1.49 μM.

Following the standard protocol described above, the effect of SL-11047 (Compound 58) on MCF7 cell lines was evaluated. The results are depicted in FIG. 5. As shown in FIG. 5, $ED_{50}=1.49$ μM.

Example 6
In vitro effect of SL-11044 (Compound 47) on MCF7

Figure 6:
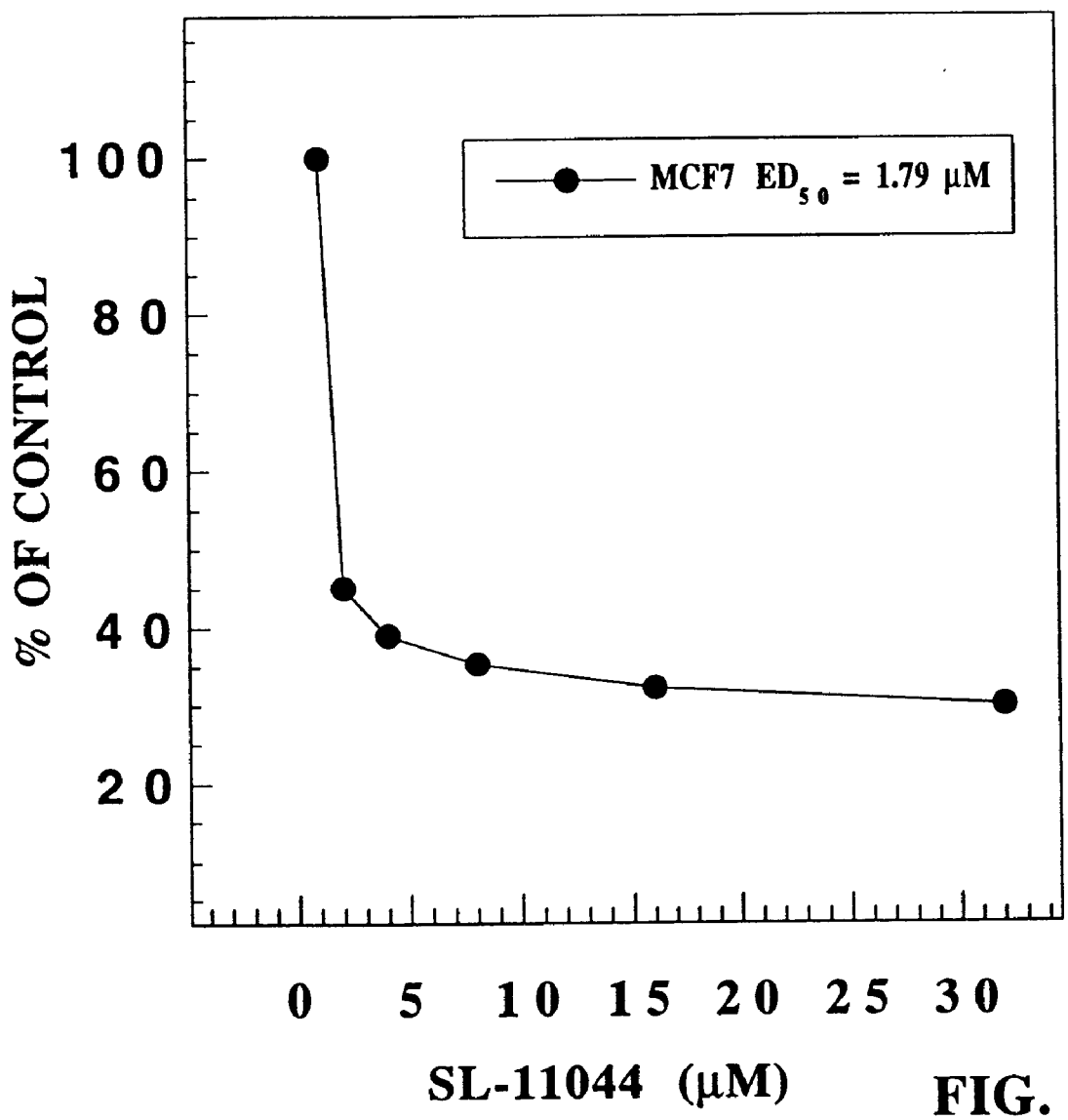
FIG. 6 is a graph depicting the in vitro effect of increasing concentrations of SL-11044 (Compound 47) on the survival of cultured breast cancer cells MCF7. $ED_{50}$1.79 μM.

Following the standard protocol described above, the effect of SL-11044 (Compound 47) on MCF7 cell lines was evaluated. The results are depicted in FIG. 6. As shown in FIG. 6, $ED_{50}=1.79$ μM.

Example 7
In vitro effect of 10 μM concentrations of SL-11033 (13, ■), SL-11027 (12, ▲), SL-11034 (36, ▼), and SL-11028 (35, ♦) on U251MG-NCI cells.

Here, the above-identified compounds were administered in a 10 μM dose to cultures of the human brain cancer cell line U251MG-NCI and evaluated according to the standard protocol described above. The results are shown in FIG. 7. At the 10 μM dosage used, SL-11027 (12) displayed marked inhibition of cell growth. Control=●.

Example 8
In vitro effect of 40 μM concentrations of SL-11033 (13, ■), SL-11027 (12, ▲), SL-11034 (36, ▼), and SL-11028 (35, ♦) on U251MG-NCI cells.

This Example is identical to Example 7, with the exception that a 40 μM dose was administered. The results are depicted in FIG. 8. Here, at the 40 μM dosage used, SL-11034 (36) displayed marked inhibition of cell growth. Control=●.

Examples 9–20

Here, a conventional MTT assay was used to evaluate percent cell survival. Exponentially growing monolayer cells were plated in 96-well plates at a density of 500 cells per well and allowed to grow for 24 hours. Serial dilutions of the drugs were added to the wells. Six days after drug treatment, 25 μl of MTT solution (5 mg/ml) was added to each well and incubated for 4 hours at 37° C. Then 100 μl of lysis buffer (20% sodium dodecyl sulfate, 50% DMF, and 0.8% acetic acid, pH 4.7) was added to each well and incubated for an additional 22 hours. A microplate reader ("EMAX"-brand, Molecular Devices, Sunnyvale, Calif.) set at 570 nm was used to determine the optical density of the cultures. Results are expressed as a ratio of the optical density in drug-treated wells to the optical density in wells treated with vehicle only.

The $ID_{50}$ doses for the compounds tested against the various cell lines are presented in Table 2. The $ID_{50}$ is the drug concentration that killed 50% of the cultured cells.

TABLE 2

Cytotoxic Activity Human Tumor Cell Lines

| | $ID_{50}$ (μM) | | | | |
|---|---|---|---|---|---|
| | A549 | HT-29 | PC-3 | MCF7 | U251MG NCI |
| SL-11037 (Cmpd 28) | 0.12 | 1.6 | 7.4 | >31.25 | 0.1 |
| SL-11038 (Cmpd 23) | 0.25 | 1.4 | 12.4 | >31.25 | 0.1 |
| SL-11043 (Cmpd 48) | 0.1 | 1.5 | >31.25 | 25.5 | 0.1 |
| SL-11044 (Cmpd 47) | 0.3 | 1.6 | >31.25 | >31.25 | 0.12 |
| SL-11047 (Cmpd 58) | 0.25 | 1.6 | 3.6 | 9.5 | 0.55 |
| SL-11048 (Cmpd 57) | 0.26 | 1.4 | 1.4 | >31.25 | 2 |

Example 9

Figure 9A:
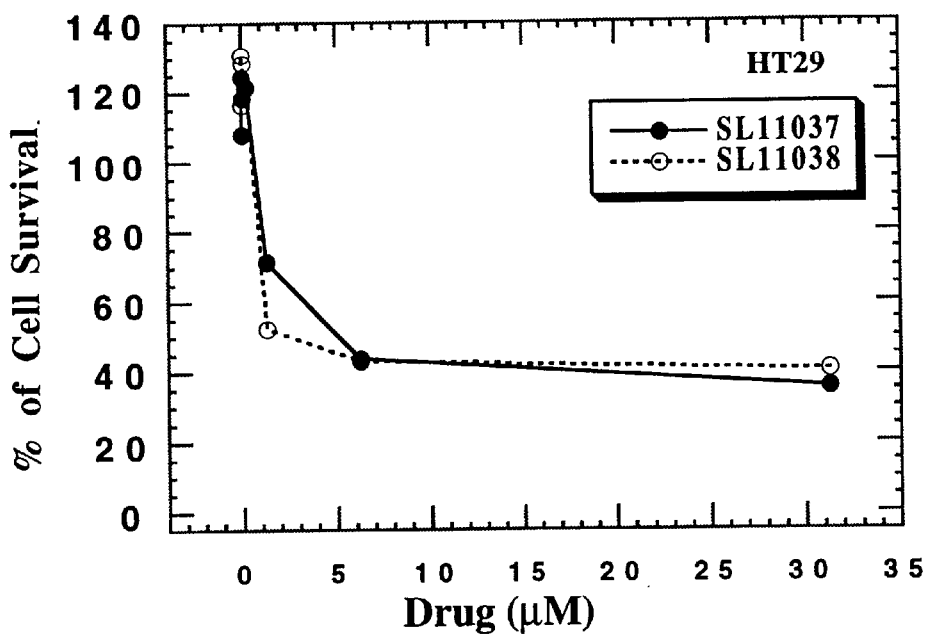
FIGS. 9A and 9B are graphs depicting the in vitro effect of increasing concentrations of SL-11037 (Compound 28, ●) and SL-11038 (Compound 23, ○) on the survival of cultured human colon cancer cells HT-29.
Figure 9B:
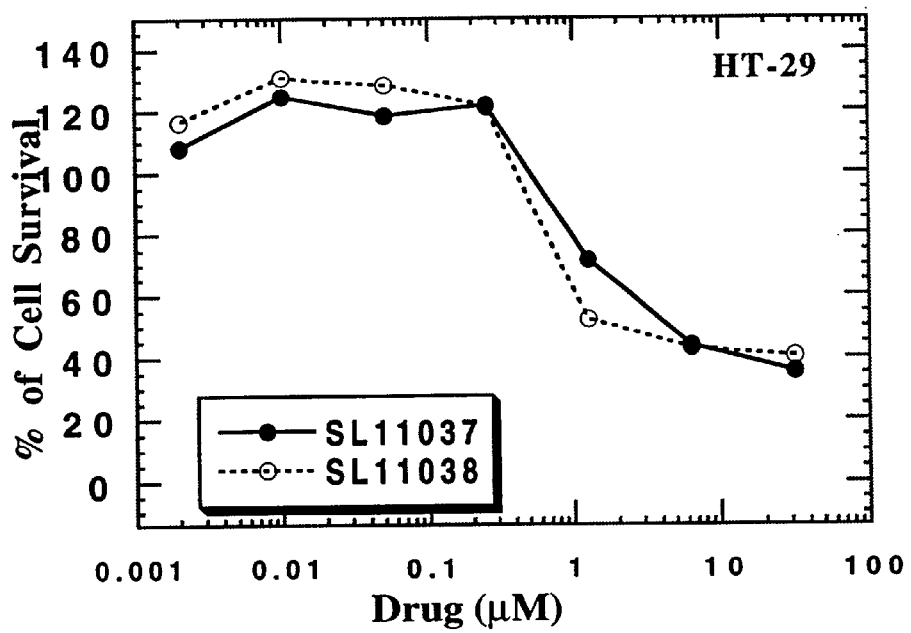

Using the standard MTT protocol described above, cultured HT29 cells were exposed to serial dilutions of compounds 28 (SL11037) and 23 (SL11038). The percent cell survival as compared to cultures exposed to vehicle alone was determined for each concentration of drug. The results are depicted in FIG. 9A and FIG. 9B. The $ID_{50}$ for these compounds against HT29 is given in Table 2.

Example 10

Figure 10A:
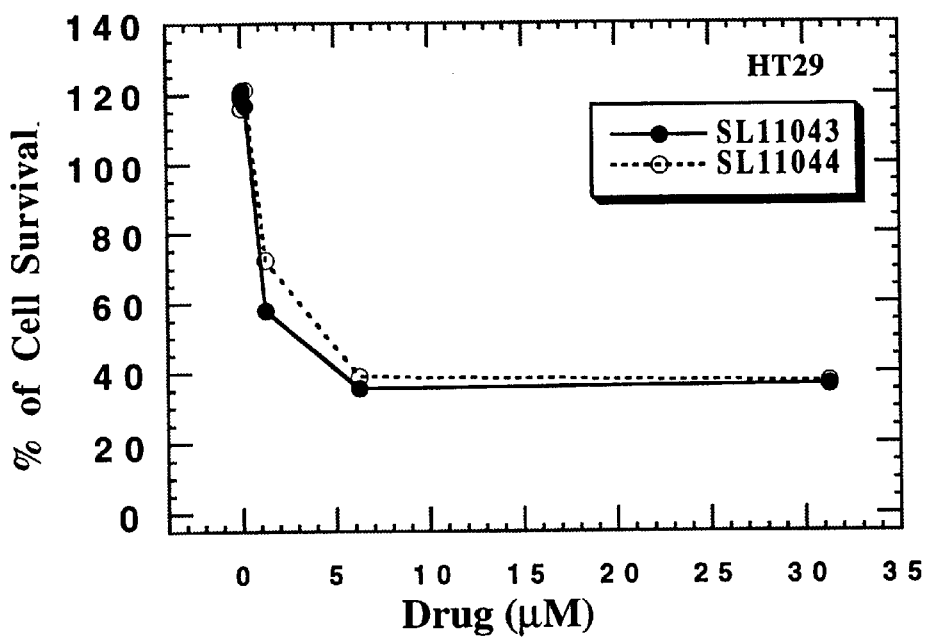
FIGS. 10A and 10B are graphs depicting the in vitro effect of increasing concentrations of SL-11043 (Compound 48, ●) and SL-11044 (Compound 47, ○) on the survival of cultured human colon cancer cells HT-29.
Figure 10B:
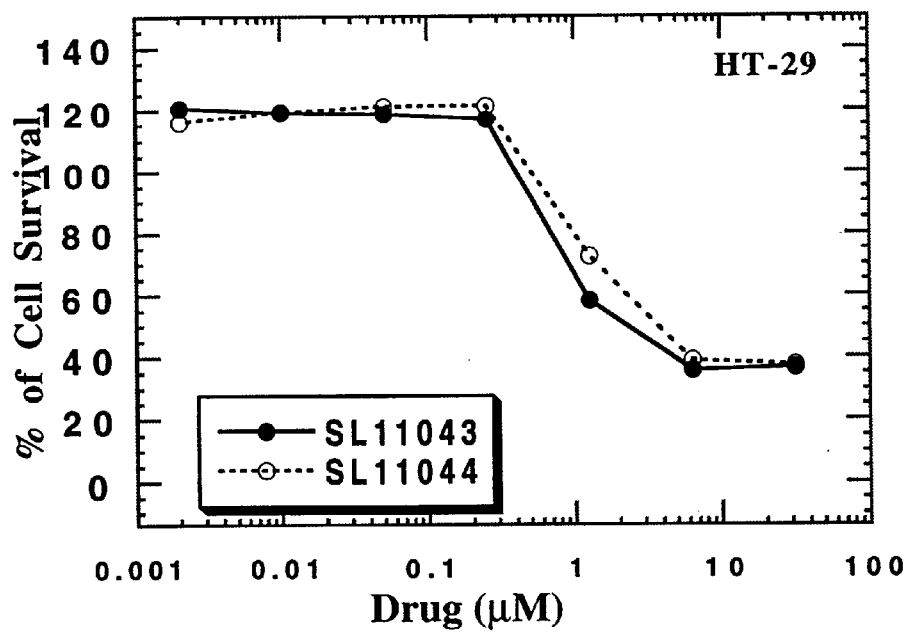

Using the standard MTT protocol described above, cultured HT29 cells were exposed to serial dilutions of compounds 48 (SL11043) and 47 (SL11044). The percent cell survival as compared to cultures exposed to vehicle alone was determined for each concentration of drug. The results are depicted in FIG. 10A and FIG. 10B. The $ID_{50}$ for these compounds against HT29 is given in Table 2.

Example 11

Figure 11A:
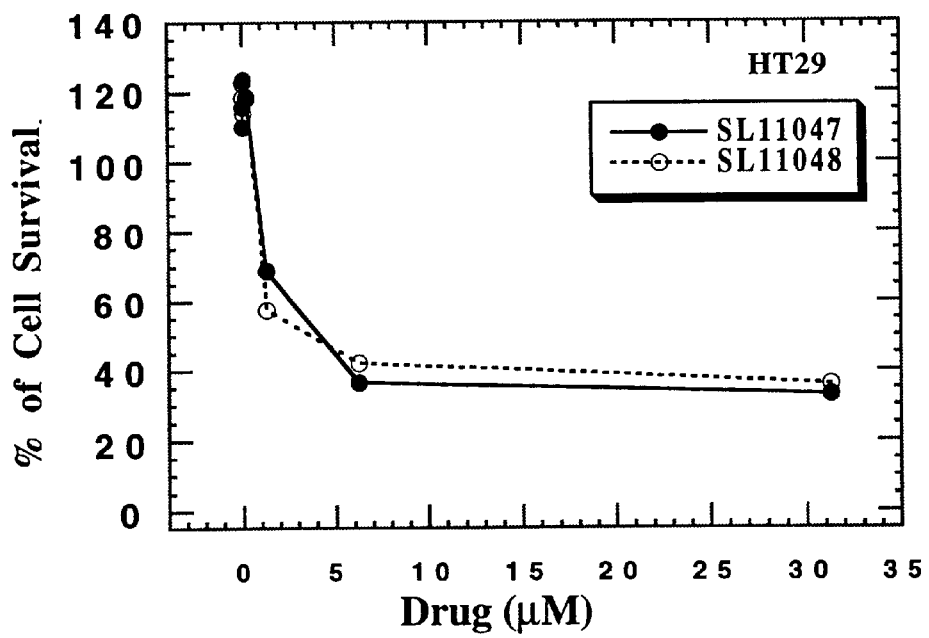
FIGS. 11A and 11B are graphs depicting the in vitro effect of increasing concentrations of SL-11047 (Compound 58, ●) and SL-11048 (Compound 57, ○) on the survival of cultured human colon cancer cells HT-29.
Figure 11B:
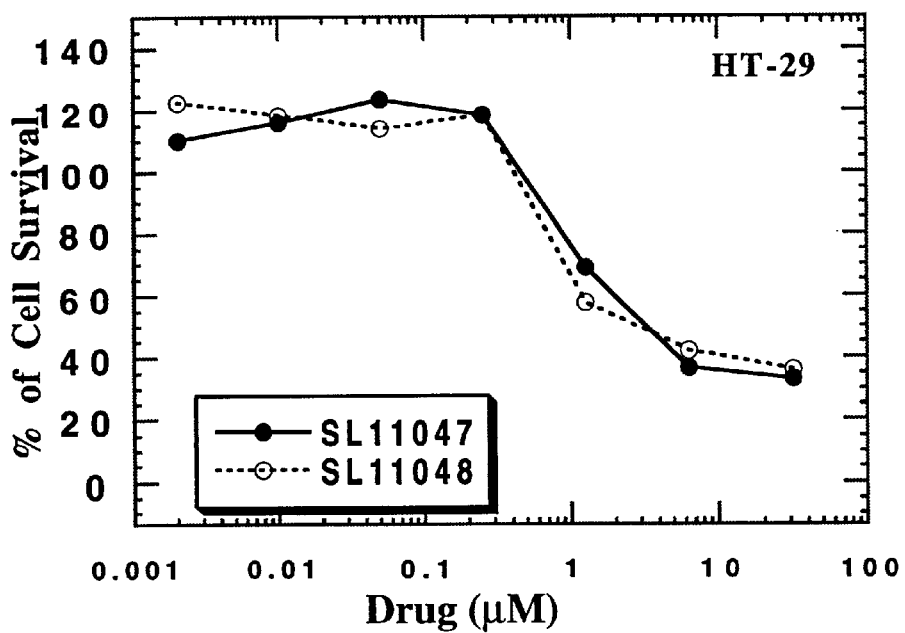

Using the standard MTT protocol described above, cultured HT29 cells were exposed to serial dilutions of compounds 58 (SL11047) and 57 (SL11048). The percent cell survival as compared to cultures exposed to vehicle alone was determined for each concentration of drug. The results are depicted in FIG. 11A and FIG. 11B. The $ID_{50}$ for these compounds against HT29 is given in Table 2.

Example 12

Figure 12A:
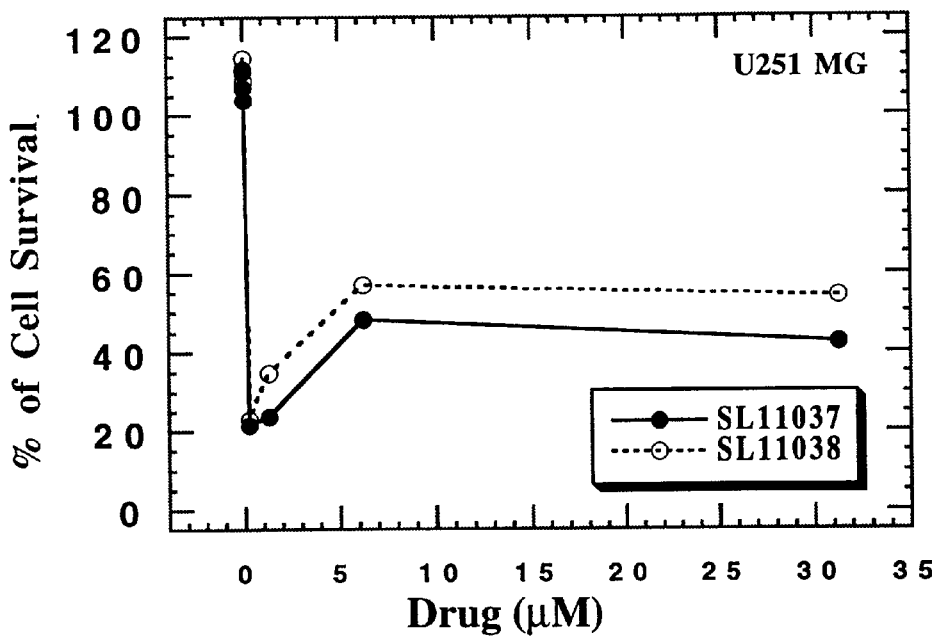
FIGS. 12A and 12B are graphs depicting the in vitro effect of increasing concentrations of SL-11037 (Compound 28, ●) and SL-11038 (Compound 23, ○) on the survival of cultured human brain cancer cells U251 MG.
Figure 12B:
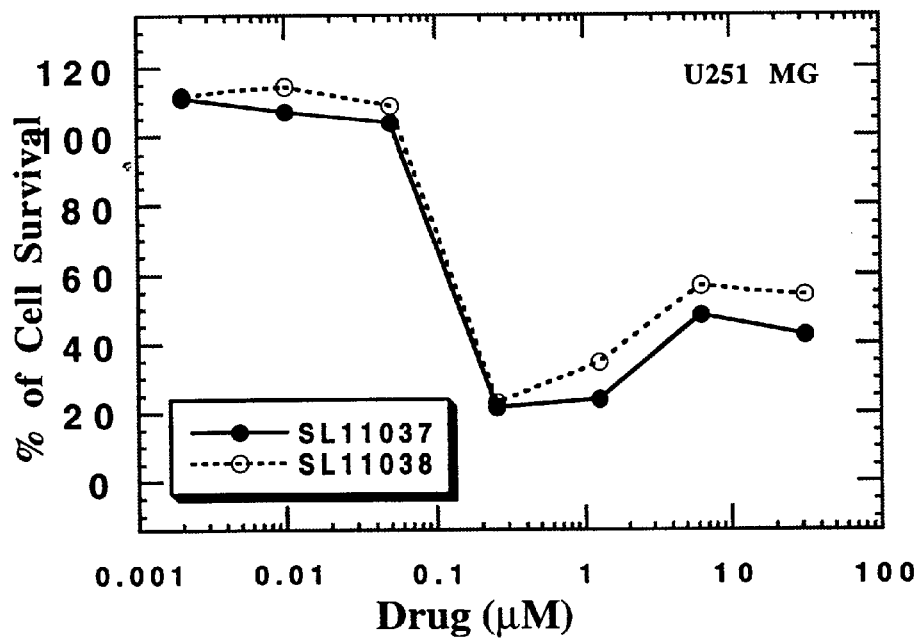

Using the standard MTT protocol described above, cultured U251 MG cells were exposed to serial dilutions of compounds 28 (SL11037) and 23 (SL11038). The percent cell survival as compared to cultures exposed to vehicle alone was determined for each concentration of drug. The results are depicted in FIG. 12A and FIG. 12B. The $ID_{50}$ for these compounds against U251 MG is given in Table 2.

Example 13

Figure 13A:
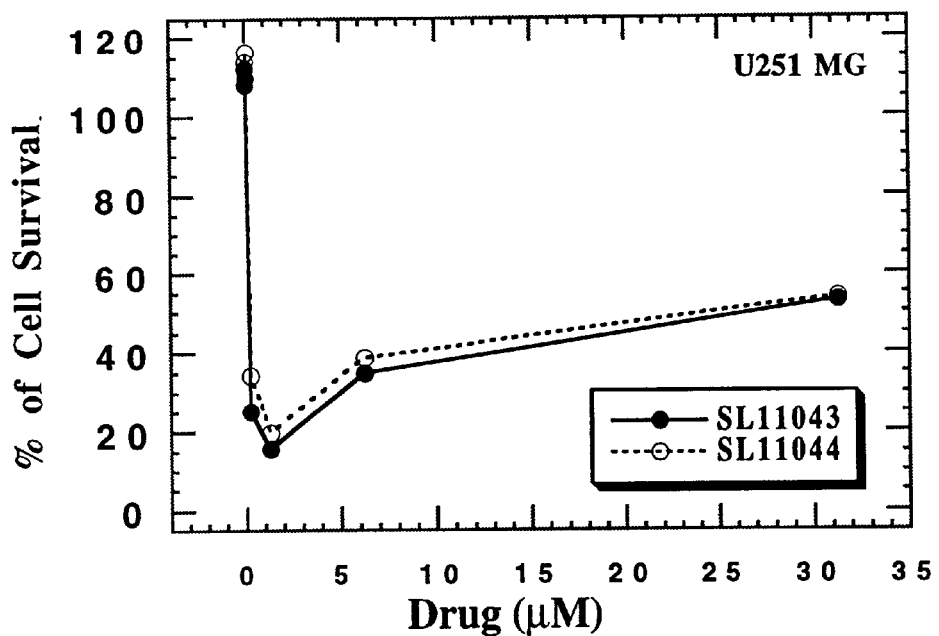
FIGS. 13A and 13B are graphs depicting the in vitro effect of increasing concentrations of SL-11043 (Compound 48, ●) and SL-11044 (Compound 47, ○) on the survival of cultured human brain cancer cells U215 MG.
Figure 13B:
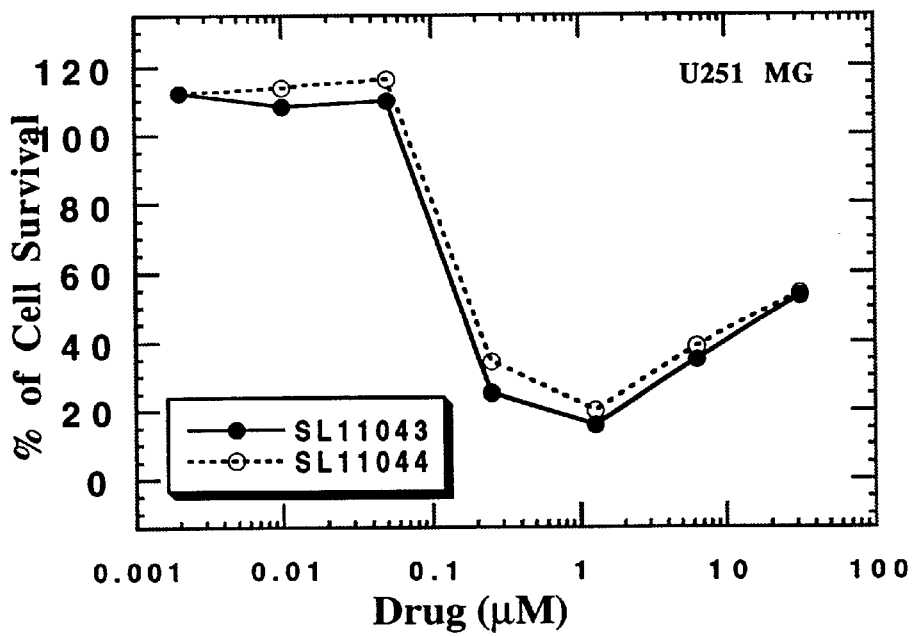

Using the standard MTT protocol described above, cultured U251 MG cells were exposed to serial dilutions of compounds 48 (SL11043) and 47 (SL11044). The percent cell survival as compared to cultures exposed to vehicle alone was determined for each concentration of drug. The results are depicted in FIG. 13A and FIG. 13B. The $ID_{50}$ for these compounds against U251 MG is given in Table 2.

Example 14

Figure 14A:
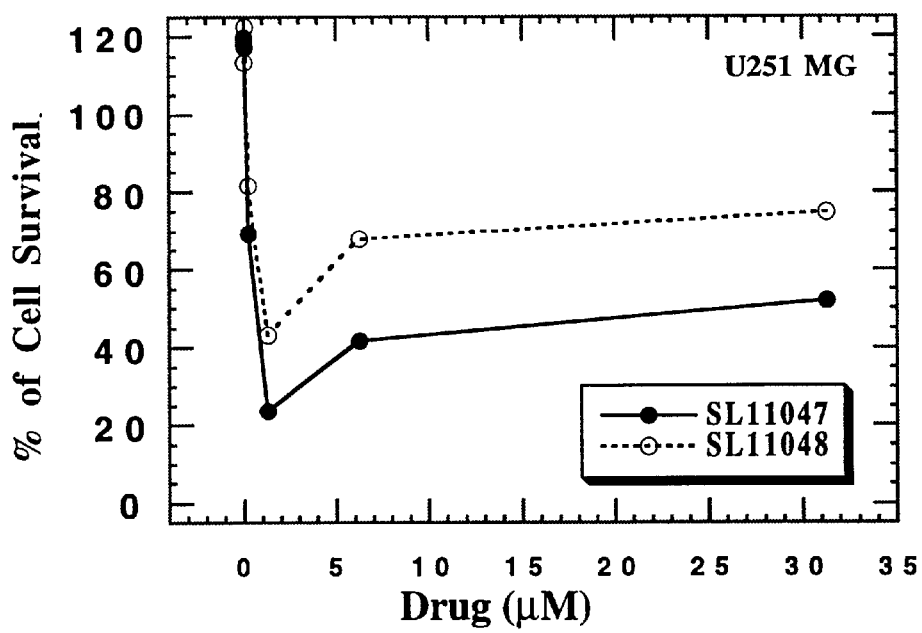
FIGS. 14A and 14B are graphs depicting the in vitro effect of increasing concentrations of SL-11047 (Compound 58, ●) and SL-11048 (Compound 57, ○) on the survival of cultured human brain cancer cells U251 MG.
Figure 14B:
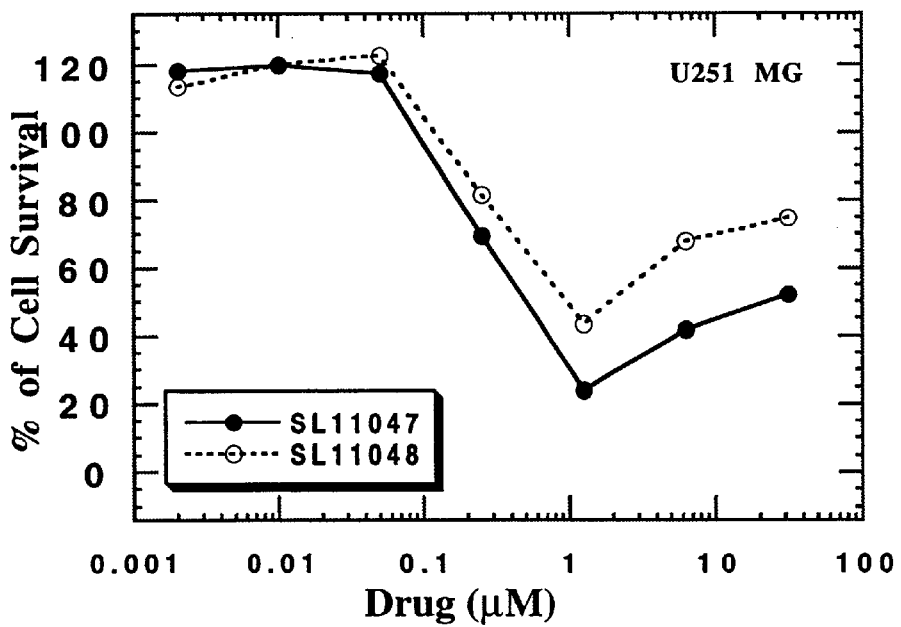

Using the standard MTT protocol described above, cultured U251 MG cells were exposed to serial dilutions of compounds 58 (SL11047) and 57 (SL11048). The percent cell survival as compared to cultures exposed to vehicle alone was determined for each concentration of drug. The results are depicted in FIG. 14A and FIG. 14B. The $ID_{50}$ for these compounds against U251 MG is given in Table 2.

Example 15

Figure 15A:
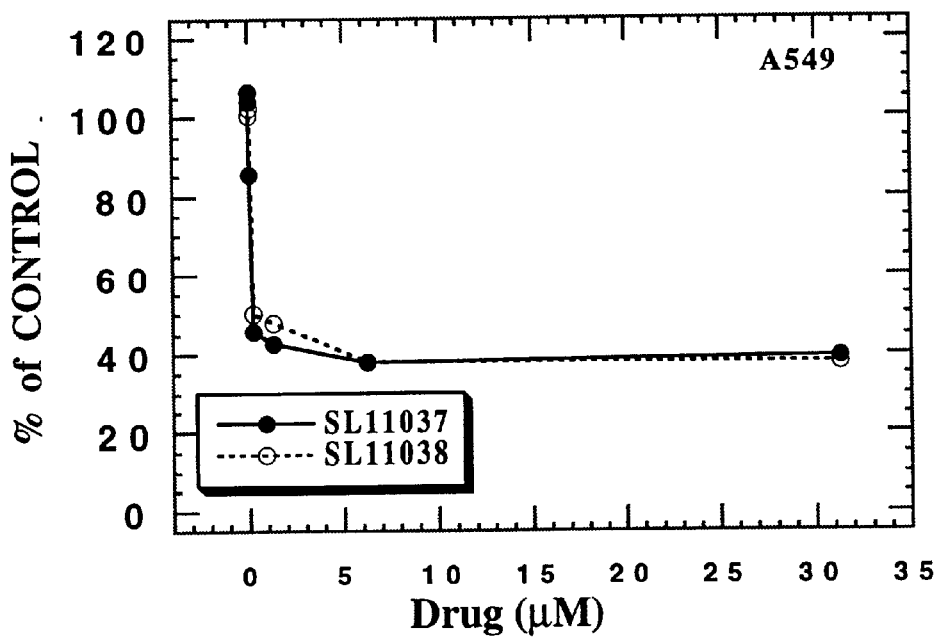
FIGS. 15A and 15B are graphs depicting the in vitro effect of increasing concentrations of SL-11037 (Compound 28, ●) and SL-11038 (Compound 23, ○) on the survival of cultured human lung cancer cells A549.
Figure 15B:
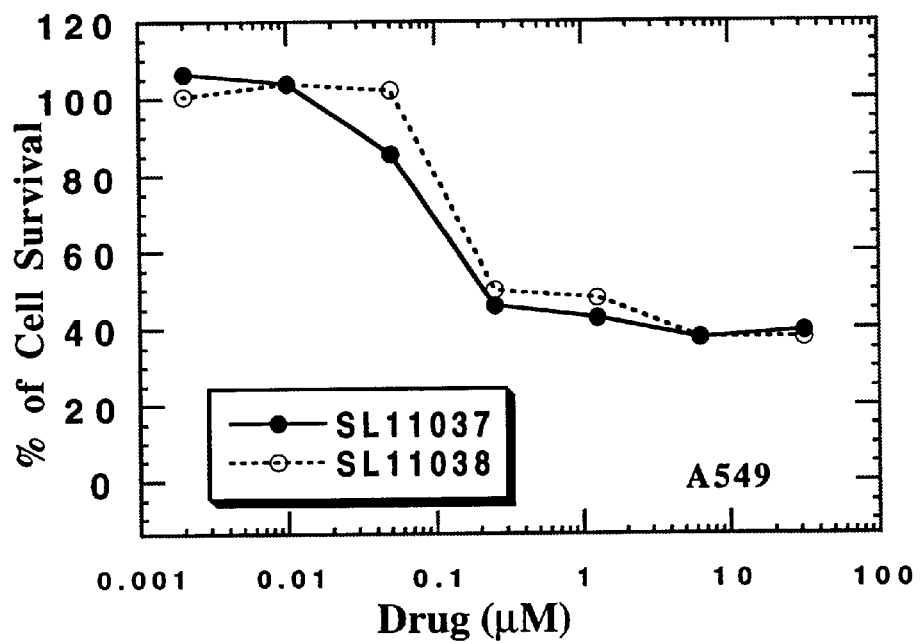

Using the standard MTT protocol described above, cultured A549 cells were exposed to serial dilutions of compounds 28 (SL11037) and 23 (SL11038). The percent cell survival as compared to cultures exposed to vehicle alone was determined for each concentration of drug. The results are depicted in FIG. 15A and FIG. 15B. The $ID_{50}$ for these compounds against A549 is given in Table 2.

Example 16

Figure 16A:
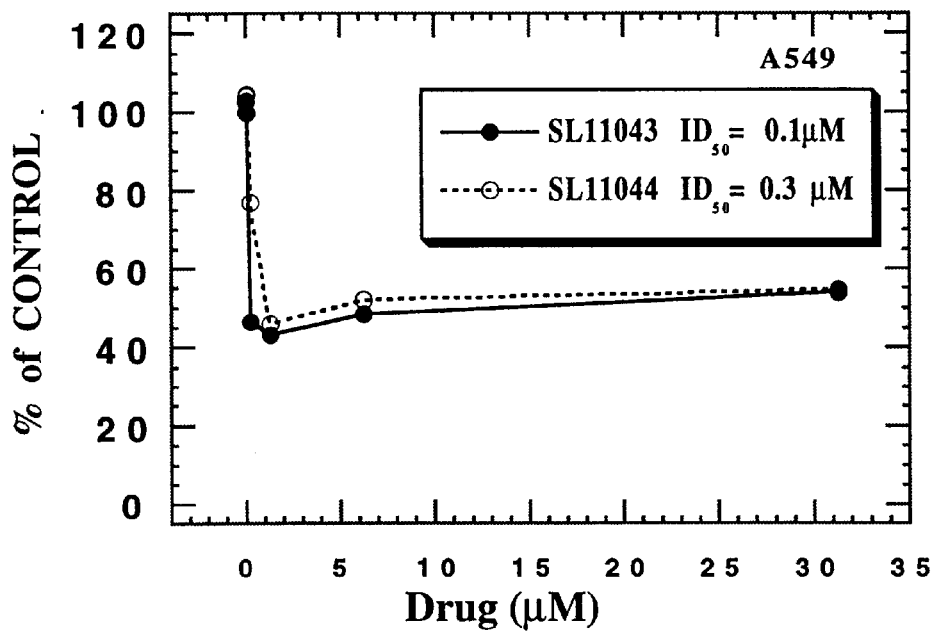
FIGS. 16A and 16B are graphs depicting the in vitro effect of increasing concentrations of SL-11043 (Compound 48, ●) and SL-11044 (Compound 47, ○) on the survival of cultured human lung cancer cells A549.
Figure 16B:
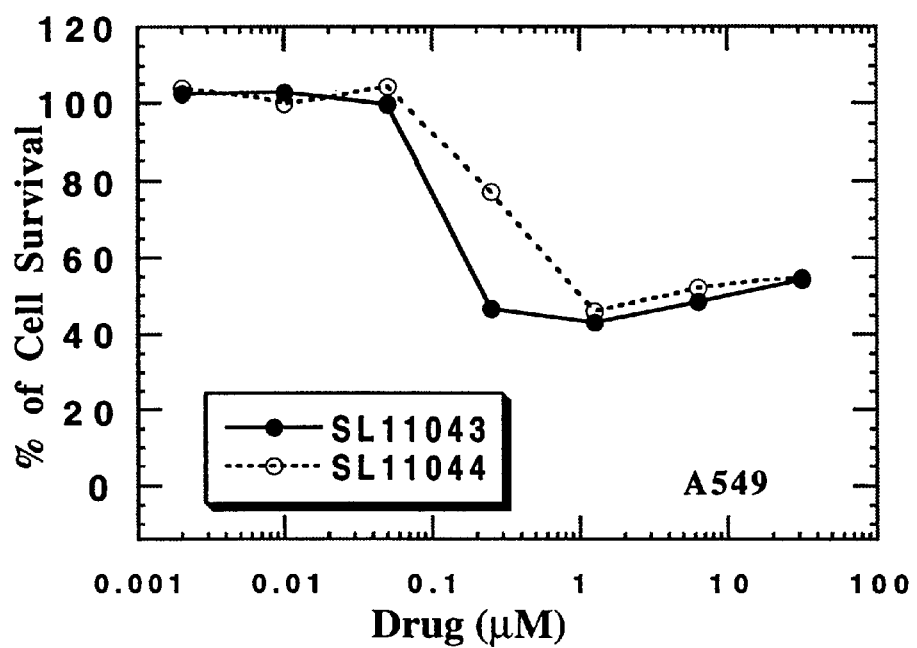

Using the standard MTT protocol described above, cultured A549 cells were exposed to serial dilutions of compounds 48 (SL11043) and 47 (SL11044). The percent cell survival as compared to cultures exposed to vehicle alone was determined for each concentration of drug. The results are depicted in FIG. 16A and FIG. 16B. The $ID_{50}$ for these compounds against A549 is given in Table 2.

Example 17

Figure 17A:
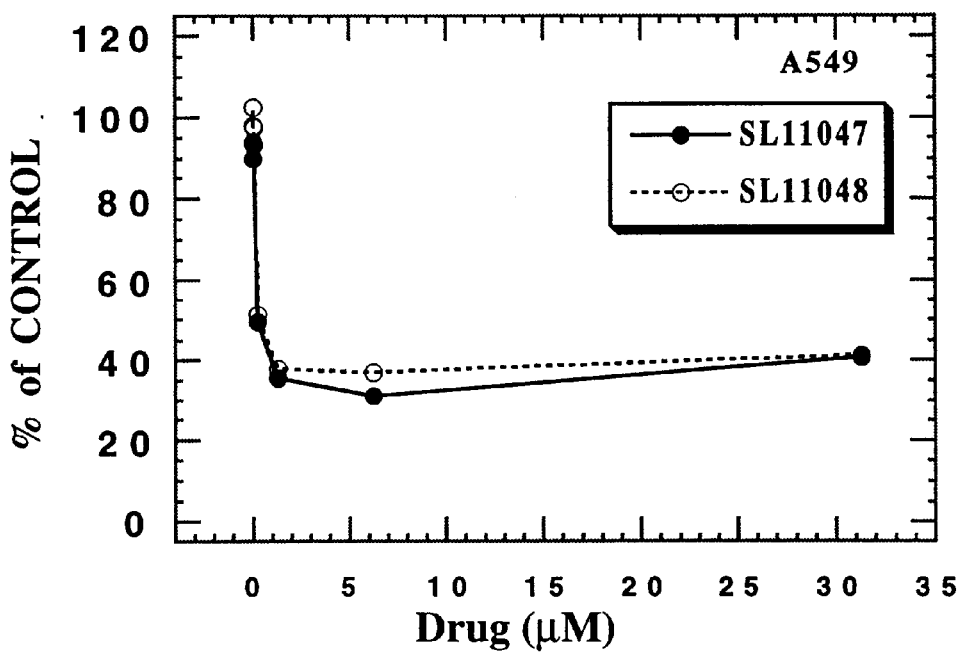
FIGS. 17A and 17B are graphs depicting the in vitro effect of increasing concentrations of SL-11047 (Compound 58, ●) and SL-11048 (Compound 57, ○) on the survival of cultured human lung cancer cells A549.
Figure 17B:
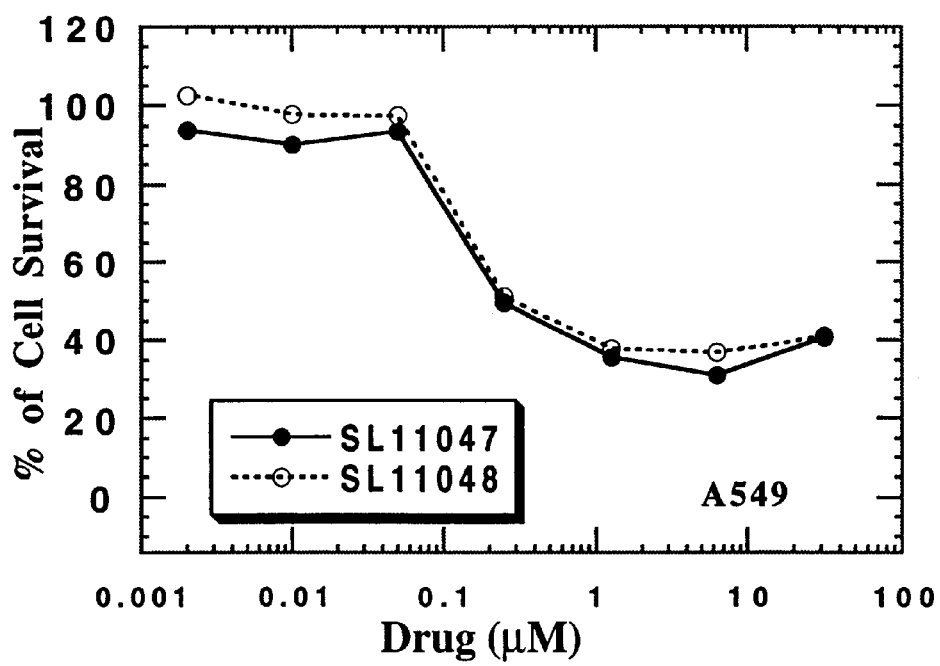

Using the standard MTT protocol described above, cultured A549 cells were exposed to serial dilutions of compounds 58 (SL11047) and 57 (SL11048). The percent cell survival as compared to cultures exposed to vehicle alone was determined for each concentration of drug. The results are depicted in FIG. 17A and FIG. 17B. The $ID_{50}$ for these compounds against A549 is given in Table 2.

Example 18

Figure 18A:
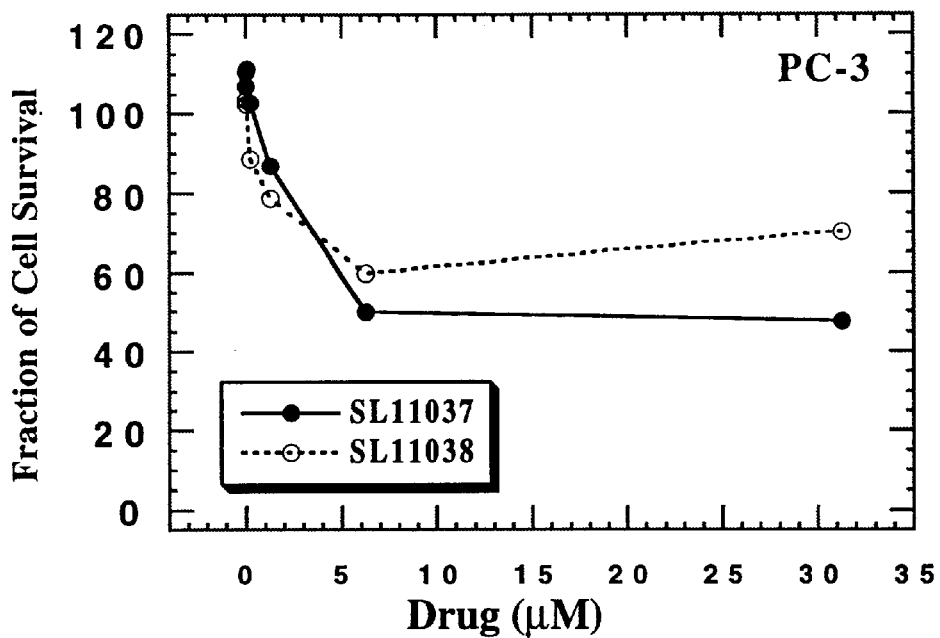
FIGS. 18A and 18B are graphs depicting the in vitro effect of increasing concentrations of SL-11037 (Compound 28, ●) and SL-11038 (Compound 23, ○) on the survival of cultured human prostate cancer cells PC3.
Figure 18B:
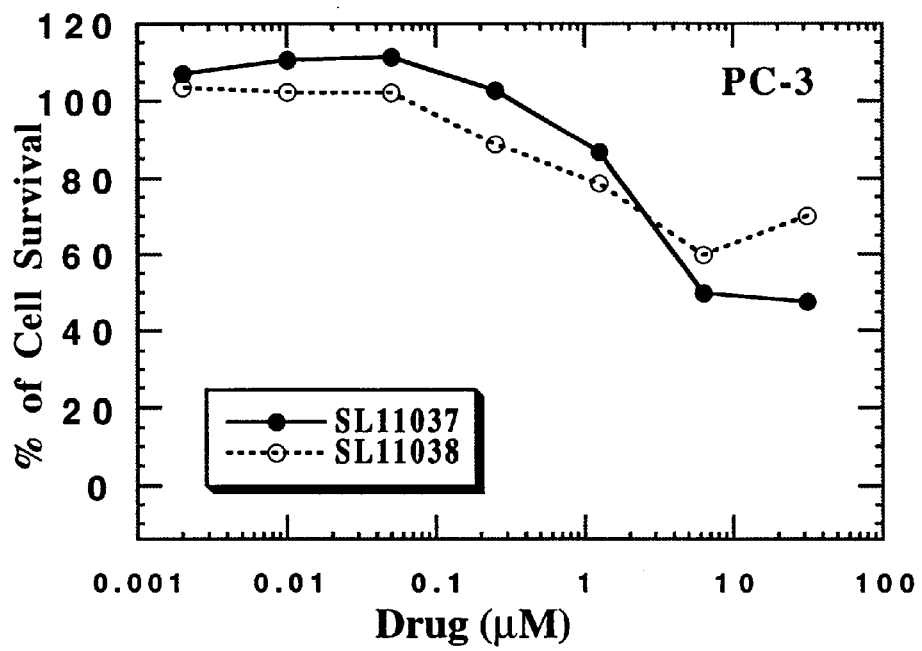

Using the standard MTT protocol described above, cultured PC3 cells were exposed to serial dilutions of compounds 28 (SL11037) and 23 (SL11038). The percent cell survival as compared to cultures exposed to vehicle alone was determined for each concentration of drug. The results are depicted in FIG. 18A and FIG. 18B. The $ID_{50}$ for these compounds against PC3 is given in Table 2.

Example 19

Figure 19A:
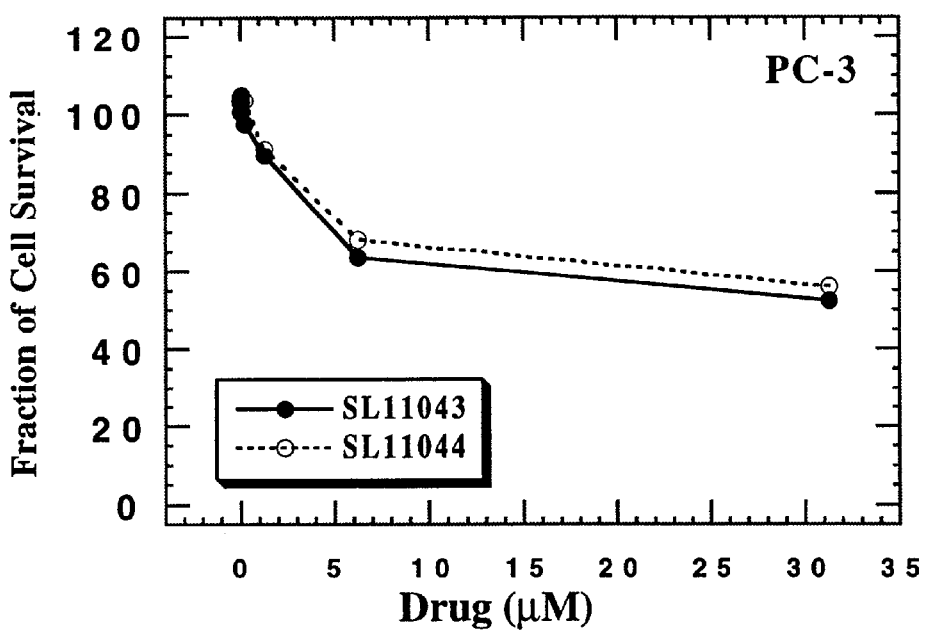
FIGS. 19A and 19B are graphs depicting the in vitro effect of increasing concentrations of SL-11043 (Compound 48, ●) and SL-11044 (Compound 47, ○) on the survival of cultured human prostate cancer cells PC3.
Figure 19B:
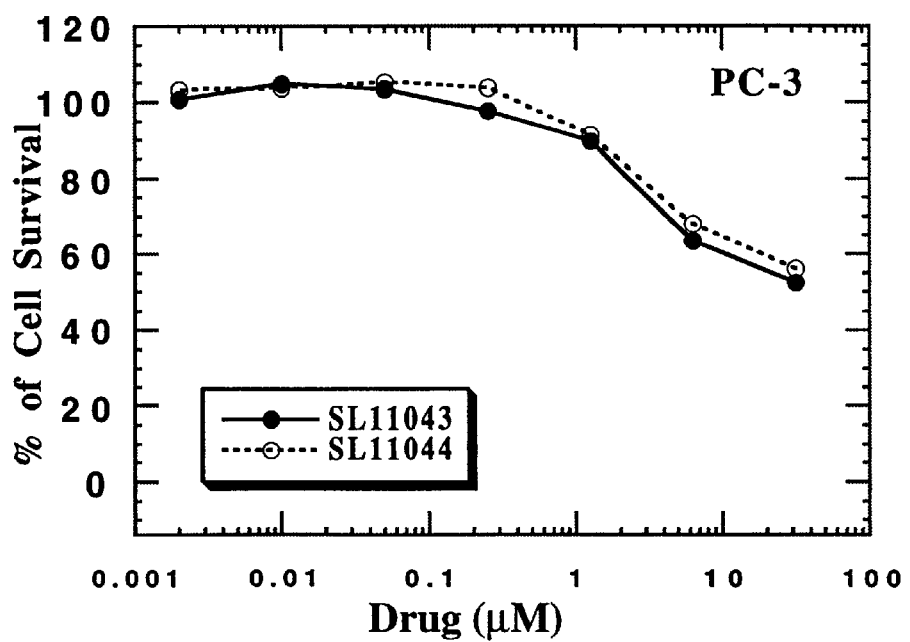

Using the standard MTT protocol described above, cultured PC3 cells were exposed to serial dilutions of compounds 48 (SL11043) and 47 (SL11044). The percent cell survival as compared to cultures exposed to vehicle alone was determined for each concentration of drug. The results are depicted in FIG. 19A and FIG. 19B. The $ID_{50}$ for these compounds against PC3 is given in Table 2.

Example 20

Figure 20A:
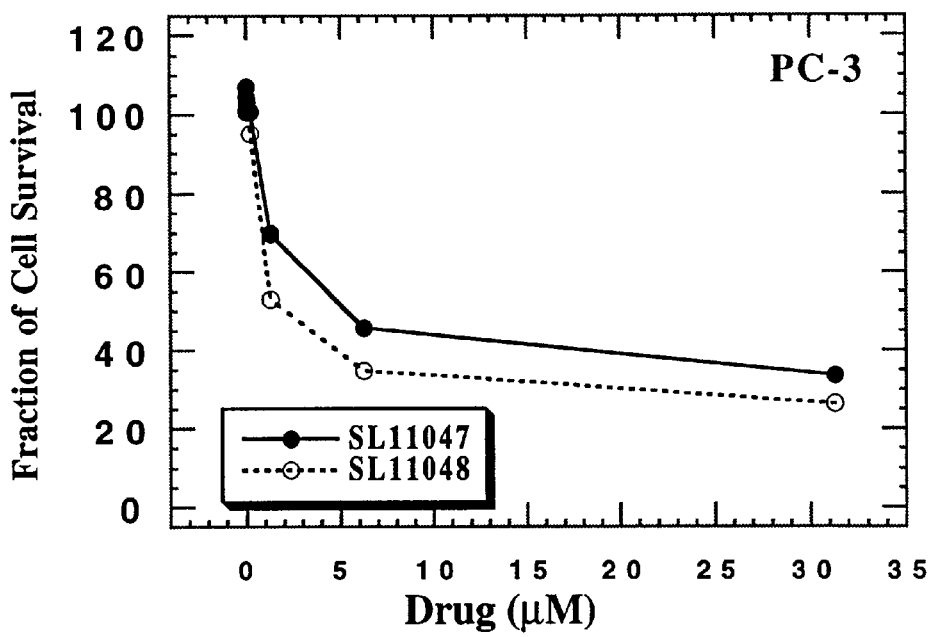
FIGS. 20A and 20B are graphs depicting the in vitro effect of increasing concentrations of SL-11047 (Compound 58, ●) and SL-11048 (Compound 57, ○) on the survival of cultured human prostate cancer cells PC3.
Figure 20B:
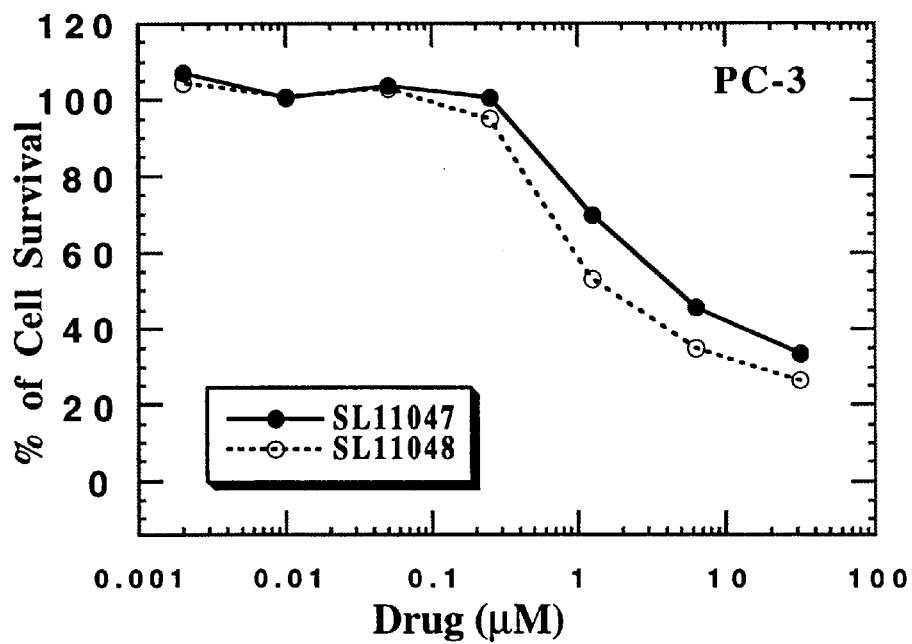

Using the standard MTT protocol described above, cultured PC3 cells were exposed to serial dilutions of compounds 58 (SL11047) and 57 (SL11048). The percent cell survival as compared to cultures exposed to vehicle alone was determined for each concentration of drug. The results are depicted in FIG. 20A and FIG. 20B. The $ID_{50}$ for these compounds against PC3 is given in Table 2.

Bibliography

Ashton, Wallace T.; Meurer, Laura Canning; Cantone, Christine L.; Field, A. Kirk; Hannah, John, Karkas, John D., Liou, Richard; Patel, Gool F.; Perry, Helen C.; Wagner, Arthur F.; Walton, Edward, and Tolman, Richard L., *J. Med. Chem* (1988) 31:2304

Bergeron, R. J.; McManis, J. S.; Liu, C. Z.; Feng, Y.; Weinar, W. R.; Luchetta, G. R.; Wu, Q., Ortiz-Ocasio, J.; Vinson, J. R. T.; Kramer, D.; and Porter, C., *J. Med. Chem.* (1994), 37:3464–3476.

Buchman, E. R.; Reiner, A. O.; Thurston, S.; Sheatter, M. J., *J. Am. Chem. Soc.* (1942), 64:2696–2700.

Fabiano, E., Golding, B. T., and Sadeghi, M. M., *Synthesis* (1987), 190–192.

Israel et al., *J. Med. Chem.* (1964), 7:710.

Miller, A. E. G., Biss, J. N., and Schwartzman, L. H., *J. Org. Chem.* (1959), 24:627.

What is claimed is:

1. Compounds of Formula I:

E—NH—D—NH—B—A—B—NH—D—NH—E     (I)

wherein A is selected from the group consisting of cis-$C_2$–$C_6$ alkene and $C_3$–$C_6$ cycloalkyl, cycloalkenyl, and cycloaryl;

B is independently selected from the group consisting of a single bond and $C_1$–$C_6$ alkyl and alkenyl;

D is independently selected from the group consisting of $C_1$–$C_6$ alkyl and alkenyl, and $C_3$–$C_6$ cycloalkyl, cycloalkenyl, and cycloaryl;

E is methyl;

and pharmaceutically-suitable salts thereof.

2. Compounds according to claim 1, wherein A is selected from the group consisting of cyclopropyl and cyclobutyl.

3. Compounds according to claim 1, wherein B is selected from the group consisting of a single bond, methyl, and ethyl.

4. Compounds according to claim 1, wherein D is propyl.

5. Compounds according to claim 1, wherein A is selected from the group consisting of cis-2-butene, cis-cyclopropyl, trans-cyclopropyl, cis-cyclobutyl and trans-cyclobutyl; B is selected from the group consisting of a single bond and methyl; and D is propyl.

6. The compound according to claim 1, wherein A is cis-cyclopropyl, B is a single bond, and D is propyl.

7. The compound according to claim 1, wherein A is trans-cyclopropyl, B is a single bond, and D is propyl.

8. The compound according to claim 1, wherein A is cis-cyclopropyl, B is methyl, and D is propyl.

9. The compound according to claim 1, wherein A is trans-cyclopropyl, B is methyl, and D is propyl.

10. The compound according to claim 1, wherein A is trans-cyclobutyl, B is a single bond, and D is propyl.

11. The compound according to claim 1, wherein A is cis-cyclobutyl, B is a single bond, and D is propyl.

12. The compound according to claim 1, wherein A is trans-cyclobutyl, B is methyl, and D is propyl.

13. The compound according to claim 1, wherein A is cis-cyclobutyl, B is methyl, and D is propyl.

14. The compound according to claim 1, wherein A is cis-2-butene, B is a single bond, and D is propyl.

15. A pharmaceutical unit dosage form for the inhibition of neoplastic cell growth comprising one or more compounds according to claim 1 in combination with a pharmaceutically-suitable carrier.

16. The pharmaceutical unit dosage form of claim 15, wherein the carrier is a solid carrier.

17. The pharmaceutical unit dosage form of claim 15, wherein the carrier is a liquid carrier.

18. A method of inhibiting growth of cancer cells comprising treating the cancer cells with an effective growth-inhibiting amount of one or more compounds according to claim 1.

19. The method of claim 18, wherein an amount of one or more of the compounds is administered to a human cancer patient in need thereof which is effective to inhibit the growth of the cancer.

20. The method of claim 19, wherein the amount of one or more of the compounds is administered parenterally in combination with a pharmaceutically-acceptable liquid or solid carrier.

21. The method of claim 19, wherein the amount of one or more of the compounds is administered intravenously in combination with a pharmaceutically-acceptable liquid carrier.

22. The method of claim 19, wherein the amount of one or more of the compounds is administered orally in combination with a pharmaceutically-acceptable liquid or solid carrier.

* * * * *